United States Patent
Kronenberg et al.

(10) Patent No.: US 8,143,374 B2
(45) Date of Patent: Mar. 27, 2012

(54) POLYPEPTIDE DERIVATIVES OF PARATHYROID HORMONE (PTH)

(75) Inventors: Henry M. Kronenberg, Belmont, MA (US); John T. Potts, Jr., Newton, MA (US); Thomas J. Gardella, Needham, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 12/376,389

(22) PCT Filed: Aug. 3, 2007

(86) PCT No.: PCT/US2007/017338
§ 371 (c)(1),
(2), (4) Date: Nov. 17, 2009

(87) PCT Pub. No.: WO2008/019062
PCT Pub. Date: Feb. 14, 2008

(65) Prior Publication Data
US 2010/0081612 A1    Apr. 1, 2010

Related U.S. Application Data

(60) Provisional application No. 60/835,422, filed on Aug. 4, 2006.

(51) Int. Cl.
*A61K 38/00* (2006.01)
*A61K 38/16* (2006.01)
*C07K 5/00* (2006.01)

(52) U.S. Cl. ......... 530/324; 530/326; 530/325; 514/1.1; 514/16.7; 514/21.3

(58) Field of Classification Search .................. None
See application file for complete search history.

(56) References Cited

U.S. PATENT DOCUMENTS

| | | |
|---|---|---|
| 4,086,196 A | 4/1978 | Tregear |
| 4,366,241 A | 12/1982 | Tom et al. |
| 4,423,037 A | 12/1983 | Rosenblatt et al. |
| 4,511,502 A | 4/1985 | Builder et al. |
| 4,512,922 A | 4/1985 | Jones et al. |
| 4,518,526 A | 5/1985 | Olson |
| 4,620,948 A | 11/1986 | Builder et al. |
| 4,675,189 A | 6/1987 | Kent et al. |
| 4,698,328 A | 10/1987 | Neer et al. |
| 4,736,866 A | 4/1988 | Leder et al. |
| 4,761,406 A | 8/1988 | Flora et al. |
| 4,771,124 A * | 9/1988 | Rosenblatt et al. ............ 530/324 |
| 4,843,000 A | 6/1989 | Litman et al. |
| 4,849,338 A | 7/1989 | Litman et al. |
| 5,010,010 A | 4/1991 | Gautvik et al. |
| 5,208,041 A | 5/1993 | Sindrey |
| 5,217,896 A | 6/1993 | Kramer et al. |
| 5,227,487 A | 7/1993 | Haugland et al. |
| 5,274,113 A | 12/1993 | Kang et al. |
| 5,326,692 A | 7/1994 | Brinkley et al. |
| 5,350,836 A | 9/1994 | Kopchick et al. |
| 5,382,658 A | 1/1995 | Kronis et al. |
| 5,393,869 A | 2/1995 | Nakagawa et al. |
| 5,405,975 A | 4/1995 | Kuhn et al. |
| 5,433,896 A | 7/1995 | Kang et al. |
| 5,442,045 A | 8/1995 | Haugland et al. |
| 5,451,663 A | 9/1995 | Kang et al. |
| 5,453,517 A | 9/1995 | Kuhn et al. |
| 5,457,034 A | 10/1995 | della Valle et al. |
| 5,459,276 A | 10/1995 | Kuhn et al. |
| 5,462,856 A | 10/1995 | Lerner et al. |
| 5,494,806 A | 2/1996 | Segre et al. |
| 5,496,801 A | 3/1996 | Holthuis et al. |
| 5,501,979 A | 3/1996 | Geller et al. |
| 5,516,864 A | 5/1996 | Kuhn et al. |
| 5,527,772 A | 6/1996 | Holick |
| 5,556,940 A | 9/1996 | Willick et al. |
| 5,573,909 A | 11/1996 | Singer et al. |
| 5,578,461 A | 11/1996 | Sherwin et al. |
| 5,589,452 A | 12/1996 | Krstenansky et al. |
| 5,605,815 A | 2/1997 | Broadus et al. |
| 5,616,560 A | 4/1997 | Geddes et al. |
| 5,648,270 A | 7/1997 | Kuhn et al. |
| 5,656,465 A | 8/1997 | Panicali et al. |
| 5,693,616 A | 12/1997 | Krstenansky et al. |
| 5,695,955 A | 12/1997 | Krstenansky et al. |

(Continued)

FOREIGN PATENT DOCUMENTS

AU    668118    4/1996
(Continued)

OTHER PUBLICATIONS

Gensure et al., "Identification of Determinants of Inverse Agonism in a Constitutively Active Parathyroid Hormone/Parathyroid Hormone-Related Peptide Receptor by Photoaffinity Cross-Linking and Mutational Analysis," *J. Biol. Chem.* 276:42692-42699 (2001).
Abou-Samra et al., "Expression Cloning of a Common Receptor for Parathyroid Hormone and Parathyroid Hormone-Related Peptide From Rat Osteoblast-Like Cells: A Single Receptor Stimulates Intracellular Accumulation of Both cAMP and Inositol Trisphosphates and Increases Intracellular Free Calcium," *Proc. Natl. Acad. Sci. USA.* 89: 2732-2736 (1992).
Abou-Samra et al., "Cyclic Adenosine 3', 5'-Monophosphate (cAMP)-Dependent and cAMP-Independent Regulation of Parathyroid Hormone Receptors on UMR 106-01 Osteoblastic Osteosarcoma Cells," *Endocrinology* 129: 2547-2554 (1991).
Abou-Samra et al., "Down-Regulation of Parathyroid (PTH)/PTH-Related Peptide Receptor Immunoreactivity and PTH Binding in Opossum Kidney Cells by PTH and Dexamethasone," *Endocrinology* 135: 2588-2594 (1994).
Abou-Samra et al., "Non-Homologous Sequences of Parathyroid Hormone and the Parathyroid Hormone Related Peptide Bind to a Common Receptor on ROS 17/2.8 Cells," *Endocrinology* 125: 2215-2217 (1989).

(Continued)

*Primary Examiner* — Shulamith H Shafer
(74) *Attorney, Agent, or Firm* — Clark & Elbing LLP

(57) ABSTRACT

The present invention is related to novel parathyroid hormone polypeptide derivatives, and to pharmaceutical composition containing the polypeptides, as well as synthetic and recombinant methods for producing the polypeptides. Also disclosed are methods for treating mammalian conditions characterized by decreases in bone mass using therapeutically effective pharmaceutical compositions containing the polypeptides of the present invention. The present invention further provides diagnostic and therapeutic methods using the polypeptide derivatives.

22 Claims, 8 Drawing Sheets

U.S. PATENT DOCUMENTS

Figure 2:
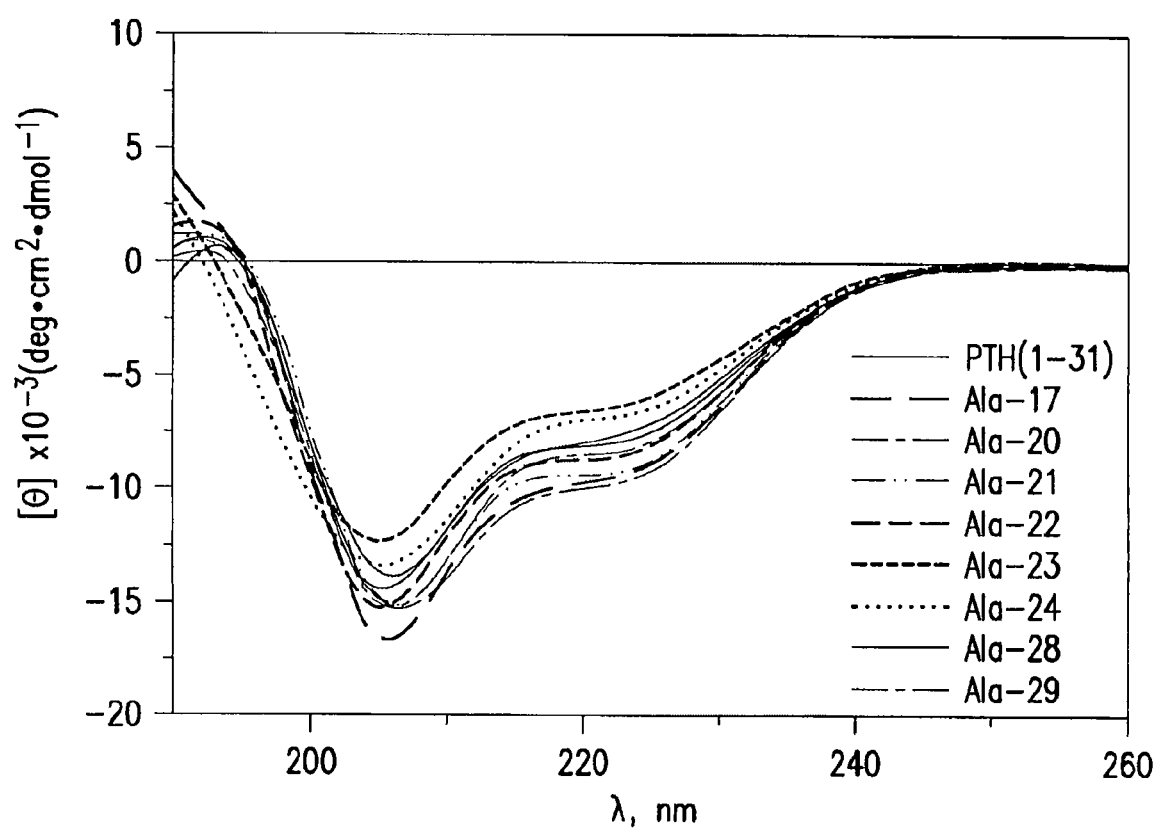
Figure 4A:
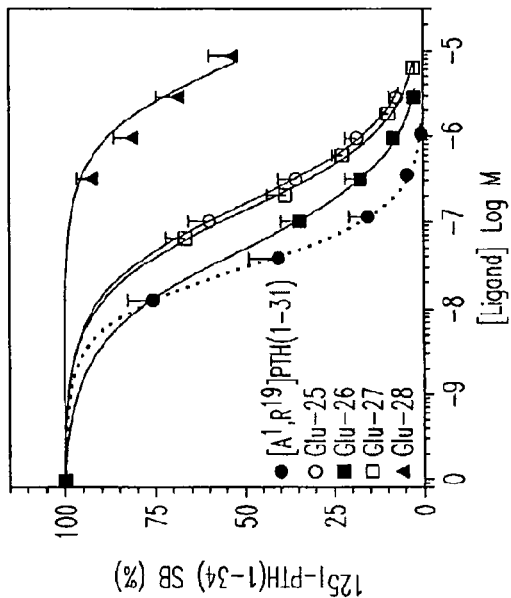
Figure 4B:
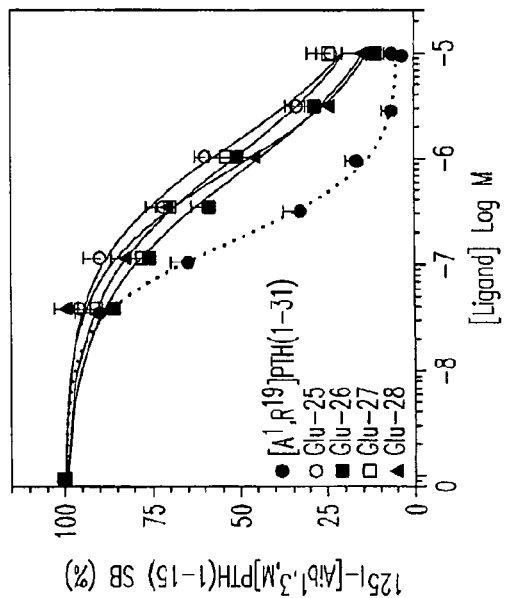
Figure 4C:
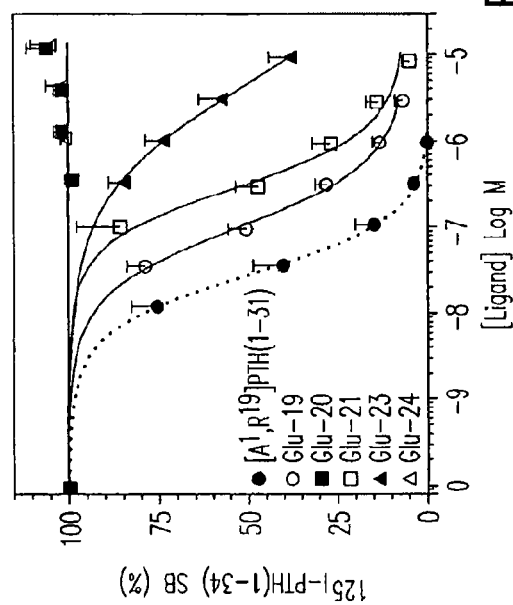
Figure 4D:
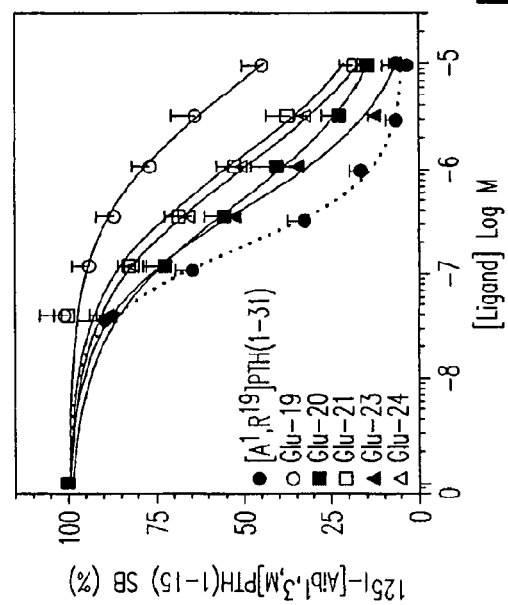

| | | | |
|---|---|---|---|
| 5,717,062 | A | 2/1998 | Chorev et al. |
| 5,723,218 | A | 3/1998 | Haugland et al. |
| 5,723,577 | A | 3/1998 | Dong |
| 5,741,486 | A | 4/1998 | Pathak et al. |
| 5,763,416 | A | 6/1998 | Bonadio et al. |
| 5,798,225 | A | 8/1998 | Krstenansky et al. |
| 5,807,823 | A | 9/1998 | Krstenansky et al. |
| 5,814,603 | A | 9/1998 | Oldenburg et al. |
| 5,821,225 | A | 10/1998 | Vickery |
| 5,836,905 | A | 11/1998 | Lemelson et al. |
| 5,840,690 | A | 11/1998 | Holick |
| 5,840,837 | A | 11/1998 | Krstenansky et al. |
| 5,840,853 | A | 11/1998 | Segre et al. |
| 5,854,004 | A | 12/1998 | Czernilofsky et al. |
| 5,871,486 | A | 2/1999 | Huebner et al. |
| 5,874,086 | A | 2/1999 | Krstenansky et al. |
| 5,880,093 | A | 3/1999 | Bagnoli |
| 5,886,148 | A | 3/1999 | Segre et al. |
| 5,917,123 | A | 6/1999 | McTiernan et al. |
| 5,922,927 | A | 7/1999 | Bujard et al. |
| 5,977,070 | A | 11/1999 | Piazza et al. |
| 6,030,790 | A | 2/2000 | Adermann et al. |
| 6,051,686 | A | 4/2000 | Krstenansky et al. |
| 6,066,618 | A | 5/2000 | Holick |
| 6,147,186 | A | 11/2000 | Gardella et al. |
| 6,183,974 | B1 | 2/2001 | Bringhurst et al. |
| 6,362,163 | B1 | 3/2002 | Gardella et al. |
| 6,417,333 | B1 | 7/2002 | Bringhurst et al. |
| 6,495,662 | B1 | 12/2002 | Gardella et al. |
| 6,537,965 | B1 | 3/2003 | Bringhurst et al. |
| 6,541,220 | B1 | 4/2003 | Jüppner et al. |
| 6,756,480 | B2 | 6/2004 | Kostenuik et al. |
| 6,803,213 | B2 | 10/2004 | Bringhurst et al. |
| 7,022,815 | B1 | 4/2006 | Gardella et al. |
| 7,033,773 | B1 | 4/2006 | Bringhurst et al. |
| 7,057,012 | B1 | 6/2006 | Gardella et al. |
| 7,078,487 | B2 | 7/2006 | Jüppner et al. |
| 7,132,260 | B2 | 11/2006 | Segre et al. |
| 7,150,974 | B1 | 12/2006 | Segre et al. |
| 7,153,951 | B2 | 12/2006 | Gardella et al. |
| 7,169,567 | B1 | 1/2007 | Gardella et al. |
| 7,244,834 | B2 | 7/2007 | Gardella et al. |
| 7,253,264 | B1 | 8/2007 | Lauffer et al. |
| 7,371,844 | B2 | 5/2008 | Gardella et al. |
| 7,479,478 | B2 | 1/2009 | Bringhurst et al. |
| 7,521,528 | B2 | 4/2009 | Gardella et al. |
| 7,572,765 | B2 | 8/2009 | Gardella |
| 2002/0110871 | A1 | 8/2002 | Zahradnik et al. |
| 2003/0144209 | A1 | 7/2003 | Bringhurst et al. |
| 2003/0162256 | A1 | 8/2003 | Juppner et al. |
| 2003/0166838 | A1 | 9/2003 | Gardella et al. |
| 2003/0171288 | A1 | 9/2003 | Stewart |
| 2004/0176285 | A1 | 9/2004 | Juppner et al. |
| 2005/0026839 | A1 | 2/2005 | Gardella |
| 2005/0124537 | A1 | 6/2005 | Kostenuik et al. |
| 2005/0203012 | A1 | 9/2005 | Bringhurst et al. |
| 2005/0282749 | A1 | 12/2005 | Henriksen et al. |
| 2006/0078559 | A1 | 4/2006 | Migeotte et al. |
| 2007/0111946 | A1 | 5/2007 | Gardella et al. |
| 2007/0161569 | A1 | 7/2007 | Gardella |
| 2007/0203071 | A1 | 8/2007 | Gardella |

FOREIGN PATENT DOCUMENTS

| | | |
|---|---|---|
| CA | 2126132 | 12/1995 |
| CA | 2126299 | 12/2000 |
| EP | 0 341 962 | 11/1989 |
| EP | 0 464 533 | 1/1992 |
| EP | 0 477 885 | 4/1992 |
| EP | 0 561 412 | 9/1993 |
| EP | 0 748 817 | 12/1996 |
| EP | 0 783 522 | 7/1997 |
| GB | 2 269 176 | 2/1994 |
| JP | 58-96052 | 6/1983 |
| JP | 59-204159 | 11/1984 |
| JP | 5-32696 | 2/1993 |
| JP | 9-157294 | 6/1997 |
| WO | WO 87/01130 | 2/1987 |
| WO | WO 91/05050 | 4/1991 |
| WO | WO 92/01810 | 2/1992 |
| WO | WO 92/17581 | 10/1992 |
| WO | WO 92/17602 | 10/1992 |
| WO | WO 93/06121 | 4/1993 |
| WO | WO 93/06846 | 4/1993 |
| WO | WO 93/09222 | 5/1993 |
| WO | WO 93/11257 | 6/1993 |
| WO | WO 94/02510 | 2/1994 |
| WO | WO 94/12650 | 6/1994 |
| WO | WO 95/02610 | 1/1995 |
| WO | WO 95/11988 | 5/1995 |
| WO | WO 96/03437 | 2/1996 |
| WO | WO 96/10041 | 4/1996 |
| WO | WO 96/19206 | 6/1996 |
| WO | WO 97/02834 | 1/1997 |
| WO | WO 98/05683 | 2/1998 |
| WO | WO 98/30590 | 7/1998 |
| WO | WO 99/18945 | 4/1999 |
| WO | WO 00/23594 | 4/2000 |
| WO | WO 00/31137 | 6/2000 |
| WO | WO 00/31266 | 6/2000 |
| WO | WO 00/32771 | 6/2000 |
| WO | WO 00/32775 | 6/2000 |
| WO | WO 00/39278 | 7/2000 |
| WO | WO 00/40698 | 7/2000 |
| WO | WO 01/23427 | 4/2001 |
| WO | WO 01/23521 | 4/2001 |
| WO | WO 03/009804 | 2/2003 |
| WO | WO 2004/067021 | 8/2004 |
| WO | WO 2004/093902 | 11/2004 |
| WO | WO 2005/009358 | 2/2005 |
| WO | WO 2008/019062 | 2/2008 |
| WO | WO 2009/017809 | 2/2009 |

OTHER PUBLICATIONS

Abou-Samra et al., "Phorbol 12-Myristate 13-Acetate and Vasopressin Potentiate the Effect of Corticotropin-Releasing Factor on Cyclic AMP Production in Rat Anterior Pituitary Cells. Mechanisms of Action," *J. Biol. Chem.* 262: 1129-1136 (1987).

Adams et al., "Probing the Bimolecular Interactions of Parathyroid Hormone and the Human Parathyroid Hormone/Parathyroid Hormone-Related Protein Receptor. 2. Cloning, Characterization, and Photoaffinity Labeling of the Recombinant Human Receptor," *Biochemistry* 34: 10553-10559 (1995).

Alberts et al. "Chapter 6: Basic Genetic Mechanisms" in: *Molecular Biology of the Cell*, 3rd Edition, pp. 234-237 and the Genetic Code Table (Garland Pub., New York, NY, 1994).

Azarani et al., "Structurally Diverse N-terminal Peptides of Parathyroid Hormone (PTH) and PTH-Related Peptide (PTHRP) Inhibit the Na+/H+ Exchanger NHE3 Isoform by Binding to the PTH/PTHRP Receptor Type I and Activating Distinct Signaling Pathways," *J. Biol. Chem.* 271: 14931-14936 (1996).

Azarani et al., "Parathyroid Hormone and Parathyroid Hormone-Related Peptide Activate the Na+ /H+ Exchanger NHE-1 Isoform in Osteoblastic Cells (UMR-106) via a cAMP-dependent Pathway," *J. Biol. Chem.* 270: 23166-23172 (1995).

Barbier et al., "Bioactivities and Secondary Structures of Constrained Analogues of Human Parathyroid Hormone: Cyclic Lactams of the Receptor Binding Region," *J. Med. Chem.* 40:1373-1380 (1997).

Barbier et al., "Backbone-Methylated Analogues of the Principle Receptor Binding Region of Human Parathyroid Hormone. Evidence for Binding to Both the N-Terminal Extracellular Domain and Extracellular Loop Region," *J. Biol. Chem.* 280: 23771-23777 (2005).

Barbier et al., "Structural Requirements for Conserved Arginine of Parathyroid Hormone," *Biochemistry* 40: 8955-8961 (2001).

Barden et al., "Stabilized NMR Structure of the Hypercalcemia of Malignancy Peptide PTHrP[Ala-26](1-34)Amide," *Biochim. Biophys. Acta* 1208: 256-262 (1994).

Barden et al., "NMR Solution Structure of Human Parathyroid Hormone(1-34)," *Biochemistry* 32:7126-7132 (1993).

Barden et al., "NMR Study of a 34-Residue N-Terminal Fragment of a Parathyroid Hormon-Related Protein Secreted During Humoral Hypercalcemia of Malignancy," *Eur. J. Biochem.* 184: 379-394 (1989).

Becker et al., "Procedure Guideline for Thyroid Scintigraphy: 1.0. Society of Nuclear Medicine," *J. Nucl. Med.* 37: 1264-1266 (1996).

Behar et al., "Histidine at Position 5 is the Specificity "Switch" between Two Parathyroid Hormone Receptor Subtypes," *Endocrinology* 137: 4217-4224 (1996).

Behar et al., "Photoaffinity Cross-Linking Identifies Differences in the Interactions of an Agonist and an Antagonist with the Parathyroid Hormone/Parathyroid Hormone-Related Protein Receptor," *J. Biol. Chem.* 275: 9-17 (2000).

Bergwitz et al., "Identification, Functional Characterization, and Developmental Expression of Two Nonallelic Parathyroid Hormone (PTH)/PTH-Related Peptide Receptor Isoforms in *Xenopus laevis* (Daudin)," *Endocrinology* 139: 723-732 (1998).

Bergwitz et al., "Full Activation of Chimeric Receptors by Hybrids between Parathyroid Hormone and Calcitonin. Evidence for a Common Pattern of Ligand-Receptor Interaction," *J. Biol. Chem.* 271: 26469-26472 (1996).

Bergwitz et al., "Residues in the Membrane-spanning and Extracellular Loop Regions of the Parathyroid Hormone (PTH)-2 Receptor Determine Signaling Selectivity for PTH and PTH-Related Peptide," *J. Biol. Chem.* 272: 28861-28868 (1997).

Berlot, "A Highly Effective Dominant Negative Alpha s Construct Containing Mutations that Affect Distinct Functions Inhibits Multiple Gs-Coupled Receptor Signaling Pathways," *J. Biol. Chem.* 277: 21080-21085 (2002).

Berridge et al., "Changes in the Levels of Inositol Phosphates after Agonist-Dependent Hydrolysis of Membrane Phosphoinositides," *Biochem. J.* 212: 473-482 (1983).

Bettoun et al., "Cloning and Characterization of the Promoter Regions of the Human Parathyroid Hormone (PTH)/PTH-Related Peptide Receptor Gene: Analysis of Deoxyribonucleic Acid from Normal Subjects and Patients with Pseudohypoparathyroidism Type 1b," *J. Clin. Endocrinol. Metab.* 82: 1031-1040 (1997).

Bettoun et al., "Developmental Upregulation of Human Parathyroid Hormone (PTH)/PTH-Related Peptide Receptor Gene Expression from Conserved and Human-specific Promoters," *J. Clin. Invest.* 102: 958-967 (1998).

Bisello et al., "Parathyroid Hormone-Receptor Interactions Identified Directly by Photocross-Linking and Molecular Modeling Studies," *J. Biol. Chem.* 273: 22498-22505 (1998).

Bisello et al., "Selective Ligand-Induced Stabilization of Active and Desensitized Parathyroid Hormone Type 1 Receptor Conformations," *J. Biol. Chem.* 277: 38524-38530 (2002).

Bork, "Powers and Pitfalls in Sequence Analysis: The 70% Hurdle," Genome Res. 10: 398-400 (2000).

Bork et al., "Go Hunting in Sequence Databases but Watch Out for the Traps," Trends Genet. 12: 425-427 (1996).

Born et al., "Inhibition of Parathyroid Hormone Bioactivity by Human Parathyroid Hormone (PTH)-(3-84) and PTH-(8-84) Synthesized in *Escherichia coli*," *Endocrinology* 123:1848-1853 (1988).

Bos et al., "Expression of the Parathyroid Hormone Receptor and Correlation with Other Osteoblastic Parameters in Fetal Rat Osteoblasts," *Calcif. Tisse Int.* 58:95-100 (1996).

Brenner, "Errors in Genome Annotation," *Trends Genet.* 15: 132-133 (1999).

Bringhurst et al., "Cloned, Stably Expressed Parathyroid Hormone (PTH)/PTH-Related Peptide Receptors Activate Multiple Messenger Signals and Biological Responses in LLC-PK1 Kidney Cells," *Endocrinology* 132: 2090-2098 (1993).

Broadus et al., "Parathyroid Hormone-Related Protein: Structure, Processing, and Physiological Actions," in: *The Parathyroids* (eds. J. P. Bilezikan et al.), pp. 259-294 (Raven Press Ltd., New York, NY, 1994).

Bryant et al., "Helix-Inducing α-Aminoisobutyric Acid in Opioid Mimetic Deltorphin C Analogues," *J. Med. Chem.* 40: 2579-2587 (1997).

Bundi et al., "Characterisation of a Local Structure in the Synthetic Parathyroid Hormone Fragment 1-34 by 1H Nuclear-Magnetic-Resonance Techniques," *Eur. J. Biochem.* 91: 201-208 (1978).

Campbell et al., "Totipotency or Multipotentiality of Cultured Cells: Applications and Progress," *Theriogenology* 47: 63-72 (1997).

Carter et al., "Zinc(II)-Mediated Enhancement of the Agonist Activity of Histidine-Substituted Parathyroid Hormone (1-14) Analogues," *Biochem. Biophys. Acta* 1538: 290-304 (2001).

Carter et al., "Studies of the N-Terminal Region of a Parathyroid Hormone-Related Peptide(1-36) Analog: Receptor Subtype-Selective Agonists, Antagonists, and Photochemical Cross-Linking Agents," *Endocrinology* 140: 4972-4981 (1999).

Castro et al., "Dual Regulation of the Parathyroid Hormone (PTH)/PTH-Related Peptide Receptor Signaling by Protein Kinase C and Beta-Arrestins," *Endocrinology* 143: 3854-3865 (2002).

Castro et al., "Turn-On Switch in Parathyroid Hormone Receptor by a Two-Step Parathyroid Hormone Binding Mechanism," *Proc. Natl. Acad. Sci. USA* 102: 16084-16089 (2005).

Catanzariti et al., "A Novel Expression System for Gs-Coupled Receptors," *BioTechniques* 15: 474-479 (1993).

Caulfield et al., "The Bovine Renal Parathyroid Hormone (PTH) Receptor has Equal Affinity for Two Different Amino Acid Sequences: The Receptor Binding Domains of PTH and PTH-related Protein are Located within the 14-34 Region," *Endocrinology* 127: 83-87 (1990).

Caulfield et al., "Parathyroid Hormone-Receptor Interactions," *Trends Endocrinol. Metab.* 1: 164-168 (1990).

Cervini et al., "Human Growth Hormone-Releasing hGHRH(1-29)-NH2: Systematic Structure-Activity Relationship Studies," *J. Med. Chem.* 41: 717-727 (1998).

Chakrabartty, "Large Differences in the Helix Propensities of Alanine and Glycine," *Nature* 351: 586-588 (1991).

Chakravarthy et al., "Parathyroid Hormone Fragment [3-34] Stimulates Protein Kinase C (PKC) Activity in Rat Osteosarcoma and Murine T-lymphoma Cells," *Biochem. Biophys. Res. Commun.* 171: 1105-1110 (1990).

Chauvin et al., "Parathyroid Hormone Receptor Recycling: Role of Receptor Dephosphorylation and Beta-Arrestin," *Mol. Endocrinol.* 16: 2720-2732 (2002).

Chen, et al.,"Solution Structure of the Osteogenic 1-31 Fragment of Human Parathyroid Hormone," *Biochemistry* 39: 12766-12777 (2000).

Chorev et al., "Cyclic Parathyroid Hormone Related Protein Antagonists: Lysine 13 to Aspartic Acid 17 [i to (i +4)] Side Chain to Side Chain Lactamization," *Biochemistry* 30: 5968-5974 (1991).

Chorev et al., "Modifications of Position 12 in Parathyroid Hormone and Parathyroid Hormone Related Protein: Toward the Design of Highly Potent Antagonists," *Biochemistry* 29:1580-1586 (1990).

Chu et al, "Porcine Proparathyroid Hormone. Identification, Biosynthesis, and Partial Amino Acid Sequence," *Biochemistry* 14: 3631-3635 (1975).

Civitelli et al., "PTH Elevates Inositol Polyphosphates and Diacylglycerol in a Rat Osteoblast-Like Cell Line," *Am. J. Physiol.* 255: E660-667 (1988).

Civitelli et al., "Parathyroid Hormone-Related Peptide Transiently Increases Cytosolic Calcium in Osteoblast-Like Cells: Comparison with Parathyroid Hormone," *Endocrinology* 125: 1204-1210 (1989).

Cohen et al., "Analogues of Parathyroid Hormone Modified at Positions 3 and 6. Effects on Receptor Binding and Activation of Adenylyl Cyclase in Kidney and Bone," *J. Biol. Chem.* 266: 1997-2004 (1991).

Cole et al., "Regulation of Sodium-Dependent Phosphate Transport by Parathyroid Hormone in Opossum Kidney Cells: Adenosine 3', 5'-Monophosphate-Dependent and -Independent Mechanisms," *Endocrinology* 122: 2981-2989 (1988).

Colquhoun, "Binding, Gating, Affinity, and Efficacy: The Interpretation of Structure-Activity Relationships for Agonists and of the Effects of Mutating Receptors," *Br. J. Pharmacol.* 125: 924-947 (1998).

Condon et al., "The Bioactive Conformation of Human Parathyroid Hormone. Structural Evidence for the Extended Helix Postulate," *J. Am. Chem. Soc.*122: 3007-3014 (2000).

Cwirla et al., "Peptide Agonist of the Thrombopoietin Receptor as Potent as the Natural Cytokine," *Science* 276: 1696-1699 (1997).

Dang et al., "Gene Therapy and Translational Cancer Research," *Clin. Cancer Res.* 5: 471-474 (1999).

Dautzenberg et al., "Mapping of the Ligand-Selective Domain of the *Xenopus laevis* Corticotropin-Releasing Factor Receptor 1: Implications for the Ligand-Binding Site," *Proc. Natl. Acad. Sci. USA* 95: 4941-4946 (1998).
DeAlmeida et al., "Identification of Binding Domains of the Growth Hormone-Releasing Hormone Receptor by Analysis of Mutant and Chimeric Receptor Proteins," *Mol. Endocrinol.* 12: 750-765 (1998).
Dean et al., "Mechanisms of Ligand Binding to the Parathyroid Hormone (PTH)/PTH-Related Protein Receptor: Selectivity of a Modified PTH(1-15) Radioligand for GalphaS-Coupled Receptor Conformations," *Mol. Endocrinol.* 20: 931-943 (2006).
Dempster et al., "Erratum: Anabolic Actions of Parathyroid Hormone on Bone," *Endocrine Rev.* 15:261 (1994).
Dempster et al., "Anabolic Actions of Parathyroid Hormone on Bone," *Endocrine Rev.* 14: 690-709 (1993).
Dempster et al., "On the Mechanism of Cancellous Bone Preservation in Postmenopausal Women with Mild Primary Hyperparathyroidism," *J. Clin. Endocrinol. Metab.* 84: 1562-1566 (1999).
Ding et al., "A Single Amino Acid Determines the Immunostimulatory Activity of Interleukin 10," *J. Exp. Med.* 191:213-223 (2000).
Doerks et al., "Protein Annotation: Detective Work for Function Prediction," *Trends Genet.* 14: 248-250 (1998).
Dohlman et al., "Model Systems for the Study of Seven-Transmembrane-Segment Receptors," *Annu. Rev. Biochem.* 60: 653-688 (1991).
Donahue et al., "Differential Effects of Parathyroid Hormone and Its Analogues on Cytosolic Calcium Ion and cAMP Levels in Cultured Rat Osteoblast-Like Cells," *J. Biol. Chem.* 263: 13522-13527 (1988).
Dong et al., "Demonstration of a Direct Interaction between Residue 22 in the Carboxyl-Terminal Half of Secretin and the Amino-Terminal Tail of the Secretin Receptor Using Photoaffinity Labeling," *J. Biol. Chem.* 274: 903-909 (1999).
Dunlay et al., "PTH Receptor Coupling to Phospholipase C is an Alternate Pathway of Signal Transduction in Bone and Kidney," *Am. J. Physiol.* 258: F223-F231 (1990).
Ebert et al., "'A Moloney MLV-Rat Somatotropin Fusion Gene Produces Biologically Active Somatotropin in a Transgenic Pig," *Mol. Endocrinol.* 2: 277-283 (1988).
Epand, "Relationships Among Several Different Non-Homologous Polypeptide Hormones," *Mol. Cell Biochem.* 57: 41-47 (1983).
Fairwell et al., "Total Solid-Phase Synthesis, Purification, and Characterization of Human Parathyroid Hormone-(1-84)," *Biochemistry* 22: 2691-2697 (1983).
Fischer et al., "Human Parathyroid Hormone. Immunological Characterization of Antibodies Against a Glandular Extract and the Synthetic Amino-Terminal Fragments 1-12 and 1-34 and their Use in the Determination of Immunoreactive Hormone in Human Sera," *J. Clin. Invest.* 54: 1382-1394 (1974).
Freyaldenhoven et al., "Protein Kinase C Differentially Modulates PTH- and PGE2-Sensitive Adenylate Cyclase in Osteoblast-Like Cells," *Am. J. Physiol.* 262: E87-E95 (1992).
Fujimori et al., "Structure-Function Relationship of Parathyroid Hormone: Activation of Phospholipase-C, Protein Kinase-A and -C in Osteosarcoma Cells," *Endocrinology* 130: 29-36 (1992).
Fujimori et al., "Dissociation of Second Messenger Activation by Parathyroid Hormone Fragments in Osteosarcoma Cells," *Endocrinology* 128: 3032-3039 (1991).
Fukayama et al., "Mechanisms of Desensitization to Parathyroid Hormone in Human Osteoblast-Like SaOS-2 Cells," *Endocrinology* 131: 1757-1769 (1992).
Fukayama et al., "Role of Protein Kinase-A in Homologous Down-Regulation of Parathyroid Hormone (PTH)/PTH-Related Peptide Receptor Messenger Ribonucleic Acid in Human Osteoblast-Like SaOS-2 Cells," *Endocrinology* 134: 1851-1858 (1994).
Gaich et al., "Amino-Terminal Parathyroid Hormone-Related Protein: Specific Binding and Cytosolic Calcium Responses in Rat Insulinoma Cells," *Endocrinology* 132: 1402-1409 (1993).
Gardella et al., "Analysis of Parathyroid Hormone's Principal Receptor-Binding Region by Site-Directed Mutagenesis and Analog Design," *Endocrinology* 132: 2024-2030 (1993).
Gardella et al., "Converting Parathyroid Hormone-Related Peptide (PTHrP) into a Potent PTH-2 Receptor Agonist," *J. Biol. Chem.* 271: 19888-19893 (1996).
Gardella et al., "Determinants of [Arg2]PTH-(1-34) Binding and Signaling in the Transmembrane Region of the Parathyroid Hormone Receptor," *Endocrinology* 135: 1186-1194 (1994).
Gardella et al., "Expression of Human Parathyroid Hormone-(1-84) in *Escherichia coli* as a Factor X-cleavable Fusion Protein," *J. Biol. Chem.* 265: 15854-15859 (1990).
Gardella et al., "Mutational Analysis of the Receptor-Activating Region of Human Parathyroid Hormone," *J. Biol. Chem.* 266: 13141-13146 (1991).
Gardella et al., "Parathyroid Hormone (PTH)-PTH-Related Peptide Hybrid Peptides Reveal Functional Interactions Between the 1-14 and 15-34 Domains of the Ligand," *J. Biol. Chem.* 270: 6584-6588 (1995).
Gardella et al., "Scanning Mutagenesis of the 23-35 Region of Parathyroid Hormone Reveals Important Determinants of Receptor Binding," in: *Calcium Regulating Hormones and Bone Metabolism: Basic and Clinical Aspects* (eds. D.V. Cohn et al.), vol. 11, pp. 218-222 (Excerpta Medica, Amsterdam, 1992).
Gardella at al., "Transmembrane Residues of the Parathyroid Hormone (PTH)/PTH-Related Peptide Receptor that Specifically Affect Binding and Signaling by Agonist Ligands," *J. Biol. Chem.* 271: 12820-12825 (1996).
Gensure et al., "Identification of a Contact Site for Residue 19 of Parathyroid Hormone (PTH) and PTH-Related Protein Analogs in Transmembrane Domain Two of the Type 1 PTH Receptor," *Mol Endocrinol.* 17: 2647-2658 (2003).
Gensure et al., "Parathyroid Hormone and Parathyroid Hormone-Related Peptide, and their Receptors," *Biochem. Biophys. Res. Commun.* 328: 666-678 (2005).
Gensure et al., "Multiple Sites of Contact between the Carboxyl-Terminal Binding Domain of PTHrP-(1-36) Analogs and the Amino-Terminal Extracellular Domain of the PTH/PTHrP Receptor Identified by Photoaffinity Cross-Linking," *J. Biol. Chem.* 276: 28650-28658 (2001).
Goltzman et al., "Influence of Guanyl Nucleotides on Parathyroid Hormone-Stimulated Adenylyl Cyclase Activity in Renal Cortical Membranes," *Endocrinology* 103: 1352-1360 (1978).
Goltzmann et al., "Analysis of the Requirements for Parathyroid Hormone Action in Renal Membranes with the Use of Inhibiting Analogues," *J. Biol. Chem.* 250: 3199-3203 (1975).
Gombert et al., "Alanine and D-Amino Acid Scan of Human Parathyroid Hormone," in: *Peptides: Chemistry, Structure and Biology* (eds. P.T.P. Kaumaya et al.), pp. 661-662 (Mayflower Sci. Ltd., England, 1996).
Goud et al., "Solid-Phase Synthesis and Biologic Activity of Human Parathyroid Hormone (1-84)," *J. Bone Miner. Res.* 6: 781-789 (1991).
Grace et al., "NMR Structure and Peptide Hormone Binding Site of the First Extracellular Domain of a Type B1 G Protein-Coupled Receptor," *Proc. Natl. Acad. Sci. USA* 101: 12836-41 (2004).
Greenberg et al. "Mapping the Bimolecular Interface of the Parathyroid Hormone (PTH)-PTH1 Receptor Complex: Spatial Proximity between Lys(27) (of the Hormone Principal Binding Domain) and Leu(261) (of the First Extracellular Loop) of the Human PTH1 Receptor," *Biochemistry* 39: 8142-8152 (2000).
Gronwald et al., "Structure of Recombinant Human Parathyroid Hormone Solution Using Multidimensional NMR Spectroscopy," *Biol. Chem. Hoppe-Seyler* 377: 175-186 (1996).
Guo et al., "Parathyroid Hormone (PTH)/PTH-Related Peptide Receptor Density Modulates Activation of Phospholipase C and Phosphate Transport by PTH in LLC-PK1 Cells," *Endocrinology* 136: 3884-3891 (1995).
Habashita et al., "Synthesis and Biological Activities of hPTH(1-34) Analogues: Modification of the Middle Part and C-terminal Alkylamides," in: *Peptide Science—Present and Future: Proceedings of the 1st International Peptide Symposium* (ed. Y. Shimonishi), pp. 711-713 (Kluwer Acad. Pub., Great Britain, 1997).
Hammer et al., "Genetic Engineering of Mammalian Embryos," *J. Anim. Sci.* 63: 269-278 (1986).

Heinrich et al., "Gene Encoding Parathyroid Hormone. Nucleotide Sequence of the Rat Gene and Deduced Amino Acid Sequence of Rat Preproparathyroid Hormone," *J. Biol. Chem.* 259: 3320-3329 (1984).

Heinrich et al., "Rat Parathyroid Hormone Gene, Exons II and III," Alignment result 8, SEQ ID No. 1, Database: GenEmbl, Accession No. K01268 (Apr. 27, 1993).

Hilliker et al., "Truncation of the Amino Terminus of PTH Alters Its Anabolic Activity on Bone in Vivo," *Bone* 19: 469-477 (1996).

Hjorth et al., "Constitutive Activity of Glucagon Receptor Mutants," *Mol. Endocrinol.* 12:78-86 (1998).

Hoare et al., "Measurement of Agonist and Antagonist Ligand-Binding Parameters at the Human Parathyroid Hormone Type 1 Receptor: Evaluation of Receptor States and Modulation by Guanine Nucleotide," *J. Pharmacol. Exp. Ther.* 289: 1323-1333 (1999).

Hoare et al., "Evaluating the Signal Transduction Mechanism of the Parathyroid Hormone 1 Receptor," *J. Biol. Chem.* 276: 7741-7753 (2001).

Holtmann et al., "Critical Contributions of Amino-terminal Extracellular Domains in Agonist Binding and Activation of Secretin and Vasoactive Intestinal Polypeptide Receptors. Studies of Chimeric Receptors," *J. Biol. Chem.* 270: 14394-14398 (1995).

Holtmann et al., "Molecular Basis and Species Specificity of High Affinity Binding of Vasoactive Intestinal Polypeptide by the Rat Secretin Receptor. Effec of Receptor-G-Protein Interaction on the Ligand Binding Mechanism and Receptor Conformation," *J. Pharmacol. Exp. Ther.* 279: 555-560 (1996).

Horiuchi et al., "A Parathyroid Hormone Inhibitor In Vivo: Design and Biological Evaluation of a Hormone Analog," *Science* 220: 1053-1055 (1983).

Horiuchi et al., "Evaluation of a Parathyroid Hormone Antagonist in an in Vivo Multiparameter Bioassay," *Am. J. Physiol.* 253: E187-192 (1987).

Hruska et al., "Stimulation of Inositol Trisphosphate and Diacylglycerol Production in Renal Tubular Cells by Parathyroid Hormone," *J. Clin. Invest.* 79: 230-239 (1987).

Iida-Klein et al., "Structural Requirements of Parathyroid Hormone/Parathyroid Hormone-Related Peptide Receptors for Phospholipase C Activation and Regulation of Phosphate Uptake," *Miner. Electrolyte Metab.* 21: 177-179 (1995).

Iida-Klein et al., "Mutations in the Second Cytoplasmic Loop of the Rat Parathyroid Hormone (PTH)/PTH-Related Protein Receptor Result in Selective Loss of PTH-stimulated Phospholipase C Activity," *J. Biol. Chem.* 272: 6882-6889 (1997).

Iida-Klein et al., "Truncation of the Carboxyl-terminal Region of the Rat Parathyroid Hormone (PTH)/PTH-Related Peptide Receptor Enhances PTH Stimulation of Adenylyl Cyclase but Not Phospholipase C," *J. Biol. Chem.* 270: 8458-8465 (1995).

Inomata et al., "Characterization of a Novel Parathyroid Hormone (PTH) Receptor with Specificity for the Carboxyl-Terminal Region of PTH-(1-84)," *Endocrinology* 136: 4732-4740 (1995).

Ishihara et al., "Molecular Cloning and Expression of a cDNA Encoding the Secretin Receptor," *EMBO J.* 10: 1635-1641 (1991).

Iwakura et al., "Effects of the Length of a Glycine Linker Connecting the N-and C-Termini of a Circularly Permuted Dihydrofolate Reductase," *Protein Eng.* 11: 707-713 (1998).

Jans et al., "LLC-PK1 Cell Mutants in cAMP Metabolism Respond Normally to Phorbol Esters," *FEBS Lett.* 205: 127-131 (1986).

Janulis et al., "Structure-Function Requirements of Parathyroid Hormone for Stimulation of 1,25-Dihydroxyvitamin D3 Production by Rat Renal Proximal Tubules," *Endocrinology* 133: 713-719 (1993).

Ji et al., "Human Choriogonadotropin Binds to a Lutropin Receptor with Essentially No N-terminal Extension and Stimulates cAMP Synthesis," *J. Biol. Chem.* 266: 13076-13079 (1991).

Jin et al., "Crystal Structure of Human Parathyroid Hormone 1-34 at 0.9-A Resolution," *J. Biol. Chem.* 275: 27238-27244 (2000).

Jing et al., "GDNF-Induced Activation of the Ret Protein Tyrosine Kinase Is Mediated by GDNFR-alpha, a Novel Receptor for GDNF," *Cell* 85: 1113-1124 (1996).

Jobert et al., "Parathyroid Hormone-Induced Calcium Release from Intracellular Stores in a Human Kidney Cell Line in the Absence of Stimulation of Cyclic Adenosine 3',5'-Monophosphate Production," *Endocrinology* 138: 5282-5292 (1997).

Jouishomme et al., "Further Definition of the Protein Kinase C Activation Domain of the Parathyroid Hormone," *J. Bone Miner. Res.* 9: 943-949 (1994).

Jouishomme et al., "The Protein Kinase-C Activation Domain of the Parathyroid Hormone," *Endocrinology* 130: 53-60 (1992).

Joun et al., "Tissue-specific Transcription Start Sites and Alternative Splicing of the Parathyroid Hormone (PTH)/PTH-related Peptide (PTHrP) Receptor Gene: A New PTH/PTHrP Receptor Splice Variant that Lacks the Signal Peptide," *Endocrinology* 138: 1742-1749 (1997).

Jüppner et al., "A G Protein-linked Receptor for Parathyroid Hormone and Parathyroid Hormone-Related Peptide," *Science* 254: 1024-1026 (1991).

Jüppner et al., "Properties of Amino-Terminal Parathyroid Hormone-Related Peptides Modified at Positions 11-13," *Peptides* 11: 1139-1142 (1990).

Juppner et al., "The Extracellular Amino-Terminal Region of the Parathyroid Hormone (PTH)/PTH-related Peptide Receptor Determines the Binding Affinity for Carboxyl-Terminal Fragments of PTH-(1-34)," *Endocrinology* 134: 879-884 (1994).

Jüppner et al., "The Parathyroid Hormone-Like Peptide Associated with Humoral Hypercalcemia of Malignancy and Parathyroid Hormone Bind to the Same Receptor on the Plasma Membrane of ROS 17/2.8 Cells," *J. Biol. Chem.* 263: 8557-8560 (1988).

Kappel et al., "Regulating Gene Expression in Transgenic Animals," *Curr. Op. Biotechnol.* 3: 548-553 (1992).

Karaplis et al., "Lethal Skeletal Dysplasia From Targeted Disruption of the Parathyroid Hormone-Related Peptide Gene," *Genes Dev.* 8: 277-289 (1994).

Kaufman et al., "Transgenic Analysis of a 100-kb Human Beta-Globin Cluster-Containing DNA Fragment Propagated as a Bacterial Artificial Chromosome," *Blood* 94: 3178-3184 (1999).

Kaufmann et al., "Functional Expression of a Stably Transfected Parathyroid Hormone/Parathyroid Hormone Related Protein Receptor Complementary DNA in CHO cells," *Mol. Cell. Endocrinol.* 104: 21-27 (1994).

Kaul et al., "Stereochemical Control of Peptide Folding," *Bioorg. Med. Chem.* 7: 105-117 (1999).

Kemp et al., "Parathyroid Hormone-Related Protein of Malignancy: Active Synthetic Fragments," *Science* 238: 1568-1570 (1987).

Kimura et al., "Strategy for the Synthesis of Large Peptides: An Application to the Total Synthesis of Human Parathyroid Hormone [hPTH)1-84)]," *Biopolymers* 20: 1823-1832 (1981).

Kimura et al., "Discovery of a Novel Thrombopoietin Mimic Agonist Peptide," *J. Biochem.* 122: 1046-1051 (1997).

Klaus et al., "Investigation of the Solution Structure of the Human Parathyroid Hormone Fragment (1-34) by 1H NMR Spectroscopy, Distance Geometry, and Molecular Dynamics Calculations," *Biochemistry* 30: 6936-6942 (1991).

Kolakowski, "GCRDb: A G-Protein-Coupled Receptor Database," *Receptors and Channels* 2: 1-7 (1994).

Kong et al., "The Rat, Mouse and Human Genes Encoding the Receptor for Parathyroid Hormone and Parathyroid Hormone-Related Peptide are Highly Homologous," *Biochem. Biophys. Res. Commun.* 200: 1290-1299 (1994).

Kovacs et al., "Parathyroid Hormone-Related Peptide (PTHrP) Regulates Fetal-placental Calcium Transport Through a Receptor Distinct from the PTH/PTHrP Receptor," *Proc. Natl. Acad. Sci. USA* 93: 15233-15238 (1996).

Kronenberg et al., "Parathyroid Hormone: Biosynthesis, Secretion, Chemistry, and Action," in: *Handbook of Experimental Pharmacology* (eds. G.R. Mundy et al.), pp. 507-567 (Springer-Verlag, Heidelberg, Germany, 1993).

Kronenberg et al., "The PTH/PTHrP Receptor: One Receptor for Two Ligands," in: *Molecular Genetics of Endocrine Disorders* (ed. R.V. Thakker), pp. 389-420 (Chapman & Hall, New York, NY, 1997).

Lanske et al., "PTH/PTHrP Receptor in Early Development and Indian Hedgehog-Regulated Bone Growth," *Science* 273: 663-666 (1996).

Lee et al., "Homolog-scanning Mutagenesis of the Parathyroid Hormone (PTH) Receptor Reveals PTH-(1-34) Binding Determinants in the Third Extracellular Loop," *Mol. Endocrinol.* 9: 1269-1278 (1995).

Lee et al., "Role of the Extracellular Regions of the Parathyroid Hormone (PTH)/PTH-Related Peptide Receptor in Hormone Binding," *Endocrinology* 135: 1488-1495 (1994).

Li et al., "Minimization of a Polypeptide Hormone," *Science* 270: 1657-1660 (1995).

Lin et al., "Expression Cloning of an Adenylate Cyclase-Coupled Calcitonin Receptor," *Science* 254: 1022-1024 (1991).

Livnah et al., "Functional Mimicry of a Protein Hormone by a Peptide Agonist: The EPO Receptor Complex at 2.8 A," *Science* 273: 464-471 (1996).

Luck et al., "The (1-14) Fragment of Parathyroid Hormone (PTH) Activates Intact and Amino-terminally Truncated PTH-1 Receptors," *Mol. Endocrinol.* 13: 670-680 (1999).

Majeska et al., "Parathyroid Hormone-Responsive Clonal Cell Lines from Rat Osteosarcoma," *Endocrinology* 107: 1494-1503 (1980).

Mannstadt et al., "Evidence for a Ligand Interaction Site at the Amino-terminus of the Parathyroid Hormone (PTH)/PTH-related Protein Receptor from Cross-Linking and Mutational Studies," *J. Biol. Chem.* 273: 16890-16896 (1998).

Marx et al., "Solution Structures of Human Parathyroid Hormone Fragments hPTH(1-34) and hPTH (1-3 9) and Bovine Parathyroid Hormone Fragment bPTH(1-37)," *Biochem. Biophys. Res. Commun.* 267: 213-220 (2000).

Marx et al., "Structure of Human Parathyroid Hormone 1-37 in Solution," *J. Biol. Chem.* 270: 15194-15202 (1995).

Marx et al., "Structure-Activity Relation of NH2-terminal Human Parathyroid Hormone Fragments," *J. Biol. Chem.* 273: 4308-4316 (1998).

Matsumoto et al., "Daily Nasal Spray of hPTH(1-34) for 3 Months Increases Bone Mass in Osteoporotic Subjects: A Pilot Study," *Osteoporos. Int.* 17: 1532-1538 (2006).

McCuaig et al., "Molecular Cloning of the Gene Encoding the Mouse Parathyroid Hormone/Parathyroid Hormone-Related Peptide Receptor," *Proc. Natl. Acad. Sci. USA* 91: 5051-5055 (1994).

Menniti et al., "Different Modes of Regulation for Receptors Activating Phospholipase C in the Rat Pancreatoma Cell Line AR4-2J," *Mol. Pharmacol.* 40: 727-733 (1991).

Mickle et al., "Genotype-Phenotype Relationships in Cystic Fibrosis," *Med. Clin. North Am.* 84: 597-607 (2000).

Mikayama et al., "Molecular Cloning and Functional Expression of a cDNA Encoding Glycosylation-Inhibiting Factor," *Proc. Natl. Acad. Sci USA* 90: 10056-10060 (1993).

Mitchell et al., "Mechanisms of Homologous and Heterologous Regulation of Parathyroid Hormone Receptors in the Rat Osteosarcoma Cell Line UMR-106," *Endocrinology* 126: 2650-2660 (1990).

Moretto et al., "(αMe)Nva: Stereoselective Syntheses and Preferred Conformations of Selected Model Peptides," *J. Pept. Res.* 56: 283-297 (2000).

Mullins et al., "Perspective series: Molecular medicine in genetically engineered animals," *J. Clin. Invest.* 98:S37-S40 (1996).

Murray et al., "Dexamethasone-Treated ROS 17/2.8 Rat Osteosarcoma Cells are Responsive to Human Carboxylterminal Parathyroid Hormone Peptide hPTH (53-84): Stimulation of Alkaline Phosphatase," *Calcif. Tissue Int.* 49: 120-123 (1991).

Musso et al. "Renal Vasodilatation and Microvessel Adenylate Cyclase Stimulation by Synthetic Parathyroid Hormone-Like Protein Fragments," *Eur. J. Pharmacol.* 174: 139-151 (1989).

Nakamoto et al., "Probing the Bimolecular Interactions of Parathyroid Hormone with the Human Parathyroid Hormone/Parathyroid Hormone-Related Protein Receptor. 1. Design, Synthesis and Characterization of Photoreactive Benzophenone-Containing Analogs of Parathyroid Hormone," *Biochemistry* 34: 10546-10552 (1995).

Nakamura et al., "Action of Fragments of Human Parathyroid Hormone on Blood Pressure in Rats," *Endocrinol. Jpn.* 28: 547-549 (1981).

Neer et al., "Effect of Parathyroid Hormone (1-34) on Fractures and Bone Mineral Density in Postmenopausal Women with Osteoporosis," *N. Engl. J. Med.* 344: 1434-1441 (2001).

Neugebauer et al., "Solution Structure and Adenylyl Cyclase Stimulating Activities of C-terminal Truncated Human Parathyroid Hormone Analogues," *Biochemistry* 34: 8835-8842 (1995).

Neugebauer et al., "Structural Elements of Human Parathyroid Hormone and their Possible Relation to Biological Activities," *Biochemistry* 31: 2056-2063 (1992).

Ngo et al. "Chapter 14: Computational Complexity, Protein Structure Prediction, and the Levinthal Paradox" in: *The Protein Folding Problem and Tertiary Structure Prediction* (eds. K.M. Merz et al.), pp. 492-495 (Birkhäuser Verlag, Boston, MA, 1995).

Nielsen et al., "Identification of Prokaryotic and Eukaryotic Signal Peptides and Prediction of their Cleavage Sites," *Prot. Eng.* 10:1-6 (1997).

Nissenson et al., "Synthetic Peptides Comprising the Amino-Terminal Sequence of a Parathyroid Hormone-Like Protein from Human Malignancies. Binding to Parathyroid Hormone Receptors and Activation of Adenylate Cyclase in Bone Cells and Kidney," *J. Biol. Chem.* 263: 12866-12871 (1988).

Nussbaum et al., "Parathyroid Hormone • Renal Receptor Interactions. Demonstration of Two Receptor-binding Domains," *J. Biol. Chem.* 255: 10183-10187 (1980).

Nutt et al., "Removal of Partial Agonism from Parathyroid Hormone (PTH)-Related Protein-(7-34)NH2 by Substitution of PTH Amino Acids at Positions 10 and 11," *Endocrinology* 127: 491-493 (1990).

Oldenburg et al., "Conformational Studies on Analogs of Recombinant Parathyroid Hormone and their Interactions with Phospholipids," *J. Biol. Chem.* 271: 17582-17591 (1996).

Orkin et al. "Report and Recommendations of the Panel to Assess the NIH Investment in Research on Gene Therapy," available online at http://www.nih.gov/news/panelrep.html, pp. 1-39 (1995).

Orloff et al., "A Midregion Parathyroid Hormone-Related Peptide Mobilizes Cytosolic Calcium and Stimulates Formation of Inositol Trisphosphate in a Squamous Carcinoma Cell Line," *Endocrinology* 137: 5376-5385 (1996).

Orloff et al., "Analysis of PTHRP Binding and Signal Transduction Mechanisms in Benign and Malignant Squamous Cells," *Am. J. Physiol.* 262: E599-E607 (1992).

Orloff et al., "Further Evidence for a Novel Receptor for Amino-Terminal Parathyroid Hormone-Related Protein on Keratinocytes and Squamous Carcinoma Cell Lines," *Endocrinology* 136: 3016-3023 (1995).

Pang et al., "Purification of Unique alpha Subunits of GTP-Binding Regulatory Proteins (G Proteins) by Affinity Chromatography with Immobilized beta gamma Subunits," *J. Biol. Chem.* 265: 18707-18712 (1990).

Parsons et al., "Pharmacology of Parathyroid Hormone and Some of its Fragments and Analogues," in: *Calcium-regulating hormones. Proceedings of the Fifth Parathyroid Conference*, Oxford, United Kingdom, Jul. 21-26, 1974 (eds. R.V. Talmage et al.), pp. 33-39 (Am. Elsevier Pub. Co., New York, NY, 1975).

Peggion et al., "Structure-Function Studies of Analogues of Parathyroid Hormone (PTH)-1-34 Containing Beta-Amino Acid Residues in Positions 11-13," Biochemistry 41: 8162-8175 (2002).

Pellegrini et al., "Addressing the Tertiary Structure of Human Parathyroid Hormone-(1-34)," *J. Biol. Chem.* 273: 10420-10427 (1998).

Pellegrini et al., "Binding Domain of Human Parathyroid Hormone Receptor: From Conformation to Function," *Biochemistry* 37: 12737-12743 (1998).

Pettit et al., "The Development of Site-Specific Drug-Delivery Systems for Protein and Peptide Biopharmaceuticals," *Trends Biotechnol.* 16: 343-349 (1998).

Phillips et al., "The Challenge of Gene Therapy and DNA Delivery," *J. Pharm. Pharmacol.* 53: 1169-1174 (2001).

Pines et al., "Generation and Characterization of Human Kidney Cell Lines Stably Expressing Recombinant Human PTH/PTHrP Receptor: Lack of Interaction with a C-Terminal Human PTH Peptide," *Endocrinology* 135: 1713-1716 (1994).

Pines et al., "Inositol 1-,4-,5-Trisphosphate-Dependent Ca2+ Signaling by the Recombinant Human PTH/PTHrP Receptor Stably Expressed in a Human Kidney Cell Line," *Bone* 18: 381-389 (1996).

Plotkin et al., "Dissociation of Bone Formation from Resorption during 2-week Treatment with Human Parathyroid Hormone-Related Peptide-(1-36) in Humans: Potential as an Anabolic Therapy for Osteoporosis," *J. Clin. Endocrinol. Metab.* 83: 2786-2791 (1998).

Potts et al., "Structure Based Design of Parathyroid Hormone Analogs," *J. Endocrinol.* 154 Suppl: S15-S21 (1997).

Potts et al., "Parathyroid Hormone and Parathyroid Hormone-Related Peptide in Calcium Homeostasis, Bone Metabolism, and Bone Development: The Proteins, Their Genes, and Receptors," in: *Metabolic Bone Disease*, 3rd Edition (eds. L.V. Avioli et al.), pp. 51-94 (Acad. Press, San Diego, CA, 1998).

Ray et al., "NMR Solution Structure of the [A1a26]Parathyroid-Hormone-Related Protein(1-34) Expressed in Humoral Hypercalcemia of Malignancy," *Eur. J. Biochem.* 211: 205-211 (1993).

Reid et al., "Parathyroid Hormone Acutely Elevates Intracellular Calcium in Osteoblastlike Cells," *Am. J. Physiol.* 253: E45-E51 (1987).

Reidhaar-Olson et al., "Active Variants of Human Parathyroid Hormone (1-34) with Multiple Amino Acid Substitutions," *Mol. Cell. Endocrinol.* 160: 135-147 (2000).

Rixon et al., "Parathyroid Hormone Fragments May Stimulate Bone Growth in Ovariectomized Rats by Activating Adenylyl Cyclase," *J. Bone Miner. Res.* 9: 1179-1189 (1994).

Roe at al., "Parathyroid Hormone 1-34 (hPTH 1-34) and Estrogen Produce Dramatic Bone Density Increases in Postmenopausal Osteoporosis. Results from a Placebo-Controlled Randomized Trial," *J. Bone Miner. Res.* 14:S137, Abstract No. 1019 (1999).

Rölz et al., "Characterization of the Molecular Motions of Constitutively Active G Protein-Coupled Receptors for Parathyroid Hormone," *Biophys. Chem.* 89: 119-128 (2001).

Romano et al., "Latest Developments in Gene Transfer Technology: Achievements, Perspectives, and Controversies over Therapeutic Applications," *Stem Cells* 18: 19-39 (2000).

Rosenblatt et al., "Design and Synthesis of Parathyroid Hormone Analogues of Enhanced Biological Activity," *Endocr. Res. Commun.* 4: 115-133 (1977).

Rosenblatt et al., "Identification of a Receptor-binding Region in Parathyroid Hormone," *Endocrinology* 107: 545-550 (1980).

Rosenblatt, "Parathyroid Hormone: Chemistry and Structure-Activity Relations," *Pathobiol. Annu.* 11: 53-86 (1981).

Rosol et al., "Sequences of the cDNAs Encoding Canine Parathyroid Hormone-Related Protein and Parathyroid Hormone," *Gene* 160: 241-243 (1995).

Rubin et al., "Molecular Cloning and Expression of Receptors for Parathyroid Hormone (PTH) and PTH-Related (PTHrP) Protein in Zebrafish," *Am. Zoologist* 36: 97A, Abstract No. 373 (1996).

Rubin et al., "Molecular Cloning of a Zebrafish cDNA Encoding a Novel Parathyroid Hormone (PTH)/PTH-Related Protein (PTHrP) Receptor (PPR)," *Bone* 23: S255, Abstract No. T224 (1998).

Rubin et al., "Parathyroid Hormone (PTH)/PTH-Related (PTHRP) Receptor Cloning and in Situ Hybridization in the Zebrafish, Danio Rerio," *Am. Zoologist* 37: 181A, Abstract No. 651 (1997).

Rubin et al., "Zebrafish Express the Common Parathyroid Hormone/Parathyroid Hormone-Related Peptide Receptor (PTH1R) and a Novel Receptor (PTH3R) that is Preferentially Activated by Mammalian and Fugufish Parathyroid Hormone-Related Peptide," *J. Biol. Chem.* 274: 28185-28190 (1999).

Sacchetti et al., "Green Fluorescent Protein Variants Fold Differentially in Prokaryotic and Eukaryotic Cells," *J. Cell. Biochem. Suppl.* 36: 117-128 (2001).

Sargent et al., "Membrane Lipid Phase as Catalyst for Peptide-Receptor Interactions," *Proc. Natl. Acad. Sci. USA* 83: 5774-5778 (1986).

Schipani et al., "A Constitutively Active Mutant PTH-PTHrP Receptor in Jansen-Type Metaphyseal Chondrodysplasia," *Science* 268: 98-100 (1995).

Schipani et al., "Identical Complementary Deoxyribonucleic Acids Encode a Human Renal and Bone Parathyroid Hormone (PTH)/PTH-Related Peptide Receptor," *Endocrinology* 132: 2157-2165 (1993).

Schipani et al., "Pseudohypoparathyroidism Type Ib is not Caused by Mutations in the Coding Exons of the Human Parathyroid Hormone (PTH)/PTH-Related Peptide Receptor Gene," *J. Clin. Endocrinol. Metab.* 80: 1611-1621 (1995).

Schneider et al., "A C-Terminally Truncated Human Parathyroid Hormone Receptor is Functional and Activates Multiple G Proteins," *FEBS Lett.* 351: 281-285 (1994).

Schneider et al., "Cloning and Functional Expression of a Human Parathyroid Hormone Receptor," *Eur. J. Pharmacol.* 246: 149-155 (1993).

Segre et al., "Characterization of Parathyroid Hormone Receptors in Canine Renal Cortical Plasma Membranes Using a Radioiodinated Sulfur-Free Hormone Analogue. Correlation of Binding with Adenylate Cyclase Activity," *J. Biol. Chem.* 254: 6980-6986 (1979).

Segre et al., "Receptors for Secretin, Calcitonin, Parathyroid Hormone (PTH)/PTH-Related Peptide, Vasoactive Intestinal Peptide, Glucagonlike Peptide 1, Growth Hormone-Releasing Hormone, and Glucagon Belong to a Newly Discovered G-protein-Linked Receptor Family," *Trends Endocrinol. Metab.* 4: 309-314 (1993).

Seuwen et al., "Heparin-Insensitive Calcium Release from Intracellular Stores Triggered by the Recombinant Human Parathyroid Hormone Receptor," *Br. J. Pharmacol.* 114: 1613-1620 (1995).

Shen et al., "Effects of Combined and Separate Intermittent Administration of Low-Dose Human Parathyroid Hormone Fragment (1-34) and 17 Beta-Estradiol on Bone Histomorphometry in Ovariectomized Rats with Established Osteopenia," *Calcif. Tissue Int.* 50: 214-220 (1992).

Shigeno et al., "Parathyroid Hormone Receptors are Plasma Membrane Glycoproteins with Asparagine-Linked Oligosaccharides," *J. Biol. Chem.* 263: 3872-3878 (1988).

Shimizu et al., "Amino-Terminal Parathyroid Hormone Fragment Analogs Containing $\alpha,\alpha$-di-alkyl Amino Acids at Positions 1 and 3," *J. Bone Miner. Res.* 19: 2078-2086 (2004).

Shimizu et al., "Autoactivation of Type-1 Parathyroid Hormone Receptors Containing a Tethered Ligand," *J. Biol. Chem.* 275: 19456-19460 (2000).

Shimizu et al., "Enhanced Activity in Parathyroid Hormone-(1-14) and -(1-11): Novel Peptides for Probing Ligand-Receptor Interactions," *Endocrinology* 142: 3068-3074 (2001).

Shimizu et al., "Functional Evidence for an Intramolecular Side Chain Interaction between Residues 6 and 10 of Receptor-Bound Parathyroid Hormone Analogues," *Biochemistry* 42: 2282-2290 (2003).

Shimizu et al., "Minimization of Parathyroid Hormone. Novel Amino-Terminal Parathyroid Hormone Fragments with Enhanced Potency in Activating the Type-1 Parathyroid Hormone Receptor," *J. Biol. Chem.* 275: 21836-21843 (2000).

Shimizu et al., "Novel Parathyroid Hormone (PTH) Antagonists that Bind to the Juxtamembrane Portion of the PTH/PTH-Related Protein Receptor," *J. Biol. Chem.* 280: 1797-1807 (2005).

Shimizu et al., "Parathyroid Hormone (PTH)-(1-14) and -(1-11) Analogs Conformationally Constrained by $\mu$-Aminosobutyric Acid Mediate Full Agonist Responses via the Juxtamembrane Region of the PTH-1 Receptor," *J. Biol. Chem.* 276: 49003-49012 (2001).

Shimada et al., "Purification and Characterization of a Receptor for Human Parathyroid Hormone and Parathyroid Hormone-Related Peptide," *J. Biol. Chem.* 277: 31774-31780 (2002).

Shimizu et al., "Residue 19 of the Parathyroid Hormone (PTH) Modulates Ligand Interaction with the Juxtamembrane Region of the PTH-1 Receptor," *Biochemistry* 41: 13224-13233 (2002).

Shimizu et al., "Structurally Varied Conformationally Constrained Amino Acids Substitutions at Positions 1 and 3 of PTH(1-14) Preserve or Enhance P1R Binding Affinity and cAMP-signaling Potency," *J. Bone Miner. Res.* 17: S389 (2002).

Shimizu et al., "Type-Substitution Analysis of the Amino-Terminal Fragment of Parathyroid Hormone, PTH(1-14): an Approach toward New Low Molecular Weight PTH Agonists," *J. Bone Miner. Res.* 14: S289, Abstract No. F398 (1999).

Shukunami et al., "Chondrogenic Differentiation of Clonal Mouse Embryonic Cell Line ATDC5 in Vitro: Differentiation-dependent Gene Expression of Parathyroid Hormone (PTH)/PTH-related Peptide Receptor," *J. Cell Biol.* 133: 457-468 (1996).

Siegfried et al., "Parathyroid Hormone Stimulates Ecto-5'-Nucleotidase Activity in Renal Epithelial Cells: Role of Protein Kinase-C," *Endocrinology* 136:1267-1275 (1995).

Simon et al., "Diversity of G Proteins in Signal Transduction," *Science* 252: 802-808 (1991).

Skolnick et al., "From Genes to Protein Structure and Function: Novel Applications of Computational Approaches in the Genomic Era," *Trends Biotechnol.* 18: 34-39 (2000).

Slovik et al., "Restoration of Spinal Bone in Osteoporotic Men by Treatment with Human Parathyroid Hormone (1-34) and 1,25-dihydroxyvitamin D," *J. Bone Miner. Res.* 1: 377-381 (1986).

Smith et al., "The Challenges of Genome Sequence Annotation or "The devil is in the details"," *Nat. Biotechnol.* 15: 1222-1223 (1997).

Strathman et al., "G Protein Diversity: A Distinct Class of alpha Subunits is Present in Vertebrates and Invertebrates," *Proc. Natl. Acad. Sci. USA* 87: 9113-9117 (1990).

Strojek et al., "The Use of Transgenic Animal Techniques for Livestock Improvement," in: *Genetic Engineering: Principles and Methods*, vol. 10 (eds. J.K. Setlow et al.), pp. 221-246 (Plenum Press, New York, NY, 1988).

Stroop et al., "Chimeric Human Calcitonin and Glucagon Receptors Reveal Two Dissociable Calcitonin Interaction Sites," *Biochemistry* 34: 1050-1057 (1995).

Sunyaev et al., "From Analysis of Protein Structrual Alignments Toward a Novel Approach to Align Protein Sequences," *Proteins* 54: 569-582 (2004).

Suva et al., "A Parathyroid Hormone-Related Protein Implicated in Malignant Hypercalcemia: Cloning and Expression," *Science* 237: 893-896 (1987).

Szabo, "In Situ Hybridization," in: *Human Chromosomes: Manual of Basic Techniques* (eds. R.S. Verma et al.), pp. 152-165 (Pergamon Press, New York, NY, 1989).

Takasu et al., "Amino Terminal Modifications of Human Parathyroid Hormone (PTH) Selectively Alter Phospholipase C Signaling via the Type 1 PTH Receptor: Implications for Design for Signal-Specific PTH Ligands," *Biochemistry* 38: 13453-13460 (1999).

Takasu et al., "Dual Signaling and Ligand Selectivity of the Human PTH/PTHrP Receptor," *J. Bone Miner. Res.* 14: 11-20 (1999).

Takasu et al., "Human PTH/PTHrP Receptors and Type-2 PTH Receptos Show Discordant Selectivity for Human PTH Analogs with Amino-Terminal Modifications," *Bone* 23:S255, Abstract No. T223 (1998).

Takasu et al., "Phospholipase C Activation via the Human PTH/PTHrP Receptor Requires an Intact Amino-Terminus of Human PTH," *Bone* 23: S447, Abstract No. F148 (1998).

Takasu et al., "The 69-84 Amino Acid Region of the Parathyroid Hormone Molecule is Essential for the Interaction of the Hormone with the Binding Sites with Carboxyl-terminal Specificity," *Endocrinology* 137: 5537-5543 (1996).

Takasu et al., "Type-1 Parathyroid Hormone (PTH)/PTH-Related Peptide (PTHrP) Receptors Activate Phospholipase C in Response to Carboxyl-truncated Analogs of PTH(1-34)," *Endocrinology* 139: 4293-4299 (1998).

Tamura et al., "Parathyroid Hormone 1-34, but not 3-34 or 7-34, Transiently Translocates Protein Kinase C in Cultured Renal (OK) Cells," *Biochem. Biophys. Res. Commun.* 159: 1352-1358 (1989).

Tan et al., "Peptide Agonist Docking in the N-Terminal Ectodomain of a Class II G Protein-Coupled Receptor, the VPAC1 Receptor. Photoaffinity, NMR, and Molecular Modeling," *J. Biol. Chem.* 281: 12792-12798 (2006).

Treanor et al., "Characterization of a Multicomponent Receptor for GDNF," *Nature* 382: 80-83 (1996).

Tregear et al., "Bovine Parathyroid Hormone: Minimum Chain Length of Synthetic Peptide Required for Biological Activity," *Endocrinology* 93: 1349-1353 (1973).

Tregear et al., "Synthetic Analogues of Residues 1-34 of Human Parathyroid Hormone: Influence of Residue No. 1 on Biological Potency in Vitro," *Endocr. Res. Commun.* 2: 561-570 (1975).

Tsomaia et al., "Cooperative Interaction of Arginine-19 and the N-Terminal Signaling Domain in the Affinity and Potency of Parathyroid Hormone," *Biochemistry* 43: 3459-3470 (2004).

Tsomaia et al., "Toward Parathyroid Hormone Minimization: Conformational Studies of Cyclic PTH(1-14) Analogues," *Biochemistry* 43: 690-699 (2004).

Turner et al., "A Putative Selectivity Filter in the G-Protein-Coupled Receptors for Parathyroid Hormone and Secretin," *J. Biol. Chem.* 271: 9205-9208 (1996).

Turner et al., "Single Mutations Allow the PTH2 Receptor to Respond to PTHrP," *J. Bone Miner. Res.* 12: S133, Abstract No. 121 (1997).

Turner et al., "Transmembrane Residues Together with the Amino Terminus Limit the Response of the Parathyroid Hormone (PTH) 2 Receptor to PTH-Related Peptide," *J. Biol. Chem.* 273: 3830-3837 (1998).

Ullrich et al., "Signal Transduction by Receptors with Tyrosine Kinase Activity," *Cell* 61: 203-212 (1990).

Unson et al., "Characterization of Deletion and Truncation Mutants of the Rat Glucagon Receptor. Seven Transmembrane Segments are Necessary for Receptor Transport to the Plasma Membrane and Glucagon Binding," *J. Biol. Chem.* 270: 27720-27727 (1995).

Ureña et al., "Regulation of Parathyroid Hormone (PTH)/PTH-Related Peptide Receptor Messenger Ribonucleic Acid by Glucocorticoids and PTH in ROS 17/2.8 and OK Cells," *Endocrinology* 134: 451-456 (1994).

Usdin et al., "Identification and Functional Expression of a Receptor Selectively Recognizing Parathyroid Hormone, the PTH2 Receptor," *J. Biol. Chem.* 270: 15455-15458 (1995).

Verma et al. "Gene Therapy—Promises, Problems and Prospects," *Nature* 389: 239-242 (1997).

Voet et al., "3. Chemical Evolution," in: *Biochemistry* (eds. D. Voet et al.), pp. 126-128 and 228-234 (Wiley, New York, NY, 1990).

Vogt et al., "An Assessment of Amino Acid Exchange Matrices in Aligning Protein Sequences: The Twilight Zone Revisited," *J. Mol. Biol.* 249: 816-831 (1995).

Wall, "Transgenic Livestock: Progress and Prospects for the Future," *Theriogenology* 45: 57-68 (1996).

Wang et al., "Rapid Analysis of Gene Expression (RAGE) Facilitates Universal Expression Profiling," *Nucleic Acids Res.* 27: 4609-4618 (1999).

Wells, "Additivity of Mutational Effects in Proteins," *Biochemistry* 29: 8509-8517 (1990).

Wells, "Hormone Mimicry," *Science.* 273: 449-450 (1996).

Whitfield et al., "Comparison of the Ability of Recombinant Human Parathyroid Hormone, rhPTH-(1-84), and hPTH-(1-31)NH2 to Stimulate Femoral Trabecular Bone Growth in Ovariectomized Rats," *Calcif. Tissue Int.* 60: 26-29 (1997).

Whitfield et al., "Restoration of Severely Depleted Femoral Trabecular Bone in Ovariectomized Rats by Parathyroid Hormone-(1-34)," *Calcif. Tissue Int.* 56:227-231 (1995).

Whitfield et al., "Small Bone-Building Fragments of Parathyroid Hormone: New Therapeutic Agents for Osteoporosis," *Trends Pharmacol. Sci.* 16: 382-386 (1995).

Whitfield et al., "Stimulation of the Growth of Femoral Trabecular Bone in Ovariectomized Rats by the Novel Parathyroid Hormone Fragment, hPTH-(1-31)NH2 (Ostabolin)," *Calcif. Tissue Int.* 58: 81-87 (1996).

Wigley et al., "Site-Specific Transgene Insertion: An Approach," *Reprod. Fertil. Dev.* 6: 585-588 (1994).

Wittelsberger et al., "The Mid-Region of Parathyroid Hormone (1-34) Serves as a Functional Docking Domain in Receptor Activation," *Biochemistry* 45: 2027-2034 (2006).

Wrighton et al., "Small Peptides as Potent Mimetics of the Protein Hormone Erythropoietin," *Science* 273: 458-463 (1996).

Wu et al., "Structural and Physiologic Characterization of the Midregion Secretory Species of Parathyroid Hormone-Related Protein," *J. Biol. Chem.* 271: 24371-24381 (1996).

Yamaguchi et al., "Parathyroid Hormone-Activated Calcium Channels in an Osteoblast-Like Clonal Osteosarcoma Cell Line: cAMP-Dependent and cAMP-Independent Calcium Channels," *J. Biol. Chem.* 262: 7711-7718 (1987).

Yamamoto et al., "Centrally Administered Parathyroid Hormone (PTH)-Related Protein(1-34) but not PTH(1-34) Stimulates Arginine-Vasopressin Secretion and its Messenger Ribonucleic Acid Expression in Supraoptic Nucleus of the Conscious Rats," *Endocrinology* 138: 383-388 (1998).

Yamamoto et al., "Parathyroid Hormone-Related Peptide-(1-34) [PTHrP-(1-34)] Induces Vasopressin Release from the Rat Supraoptic Nucleus in Vitro Through a Novel Receptor Distinct from a Type I or Type II PTH/PTHrP Receptor," *Endocrinology* 138: 2066-2072 (1997).

Yamamoto et al., "Characterization and Agonist-Induced Down-Regulation of Parathyroid Hormone Receptors in Clonal Rat Osteosarcoma Cells," *Endocrinology* 122:1208-1217 (1988).

Yan et al., "Two-Amino Acid Molecular Switch in an Epithelial Morphogen that Regulates Binding to Two Distinct Receptors," *Science* 290: 523-527 (2000).

Zhou et al., "Direct Mapping of an Agonist-Binding Domain within the Parathyroid Hormone/Parathyroid Hormone-Related Protein Receptor by Photoaffinity Crosslinking," *Proc. Natl. Acad. Sci. USA* 94: 3644-3649 (1997).

International Search Report and Written Opinion for PCT/US2007/017338 (mailed Aug. 14, 2008).

Partial European Search Report for EP08018788 (mailed Jan. 30, 2009).

* cited by examiner

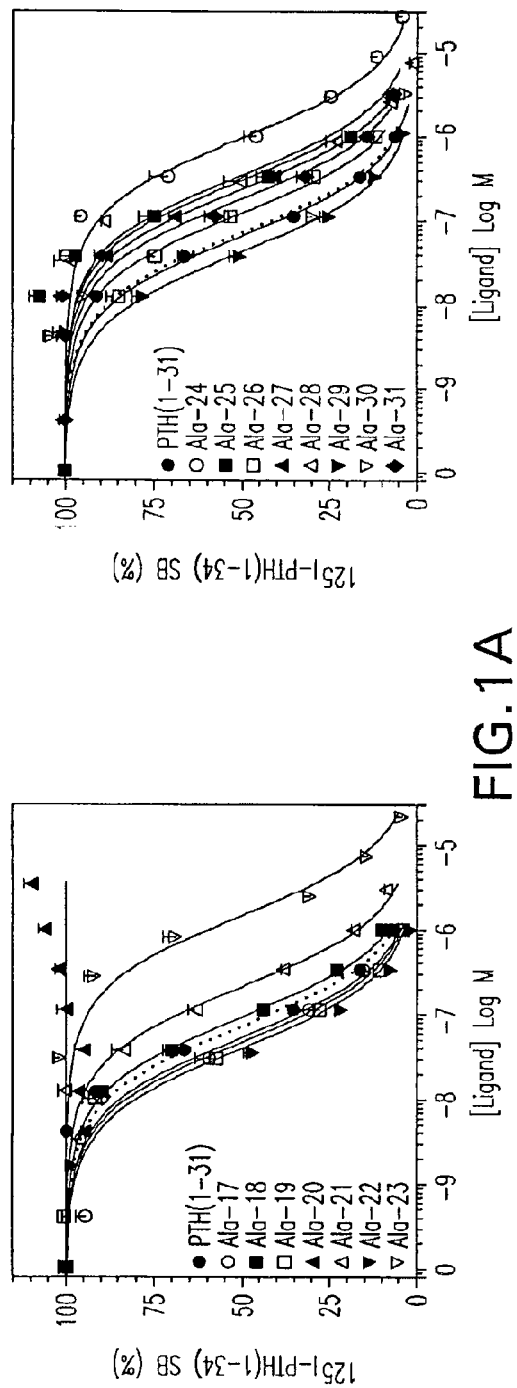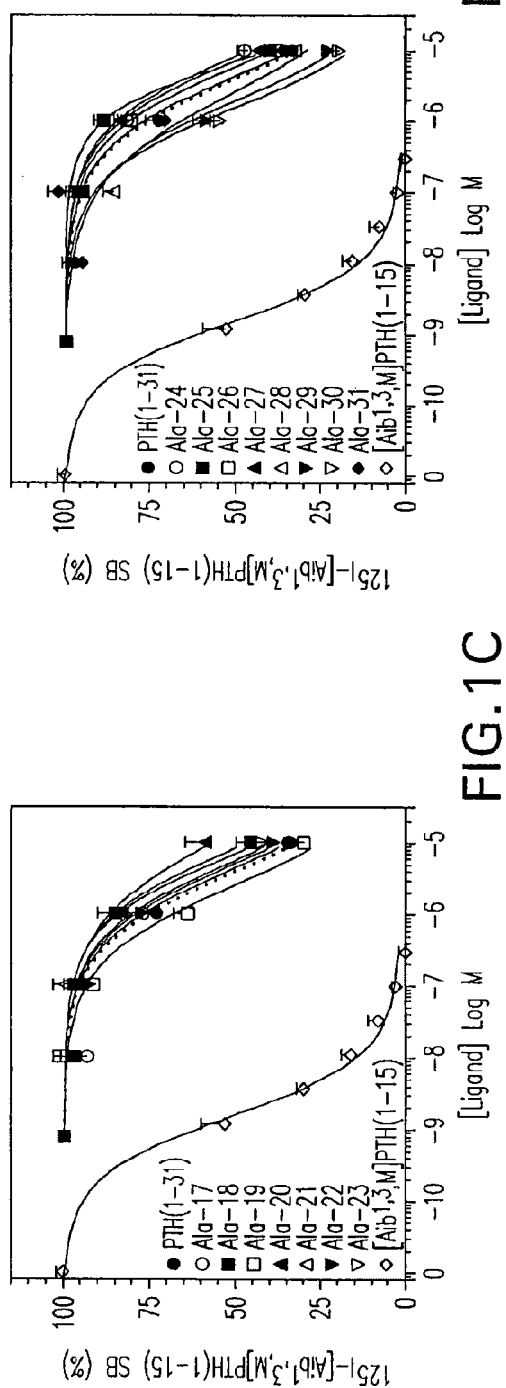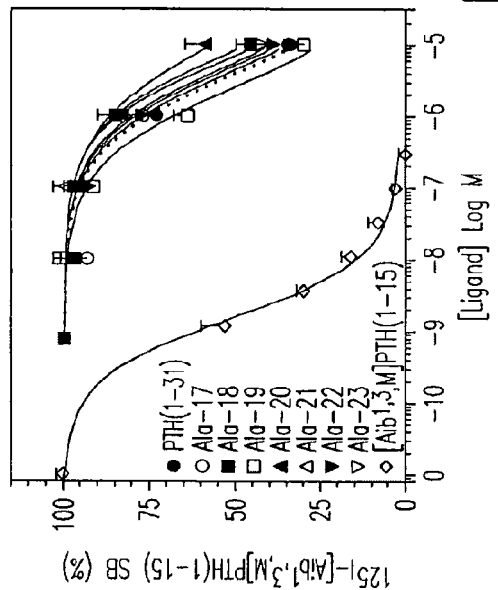
FIG. 1A  FIG. 1B  FIG. 1C  FIG. 1D

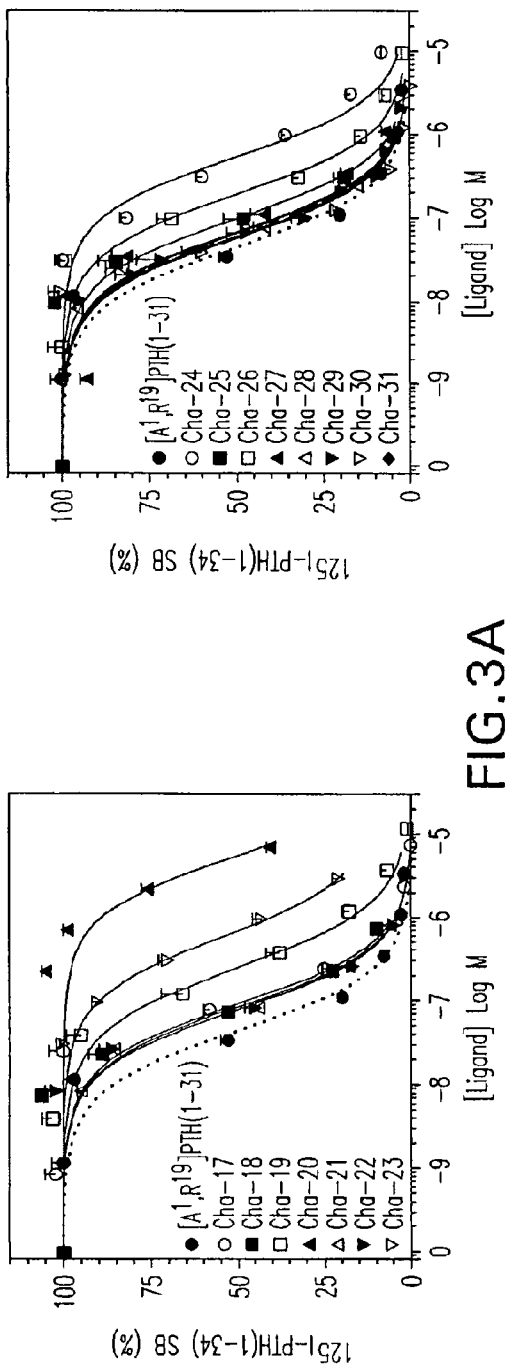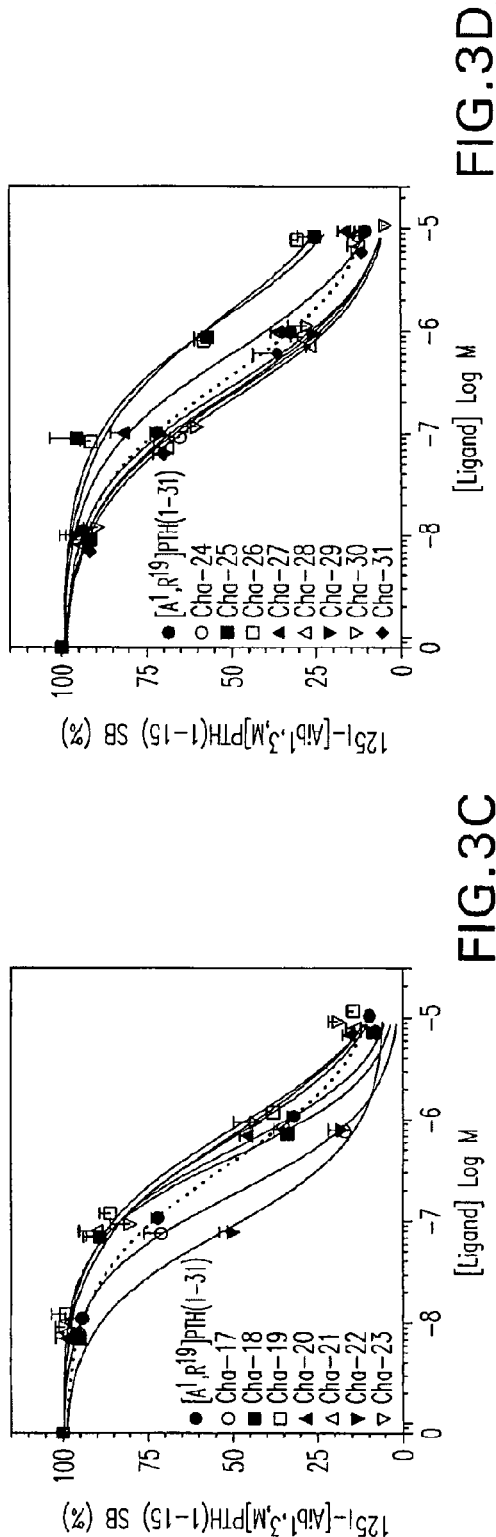

POLYPEPTIDE DERIVATIVES OF PARATHYROID HORMONE (PTH)

STATEMENT AS TO RIGHTS TO INVENTIONS MADE UNDER FEDERALLY SPONSORED RESEARCH AND DEVELOPMENT

This invention was made with Government support under Grant No. DK011794 awarded by the National Institutes of Health. The Government has certain rights in this invention.

BACKGROUND OF THE INVENTION

1. Field of the Invention

The present invention is related to novel parathyroid hormone (PTH) peptide derivatives, nucleic acids encoding the PTH derivatives and methods of preparing and using the PTH derivatives. The PTH derivatives may have one or more amino acid substitutions at selected positions in the polypeptide.

2. Background

Parathyroid Hormone

Parathyroid hormone (PTH), an 84 amino acid peptide, is the principal regulator of ionized blood calcium in the human body (Kronenberg, H. M., et al., In *Handbook of Experimental Pharmacology*, Mundy, G. R., and Martin, T. J., (eds), pp. 185-201, Springer-Verlag, Heidelberg (1993)). Regulation of calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone indirectly by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH is thought to exert these effects primarily through receptor-mediated activation of adenylate cyclase and/or phospholipase C.

Disruption of calcium homeostasis may produce many clinical disorders (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a parathyroid gland lesion (e.g., adenoma, hyperplasia, or carcinoma). Another type of hypercalcemia, humoral hypercalcemia of malignancy (HHM) is the most common paraneoplastic syndrome. It appears to result in most instances from the production by tumors (e.g., squamous, renal, ovarian, or bladder carcinomas) of a class of protein hormone which shares amino acid homology with PTH. These PTH-related proteins (PTHrP) appear to mimic certain of the renal and skeletal actions of PTH and are believed to interact with the PTH receptor in these tissues.

Osteoporosis

Osteoporosis is a potentially crippling skeletal disease observed in a substantial portion of the senior adult population, in pregnant women and even in juveniles. The term osteoporosis refers to a heterogeneous group of disorders. Clinically, osteoporosis is separated into type I and type II. Type I osteoporosis occurs predominantly in middle aged women and is associated with estrogen loss at menopause, while osteoporosis type II is associated with advancing age. Patients with osteoporosis would benefit from new therapies designed to promote fracture repair, or from therapies designed to prevent or lessen the fractures associated with the disease.

The disease is marked by diminished bone mass, decreased bone mineral density (BMD), decreased bone strength and an increased risk of bone fracture. At present, there is no effective cure for osteoporosis, though estrogen, calcitonin and the bisphosphonates, etidronate and alendronate are used to treat the disease with varying levels of success. These agents act to decrease bone resorption. Since parathyroid hormone regulates blood calcium and the phosphate levels, and has potent anabolic (bone-forming) effects on the skeleton, in animals (Shen, V., et al., *Calcif. Tissue Int.* 50:214 220 (1992); Whitefild, J. F., et al., *Calcif. Tissue Int.* 56:227 231 (1995) and Whitfield, J. F., et al., *Calcif. Tissue Int.* 60:26 29 (1997)) and humans (Slovik, D. M., et al., *J. Bone Miner. Res.* 1:377 381 (1986); Dempster, D. W., et al., *Endocr. Rev.* 14:690 709 (1993) and Dempster, D. W., et al., *Endocr. Rev.* 15:261 (1994)) when administered intermittently, PTH, or PTH derivatives, are prime candidates for new and effective therapies for osteoporosis.

PTH Derivatives

PTH derivatives include polypeptides that have amino acid substitutions or are truncated relative to the full length molecule. Both a 14 and a 34 amino acid amino-terminal truncated form of PTH, as well as a C-terminal truncated form have been studied. Additionally, amino acid substitutions within the truncated polypeptides have also been investigated.

Synthetic PTH(1-34) exhibits full bioactivity in most cell-based assay systems, has potent anabolic effects on bone mass in animals and has been shown to reduce the risk of bone fracture in postmenopausal osteoporotic women (Neer, R. M., et al., *N.E.J.M.* 344:1434-1441 (2001); Dempster, D. W., et al., *Endocr Rev* 14:690-709 (1993)). PTH acts on the PTH/PTHrP receptor (P1R), a class II G protein-coupled heptahelical receptor that couples to the adenylyl cyclase/cAMP and phospholipase C/inositol phosphate (IP) signaling pathway (Rippner, H., et al., *Science* 254:1024-1026 (1991)). Deletion analysis studies have shown that the amino-terminal residues of PTH play a crucial role in stimulating the P1R to activate the cAMP and IP signaling pathways (Tregear, G. W., et al., *Endocrinology* 93:1349-1353 (1973); Takasu, H., et al., *Biochemistry* 38:13453-13460 (1999)). Crosslinking and receptor mutagenesis studies have indicated that residues in the amino-terminal portion of PTH interact with the extracellular loops and extracellular ends of the seven transmembrane helices, which reside within the juxtamembrane region of the receptor (Bergwitz, C., et al., *J. Biol. Chem.* 271:26469-26472 (1996); Hoare, S. R. J., et al., *J. Biol. Chem* 276:7741-7753 (2001); Behar, V., et al., *J. Biol. Chem.* 275:9-17 (1999); Shimizu, M., et al., *J. Biol. Chem.* 275:19456-19460 (2000); Luck, M. D., et al., *Molecular Endocrinology* 13:670-680 (1999)).

Therefore, there exists a need in the art for new PTH derivatives that can be used to treat patients in need of treatment of diseases involving the parathyroid hormone, such as bone-related defects or diseases, methods of making and using these derivatives as well as methods of using the derivatives to treat patients with various parathyroid hormone related defects or diseases.

BRIEF SUMMARY OF THE INVENTION

The present invention provides novel parathyroid hormone polypeptide derivatives containing amino acid substitutions at selected positions in the polypeptide. In some embodiments, the present invention provides a biologically active peptide at least 90% identical to a peptide consisting essentially of the formula: (a) $X_{01}$ValSerGluIle GlnLeuMetHisAsnLeuGlyLysHisLeuAsnSerMet$X_{02}X_{03}$ $X_{04}$Glu$X_{05}X_{06}$ArgLysLys$X_{07}$GlnAspVal (SEQ ID NO:1); (b) fragments thereof, containing amino acids 1-20, 1-21, 1-22, 1-23, 1-24, 1-25, 1-26, 1-27, 1-28, 1-29 or 1-30; (c) pharmaceutically acceptable salts thereof; or (d) N- or C-derivatives thereof; wherein: $X_{01}$ is Ser or Ala; $X_{02}$ is Glu or Arg; $X_{03}$ is Ala, Glu, Gln or Cha; $X_{04}$ is Val or Glu; $X_{05}$ is Trp, Ala, Glu or Cha; $X_{06}$ is Leu, Ala, Glu or Cha; and $X_{07}$ is Leu or Glu; provided that said peptide is not hPTH(1-31)$NH_2$.

In some embodiments, the invention provides a biologically active peptide consisting essentially of the formula: (a) $X_{01}$ValSerGluIleGlnLeuMetHisAsnLeuGlyLysHisLeuAsn SerMet$X_{02}X_{03}X_{04}$Glu$X_{05}X_{06}$ArgLysLys$X_{07}$GlnAspVal (SEQ ID NO:1); (b) fragments thereof, containing amino acids 1-20, 1-21, 1-22, 1-23, 1-24, 1-25, 1-26, 1-27, 1-28, 1-29 or 1-30; (c) pharmaceutically acceptable salts thereof; or (d) N- or C-derivatives thereof; wherein: $X_{01}$ is Ser or Ala; $X_{02}$ is Glu or Arg; $X_{03}$ is Ala, Glu, Gln or Cha; $X_{04}$ is Val or Glu; $X_{05}$ is Trp, Ala, Glu or Cha; $X_{06}$ is Leu, Ala, Glu or Cha; and $X_{07}$ is Leu or Glu; provided that said peptide is not hPTH(1-31)$NH_2$.

In some embodiments, the invention provides a peptide consisting essentially of the formula: (a) SerValSerGluIleGlnLeuMetHisAsnLeuGlyLysHisLeuAsnSerMetGluAlaValGluTrpLeuArgLysLysLeuGlnAspVal (SEQ ID NO:2), SerValSerGluIleGlnLeuMetHisAsnLeuGlyLysHisLeuAsnSerMetGluArgValGluAlaLeuArgLysLysLeuGlnAspVal (SEQ ID NO:3), SerValSerGluIleGlnLeuMetHisAsnLeuGlyLysHisLeuAsnSerMetGluArgValGluTrpAlaArgLysLysLeuGlnAspVal (SEQ ID NO:4), SerValSerGluIleGlnLeuMetHisAsnLeuGlyLysHisLeuAsnSerMetGluGluValGluTrpLeuArgLysLysLeuGlnAspVal (SEQ ID NO:5), AlaValSerGluIleGlnLeuMetHisAsnLeuGlyLysHisLeuAsnSerMetArgArgValGluGluLeuArgLysLysLeuGlnAspVal (SEQ ID NO:6), AlaValSerGluIleGlnLeuMetHisAsnLeuGlyLysHisLeuAsnSerMetArgArgValGluTrpGluArgLysLysLeuGlnAspVal (SEQ ID NO:7), AlaValSerGluIleGlnLeuMetHisAsnLeuGlyLysHisLeuAsnSerMetArgArgValGluTrpLeuArgLysLysGluGlnAspVal (SEQ ID NO:8), AlaValSerGluIleGlnLeuMetHisAsnLeuGlyLysHisLeuAsnSerMetArgArgGluGluTrpLeuArgLysLysLeuGlnAspVal (SEQ ID NO:9), AlaValSerGluIleGlnLeuMetHisAsnLeuGlyLysHisLeuAsnSerMetArgChaValGluTrpLeuArgLysLysLeuGlnAspVal (SEQ ID NO:10), AlaValSerGluIleGlnLeuMetHisAsnLeuGlyLysHisLeuAsnSerMetArgArgValGluChaLeuArgLysLysLeuGlnAspVal (SEQ ID NO:11), or AlaValSerGluIleGlnLeuMetHisAsnLeuGlyLysHisLeuAsnSerMetArgArgValGluTrpChaArgLysLysLeuGlnAspVal (SEQ ID NO:12); (b) fragments thereof, containing amino acids 1-20, 1-21, 1-22, 1-23, 1-24, 1-25, 1-26, 1-27, 1-28, 1-29 or 1-30; (c) pharmaceutically acceptable salts thereof; or (d) N- or C-derivatives thereof.

In some embodiments of the present invention, the peptides can be labeled with a label selected from the group consisting of radiolabel, fluorescent label, bioluminescent label, and chemiluminescent label.

The present invention also provides a pharmaceutical composition comprising a pharmaceutically acceptable carrier and a biologically active peptide at least 90% identical to a peptide consisting essentially of the formula: (a) $X_{01}$ValSerGluIleGlnLeuMetHisAsnLeuGlyLysHisLeuAsn SerMet$X_{02}X_{03}X_{04}$Glu$X_{05}X_{06}$ArgLysLys$X_{07}$GlnAspVal (SEQ ID NO:1); (b) fragments thereof, containing amino acids 1-20, 1-21, 1-22, 1-23, 1-24, 1-25, 1-26, 1-27, 1-28, 1-29 or 1-30; (c) pharmaceutically acceptable salts thereof; or (d) N- or C-derivatives thereof; wherein: $X_{01}$ is Ser or Ala; $X_{02}$ is Glu or Arg; $X_{03}$ is Ala, Glu, Gln or Cha; $X_{04}$ is Val or Glu; $X_{05}$ is Trp, Ala, Glu or Cha; $X_{06}$ is Leu, Ala, Glu or Cha; and $X_{07}$ is Leu or Glu; provided that said peptide is not hPTH(1-31)$NH_2$.

In addition, the present invention provides a nucleic acid molecule consisting essentially of a polynucleotide encoding a biologically active peptide at least 90% identical to a peptide consisting essentially of the formula: (a) $X_{01}$ ValSerGluIleGlnLeuMetHisAsnLeuGlyLysHisLeuAsnSer Met$X_{02}X_{03}X_{04}$Glu$X_{05}X_{06}$ArgLysLys$X_{07}$GlnAspVal (SEQ ID NO:1); (b) fragments thereof, containing amino acids 1-20, 1-21, 1-22, 1-23, 1-24, 1-25, 1-26, 1-27, 1-28, 1-29 or 1-30; (c) pharmaceutically acceptable salts thereof; or (d) N- or C-derivatives thereof; wherein: $X_{01}$ is Ser or Ala; $X_{02}$ is Glu or Arg; $X_{03}$ is Ala, Glu, Gln or Cha; $X_{04}$ is Val or Glu; $X_{05}$ is Trp, Ala, Glu or Cha; $X_{06}$ is Leu, Ala, Glu or Cha; and $X_{07}$ is Leu or Glu; provided that said peptide is not hPTH(1-31) $NH_2$. The present invention also provides a recombinant vector comprising such a nucleic acid molecule.

The present invention is also directed to a recombinant DNA molecule comprising: (1) an expression control region, said region in operable linkage with (2) a polynucleotide sequence coding for a biologically active peptide at least 90% identical to a peptide consisting essentially of the formula: (a) $X_{01}$ValSerGluIleGlnLeuMetHisAsnLeuGlyLysHisLeuAsn SerMet$X_{02}X_{03}X_{04}$Glu$X_{05}X_{06}$ArgLysLys$X_{07}$GlnAspVal (SEQ ID NO:1); (b) fragments thereof, containing amino acids 1-20, 1-21, 1-22, 1-23, 1-24, 1-25, 1-26, 1-27, 1-28, 1-29 or 1-30; (c) pharmaceutically acceptable salts thereof; or (d) N- or C-derivatives thereof; wherein: $X_{01}$ is Ser or Ala; $X_{02}$ is Glu or Arg; $X_{03}$ is Ala, Glu, Gln or Cha; $X_{04}$ is Val or Glu; $X_{05}$ is Trp, Ala, Glu or Cha; $X_{06}$ is Leu, Ala, Glu or Cha; and $X_{07}$ is Leu or Glu; provided that said peptide is not hPTH(1-31)$NH_2$. The present invention also provides a method of preparing a biologically active peptide comprising introducing into a host cell such a recombinant DNA molecule, and causing expression of said molecule. In addition, the invention provides a prokaryotic or eukaryotic host cell containing the recombinant DNA molecule. In some embodiments of the present invention, the host cell is bacterial. In some embodiments of the present invention, the expression control region of the recombinant DNA molecule includes a bacterial, viral, fungal or mammalian promoter.

The present invention also provides a method of making a recombinant vector comprising inserting into a vector a nucleic acid molecule consisting essentially of a polynucleotide encoding a biologically active peptide at least 90% identical to a peptide consisting essentially of the formula: (a)

$X_{01}$ValSerGluIleGlnLeuMetHisAsnLeuGlyLysHisLeuAsnSerMet$X_{02}X_{03}X_{04}$Glu$X_{05}X_{06}$ArgLysLys$X_{07}$GlnAspVal (SEQ ID NO:1); (b) fragments thereof, containing amino acids 1-20, 1-21, 1-22, 1-23, 1-24, 1-25, 1-26, 1-27, 1-28, 1-29 or 1-30; (c) pharmaceutically acceptable salts thereof; or (d) N- or C-derivatives thereof; wherein: $X_{01}$ is Ser or Ala; $X_{02}$ is Glu or Arg; $X_{03}$ is Ala, Glu, Gln or Cha; $X_{04}$ is Val or Glu; $X_{05}$ is Trp, Ala, Glu or Cha; $X_{06}$ is Leu, Ala, Glu or Cha; and $X_{07}$ is Leu or Glu; provided that said peptide is not hPTH(1-31)NH$_2$.

The present invention further provides a method for treating mammalian conditions characterized by decreases in bone mass, wherein said method comprises administering to a subject in need thereof an effective bone mass-increasing amount of a biologically active peptide and a pharmaceutically acceptable carrier, wherein said biologically active peptide is at least 90% identical to a peptide consisting essentially of the formula: (a)) $X_{01}$ValSerGluIleGlnLeuMetHisAsnLeuGlyLysHisLeuAsnSerMet$X_{02}X_{03}X_{04}$Glu$X_{05}X_{06}$ArgLysLys$X_{07}$GlnAspVal (SEQ ID NO:1); (b) fragments thereof, containing amino acids 1-20, 1-21, 1-22, 1-23, 1-24, 1-25, 1-26, 1-27, 1-28, 1-29 or 1-30; (c) pharmaceutically acceptable salts thereof; or (d) N- or C-derivatives thereof; wherein: $X_{01}$ is Ser or Ala; $X_{02}$ is Glu or Arg; $X_{03}$ is Ala, Glu, Gln or Cha; $X_{04}$ is Val or Glu; $X_{05}$ is Trp, Ala, Glu or Cha; $X_{06}$ is Leu, Ala, Glu or Cha; and $X_{07}$ is Leu or Glu; provided that said peptide is not hPTH(1-31)NH$_2$.

In some embodiments of the present invention, the effective bone mass-increasing amount of the peptide is administered by providing to the patient DNA encoding the peptide and expressing the peptide in vivo.

The condition to be treated can be, for example, osteoporosis, including old age osteoporosis and menopausal osteoporosis.

In some embodiments of the present invention, the effective amount of the peptide for increasing bone mass is from about 0.01 μg/kg/day to about 1.0 μg/kg/day.

In some embodiments of the present invention, the method of administration of the peptide of the present invention can be, but is not limited to, parenteral, subcutaneous, or nasal insufflation.

The present invention also provides a method for determining rates of bone formation, bone resorption and/or bone remodeling comprising administering to a patient an effective amount of a biologically active peptide at least 90% identical to a peptide consisting essentially of the formula: (a) $X_{01}$ValSerGluIleGlnLeuMetHisAsnLeuGlyLysHisLeuAsnSerMet$X_{02}X_{03}X_{04}$Glu$X_{05}X_{06}$ArgLysLys$X_{07}$GlnAspVal (SEQ ID NO:1); (b) fragments thereof, containing amino acids 1-20, 1-21, 1-22, 1-23, 1-24, 1-25, 1-26, 1-27, 1-28, 1-29 or 1-30; (c) pharmaceutically acceptable salts thereof; or (d) N- or C-derivatives thereof; wherein: $X_{01}$ is Ser or Ala; $X_{02}$ is Glu or Arg; $X_{03}$ is Ala, Glu, Gln or Cha; $X_{04}$ is Val or Glu; $X_{05}$ is Trp, Ala, Glu or Cha; $X_{06}$ is Leu, Ala, Glu or Cha; and $X_{07}$ is Leu or Glu; provided that the peptide is not hPTH(1-31)NH$_2$, and determining the uptake of the peptide into the bone of the patient.

Further embodiments, features, and advantages of the present inventions, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate one or more embodiments of the present invention and, together with the description, further serve to explain the principles of the invention and to enable a person skilled in the pertinent art to make and use the invention.

FIG. 1 shows an alanine-scan of the (17-31) domain of PTH(1-31)NH$_2$. Residues in the (17-31) domain of PTH(1-31)NH$_2$ were individually replaced by alanine, and effects on binding to the intact PTHR (FIG. 1A and FIG. 1B) and to PTHR-delNt (FIG. 1C and FIG. 1D) were assessed by competition methods. Assays in FIG. 1A and FIG. 1B used stably transfected HKRK-B7 cells and $^{125}$I-[Nle$^{8,21}$,Tyr$^{34}$]rPTH(1-34)NH$_2$ {$^{125}$I-PTH(1-34)} tracer radioligand. Those in FIG. 1C and FIG. 1D used membranes prepared from COS-7 cells transiently transfected with PTHR-delNt and $^{125}$I-[Aib$^{13}$, Nle$^8$,Gln$^{10}$,Har$^{11}$,Ala$^{12}$,Trp$^{14}$,Tyr$^{15}$]PTH(1-15)NH$_2$ {$^{125}$I-[Aib$^{13}$,M]PTH(1-15)} tracer radioligand. To increase total binding of $^{125}$I-[Aib$^{13}$,M]PTH(1-15), the COS-7 cells were cotransfected with a Gα$_s$ negative-dominant mutant as described herein. Data are expressed as a percentage of the specific binding (SB) observed in the absence of unlabeled competitor ligand. The curves for the PTH(1-31) analogs shown in panels 1C and 1D were obtained by extrapolating the data to non-specific binding, determined which unlabeled [Aib$^{13}$,M]PTH(1-15) at maximum concentration. Data for the parental PTH(1-31)NH$_2$ peptide (filled circles, dashed line) are shown in each graph, and that of [Aib$^{13}$,M]PTH(1-15)NH$_2$ (open diamonds, solid line) are shown in panels 1C and 1D, for reference. Data are means (±s.e.m.) of three or more experiments, each performed in duplicate.

FIG. 2 shows the circular dichroism spectroscopy of alanine-substituted PTH(1-31)NH$_2$ analogs. The parental peptide PTH(1-31)NH$_2$ peptide and derivatives thereof altered by a single alanine substitution in the (17-31) domain were analyzed by CD spectroscopy. The negative deflections in mean-residue elipticity [θ] in the 209 nm and 222 nm regions of the spectra are indicative of α-helical structure. For each peptide, the number of helical residues per peptide chain was calculated from [θ]$_{222}$, and the resulting values are reported in Tables 1 and 2.

FIG. 3 shows cyclohexylalanine-scan of the (17-31) domain of [Ala$^1$,Arg$^{19}$]PTH(1-31)NH$_2$. Residues in the (17-31) of [Ala$^1$,Arg$^{19}$]PTH(1-31)NH$_2$ were individually replaced by cyclohexylalanine (Cha) and effects on binding to the intact PTHR (FIG. 3A and FIG. 3B) and to PTHR-delNt (FIG. 3C and FIG. 3D) were assessed, as described in the description of FIG. 1. Data are means (±s.e.m.) of three or more experiments, each performed in duplicate.

FIG. 4 shows the effects of glutamate substitutions in the (19-28) region of [Ala$^1$,Arg$^{19}$]PTH(1-31)NH$_2$. Residues in the (19-28) region of [Ala$^1$,Arg$^{19}$]PTH(1-31)NH$_2$ were replaced by glutamic acid and the effects on binding to the intact PTHR (FIG. 4A and FIG. 4B) and to PTHR-delNt (FIG. 4C and FIG. 4D) were assessed, as described in the description of FIG. 1. Data are means (±s.e.m.) combined from three or more experiments, each performed in duplicate.

FIG. 5 shows a substitution analysis of arginine-20. The effects of replacing the highly conserved arginine at position 20 of PTH(1-31)NH$_2$ by various coded (Gln, Glu, Lys) or non-encoded (Nle, Cit, Orn, Apa, Gph, and PipGly) amino acids on binding to the intact PTHR (FIG. 5A and FIG. 5B) and to PTHR-delNt (FIG. 5C and FIG. 5D) were assessed by competition methods, as described in the description of FIG. 1. Data are means (±s.e.m.) combined from three or more experiments, each performed in duplicate.

Figure 6A:
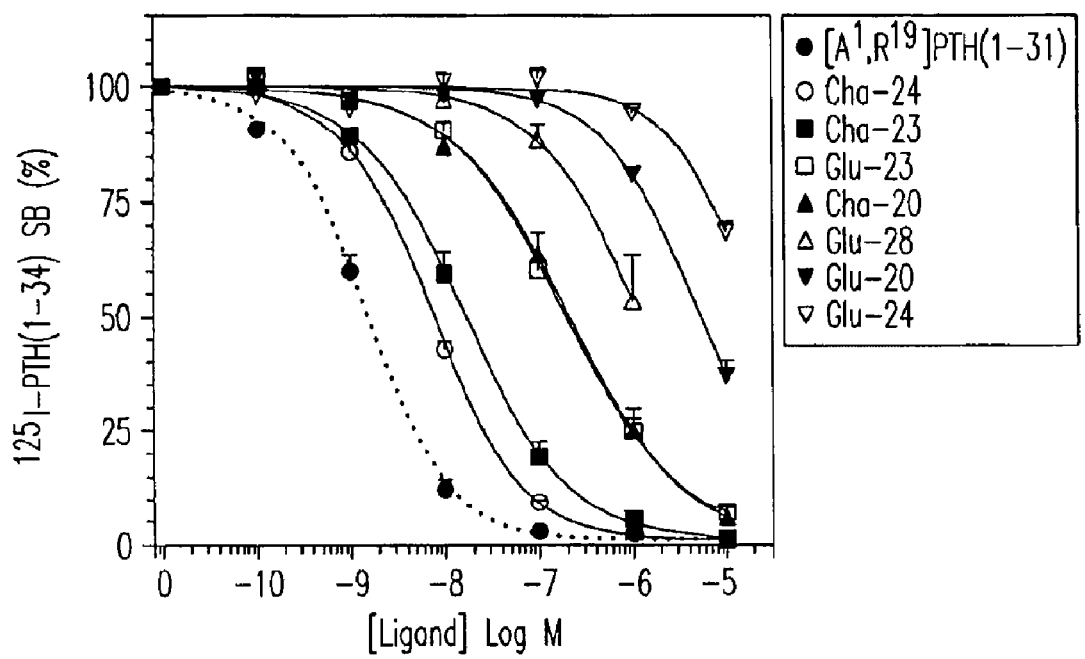
Figure 6B:
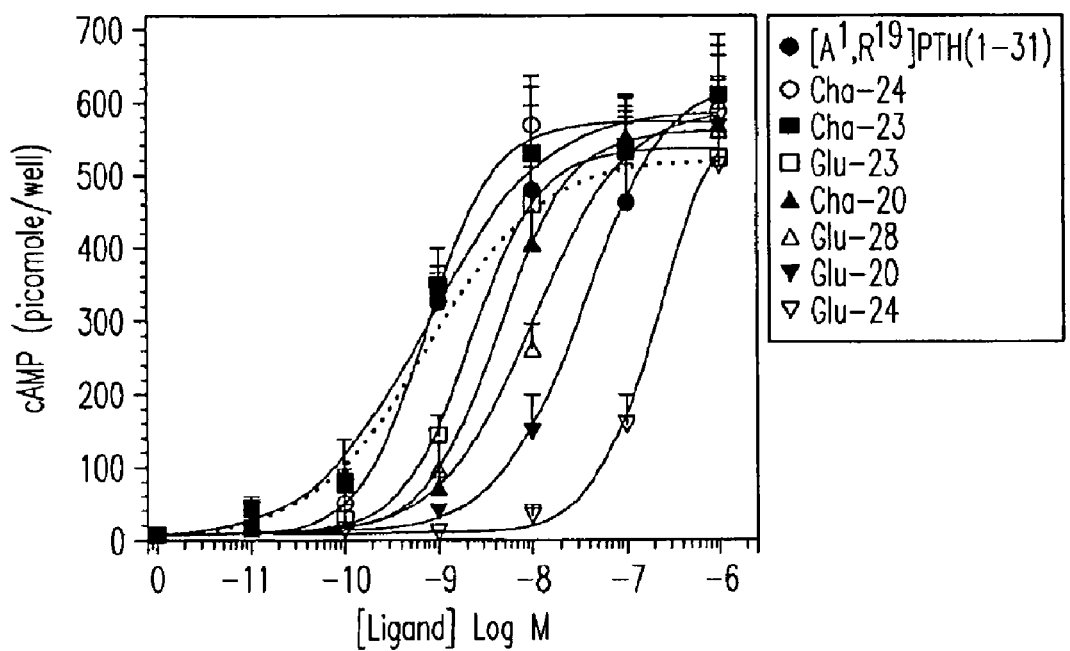

FIG. 6 shows binding and cAMP-stimulating activities in ROS 17/2.8 cells. The parental peptide [Ala$^1$,Arg$^{19}$]PTH(1-31)NH$_2$ and Glu- or Cha-substituted analogs thereof were evaluated for the capacity to bind to the endogenous PTHR in ROS 17/2.8 cells, and to stimulate cAMP formation in these cells (FIG. 6B). Competition binding studies were performed in intact cells using $^{125}$I-PTH(1-34) as a tracer radioligand (FIG. 6A). Data are means (±s.e.m.) of data combined from three experiments, each performed in duplicate.

Figure 7A:
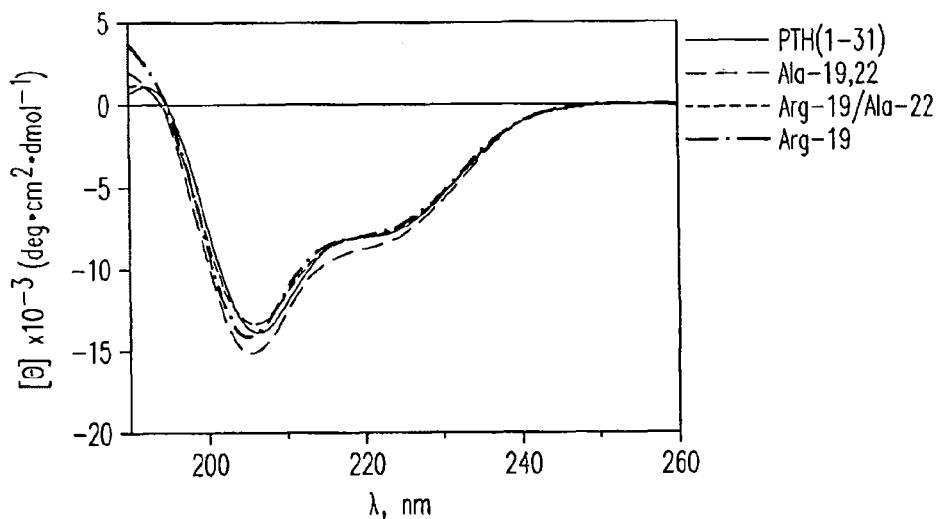
Figure 7B:
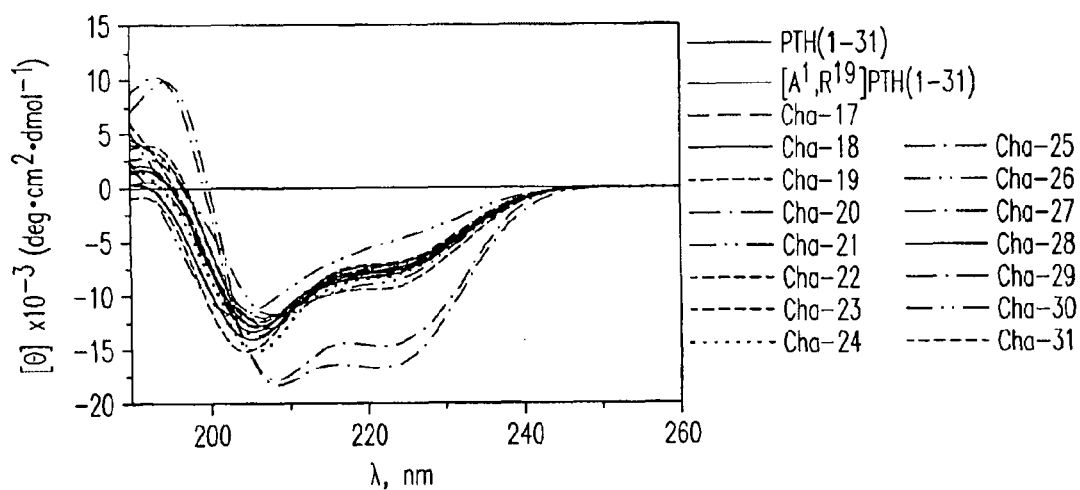
Figure 7C:
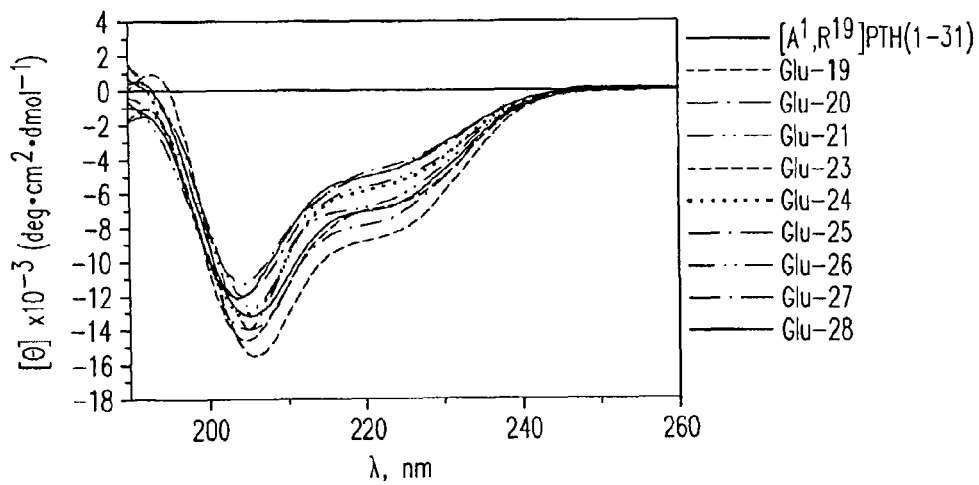

FIG. 7 shows circular dichroism spectroscopy of PTH(1-31)NH$_2$ and [Ala$^1$,Arg$^{19}$]PTH(1-31)NH$_2$ analogs. PTH(1-31)NH$_2$ and analogs thereof substituted at positions 19 and/or 22 (FIG. 7A), or [Ala$^1$,Arg$^{19}$]PTH(1-31)NH$_2$ and analogs thereof substituted in the (17-31) domain with cyclohexylalanine (FIG. 7B) or glutamic acid (FIG. 7C), were analyzed by CD spectroscopy, as described in the description of FIG. 2.

Figure 8:
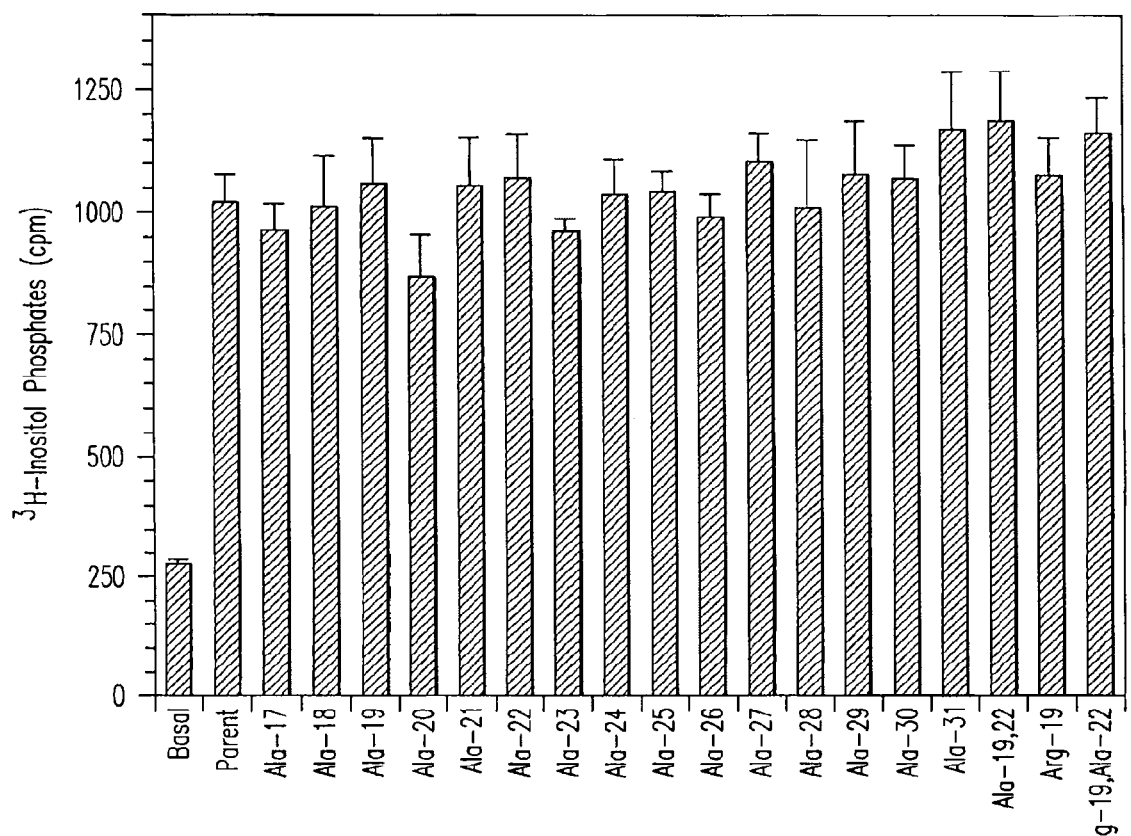

FIG. 8 shows stimulation of inositol phosphate accumulation. Intact COS-7 cells transiently transfected with the wild-type PTHR were treated with buffer alone (basal), PTH(1-31) NH$_2$ (parent), or an analog thereof containing the indicated alanine substitution, and effects on inositol phosphate accumulation were assessed. Data are means (±s.e.m.) of values from three experiments, each performed in duplicate.

DETAILED DESCRIPTION OF THE INVENTION

Definitions

In order to provide a more clear understanding of the specification and claims, the following definitions are provided.

Amino Acid Sequences: The amino acid sequences in this application use either the single letter or three letter designations for the amino acids. These designations are well known to one of skill in the art and can be found in numerous readily available references, such as for example in Cooper, G. M., The Cell 1997, ASM Press, Washington, D.C. or Ausubel et al., Current Protocols in Molecular Biology, 1994. Where substitutions in a sequence may be referred to, for example, as Ser-3→Ala, this means that the serine in the third position from the N-terminal end of the polypeptide may be replaced with another amino acid.

Biological Activity of the Protein: This expression refers to any biological activity of the polypeptide. Examples of these activities include, but are not limited to metabolic or physiologic function of compounds of the polypeptide or derivatives thereof including similar activities or improved activities or those activities with decreased undesirable side-effects. Also included are antigenic and immunogenic activities of said compounds or derivatives thereof.

Cloning vector: A plasmid or phage DNA or other DNA sequence which is able to replicate autonomously in a host cell, and which is characterized by one or a small number of restriction endonuclease recognition sites at which such DNA sequences may be cut in a determinable fashion, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

DNA construct: As used herein, "DNA construct" should be understood to refer to a recombinant, man-made DNA, either linear or circular.

Derivative or Functional Derivative: The term "derivative" or "functional derivative" is intended to include "variants," the "derivatives," or "chemical derivatives" of the PTH molecule. A "variant" of a molecule or derivative thereof is meant to refer to a molecule substantially similar to either the entire molecule, or a fragment thereof. An "analog" of a molecule or derivative thereof is meant to refer to a non-natural molecule substantially similar to either the molecules or fragments thereof.

PTH derivatives contain changes in the polypeptide relative to the native PTH polypeptide of the same size. A molecule is said to be "substantially similar" to another molecule if the sequence of amino acids in both molecules is substantially the same, and if both molecules possess a similar biological activity. Thus, two molecules that possess a similar activity, may be considered variants, derivatives, or analogs as that term is used herein even if one of the molecules contains additional amino acid residues not found in the other, or if the sequence of amino acid residues is not identical. PTH derivatives, however, need not have substantially similar biological activity to the native molecule. In some instances PTH derivatives may have substantially different activity than the native PTH. For example, a derivative may be either an antagonist or an agonist of the PTH receptor.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in Remington's Pharmaceutical Sciences (1980) and will be apparent to those of ordinary skill in the art.

Expression vector: As used herein, an "expression vector" is a DNA construct that contains a structural gene operably linked to an expression control sequence so that the structural gene can be expressed when the expression vector is transformed into an appropriate host cell. Two DNA sequences are said to be "operably linked" if the biological activity of one region will affect the other region and also if the nature of the linkage between the two DNA sequences does not (1) result in the introduction of a frame-shift mutation, (2) interfere with the ability of the promoter region sequence to direct the transcription of the desired sequence, or (3) interfere with the ability of the desired sequence to be transcribed by the promoter region sequence. Thus, a promoter region would be operably linked to a desired DNA sequence if the promoter were capable of effecting transcription of that desired DNA sequence.

Fragment: A "fragment" of a molecule such as for example, SEQ ID NO: 1 or derivative thereof is meant to refer to any polypeptide subset of these molecules.

Fusion protein: By the term "fusion protein" is intended a fused protein comprising compounds such as for example, SEQ ID NO: 1 or derivatives thereof, either with or without a "selective cleavage site" linked at its N-terminus, which is in turn linked to an additional amino acid leader polypeptide sequence.

Gene therapy: As used herein, "gene therapy" means, inter alia, the ability to ameliorate, eliminate or attenuate a defect or disease by altering a gene of interest or the product expressed by the gene of interest, by altering the genotype of the cell or organism of interest or by altering the normal pattern of gene expression of an organism. For example, this may be accomplished by replacing the gene of interest with a mutated gene, knocking out the gene of interest or inserting a different gene that produces a product that inhibits or stimulates the gene of interest or using other methods known to those of skill in the art. Generally, a recombinant polynucleotide is introduced into cells or tissues of an organism to effect a change in gene expression. The manipulation of the genetic material may be accomplished either in vivo or ex vivo. The above examples are not meant to limit the different ways in which the gene therapy may be effected. Any techniques known to those of skill in the art of gene therapy may be used with the claimed invention.

Host Animal: The term transgenic animals refers to those animals whose germ and somatic cells contain a DNA construct of the invention. Such transgenic animals are in general vertebrates. Preferred host animals are mammals such as non-human primates, mice, sheep, pigs, cattle, goats, guinea pigs, rodents, e.g. rats, and the like. The term "host animal" also includes animals in all stages of development, including embryonic and fetal stages.

% Identity: Whether any two polypeptides or polynucleotides are for example, at least 90% "identical" can be determined using known computer algorithms such as the "FAST A" program, using for example, the default parameters as in Pearson and Lipman, *Proc. Natl. Acad. Sci. USA* 85:2444 (1988). Alternatively the BLAST function of the National Center for Biotechnology Information database may be used to determine identity.

The terms homology and identity are often used interchangeably. In this regard, percent homology or identity may be determined by methods known to those of skill in the art. For example, by comparing sequence information using a GAP computer program, version 6.0, available from the University of Wisconsin Genetics Computer Group (UWGCG). The GAP program utilizes the alignment method of Needleman and Wunsch (J. Mol. Biol. 48:443 (1970), as revised by Smith and Waterman (Adv. Appl. Math. 2:482 (1981). Briefly, the GAP program defines similarity as the number of aligned symbols (i.e., nucleotides or amino acids) which are similar, divided by the total number of symbols in the shorter of the two sequences.

In general, sequences are aligned so that the highest order match is obtained. "Identity" per se has an art-recognized meaning and can be calculated using published techniques. (See, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., SIAM *J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., SIAM J Applied Math 48:1073 (1988). Methods to determine identity and similarity are codified in computer programs. Preferred computer program methods to determine identity and similarity between two sequences include, but are not limited to, GCG program package (Devereux, J., et al., Nucleic Acids Research 12(i):387 (1984)), BLASTP, BLASTN, FASTA (Atschul, S. F., et al., *J Molec Biol* 215:403 (1990)).

Therefore, as used herein, the term "identity" represents a comparison between a test and a reference polypeptide or polynucleotide. More specifically, a test polypeptide may be defined as any polypeptide that is 90% or more identical to a reference polypeptide. As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids, that no more than 10% (i.e., 10 out of 100) amino acids in the test polypeptides differ from that of the reference polypeptides. Such differences may be represented as point mutations randomly distributed over the entire length of the amino acid sequence of the invention or they may be clustered in one or more locations of varying length up to the maximum allowable amino acid difference (approximately 90% identity). Differences are defined as amino acid substitutions, or deletions.

Isolated: A term meaning altered from the natural state. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of compounds of for example SEQ ID NO:1 and derivatives thereof can be substantially purified by the one-step method described in Smith and Johnson, *Gene* 67:31 40 (1988). The terms isolated and purified are sometimes used interchangeably.

By "isolated" is meant that the DNA is free of the coding sequences of those genes that, in the naturally-occurring genome of the organism (if any) from which the DNA of the invention is derived, immediately flank the gene encoding the DNA of the invention. The isolated DNA may be single-stranded or double-stranded, and may be genomic DNA, cDNA, recombinant hybrid DNA, or synthetic DNA. It may be identical to a native DNA sequence encoding compounds of for example, SEQ ID NO:1 and derivatives thereof, or may differ from such sequence by the deletion, addition, or substitution of one or more nucleotides. Single-stranded DNAs of the invention are generally at least 8 nucleotides long, (preferably at least 18 nucleotides long, and more preferably at least 30 nucleotides long) ranging up to full length of the DNA molecule encoding compounds of SEQ ID NO:1 and derivatives thereof; they preferably are detectably labeled for use as hybridization probes, and may be antisense.

Isolated or purified as it refers to preparations made from biological cells or hosts should be understood to mean any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. The procedures may include for example, but are not limited to, ammonium sulfate fractionation, gel filtration, ion exchange change chromatography, affinity chromatography, density gradient centrifugation and electrophoresis.

A preparation of DNA or protein that is "pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

Leader Sequence: By the term "leader sequence" is intended a polynucleotide sequence linked to compounds of for example, SEQ ID NO: 1, and expressed in host cells as a fusion protein fused to the selective cleavage site and compounds of SEQ ID NO: 1. The term "leader polypeptide" describes the expressed form of the "leader sequence" as obtained in the fusion protein.

The fusion protein, which is often insoluble and found in inclusion bodies when it is overexpressed, is purified from other bacterial protein by methods well known in the art. In a preferred embodiment, the insoluble fusion protein is centrifuged and washed after cell lysis, and resolubilized with guanidine-HCl. It can remain soluble after removal of the denaturant by dialysis. (For purification of refractile proteins, see Jones, U.S. Pat. No. 4,512,922; Olson, U.S. Pat. No. 4,518,526; and Builder et al., U.S. Pat. Nos. 4,511,502 and 4,620,948).

The recombinantly produced compounds of for example, SEQ ID NO: 1 or derivatives thereof can be purified to be substantially free of natural contaminants from the solubilized fusion protein through the use of any of a variety of methodologies. As used herein, a compound is said to be "substantially free of natural contaminants" if it has been substantially purified from materials with which it is found following expression in bacterial or eukaryotic host cells. Compounds of SEQ ID NO: 1 or derivatives thereof may be purified through application of standard chromatographic separation technology.

Alternatively, the peptide may be purified using immunoaffinity chromatography (Rotman, A. et al., *Biochim. Biophys. Acta* 641:114 121 (1981); Sairam, M. R. J, Chromatog 215:143 152 (1981); Nielsen, L. S. et al., Biochemistry 21:6410 6415 (1982); Vockley, J. et al., *Biochem. J.* 217:535 542 (1984); Paucha, E. et al., *J. Virol.* 51:670 681 (1984); and Chong, P. et al., *J. Virol. Meth.* 10:261 268 (1985)).

After partial or substantial purification, the fusion protein is treated enzymatically with the enzyme corresponding to the cleavage site. Alternatively, the fusion protein in its more impure state, even in refractile form, can be treated with the enzyme. If needed, the resulting mature compounds of for example, SEQ ID NO: 1 or derivatives thereof, can be further purified. Conditions for enzymatic treatment are known to those of skill in the art.

Operably Linked: Two DNA sequences (such as a promoter region sequence and a sequence encoding a PTH derivative) are said to be operably linked if the nature of the linkage between the two DNA sequences does not (1) result in the introduction of a frame-shift mutation, (2) interfere with the ability of the promoter region sequence to direct the transcription of the desired sequence, or (3) interfere with the ability of the desired sequence to be transcribed by the promoter region sequence. Thus, a promoter region would be operably linked to a desired DNA sequence if the promoter were capable of effecting transcription of that DNA sequence.

Polynucleotide: This term generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

Polypeptide: Polypeptide and peptide are used interchangeably. The term polypeptide refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids and include amino acid sequences modified either by natural processes, such as post-translational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched and they may be cyclic, with or without branching. Cyclic, branched and branched cyclic polypeptides may result from post-translational modifications or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins-Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al, "Analysis for protein modifications and nonprotein cofactors", *Methods in Enzymol.* 182:626 646 (1990) and Rattan et al., "Protein Synthesis: Posttranslational Modifications and Aging", *Ann NY Acad Sci* 663:48 62 (1992).

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. Examples of promoters include the CMV promoter (Invitrogen, San Diego, Calif.), the SV40, MMTV, and hMTIIa promoters (U.S. Pat. No. 5,457,034), the HSV-1 4/5 promoter (U.S. Pat. No. 5,501,979), and the early intermediate HCMV promoter (WO92/17581). Also, tissue-specific enhancer elements may be employed. Additionally, such promoters may include tissue and cell-specific promoters of an organism.

Recombinant Host: According to the invention, a recombinant host may be any prokaryotic or eukaryotic host cell which contains the desired cloned genes on an expression vector or cloning vector. This term is also meant to include those prokaryotic or eukaryotic cells that have been genetically engineered to contain the desired gene(s) in the chromosome or genome of that organism. For examples of such hosts, see Sambrook et al., Molecular Cloning: A Laboratory Manual, Second Edition, Cold Spring Harbor Laboratory, Cold Spring Harbor, N.Y. (1989). Preferred recombinant hosts are eukaryotic cells transformed with the DNA construct of the invention. More specifically, mammalian cells are preferred.

Selective cleavage site: The term "selective cleavage site" refers to an amino acid residue or residues which can be selectively cleaved with either chemicals or enzymes in a predictable manner. A selective enzyme cleavage site is an amino acid or a peptide sequence which is recognized and hydrolyzed by a proteolytic enzyme. Examples of such sites include, without limitation, trypsin or chymotrypsin cleavage sites.

Stringent Hybridization. As used herein "stringent hybridization" conditions should be understood to be those conditions normally used by one of skill in the art to establish at least a 95% homology between complementary pieces of DNA or DNA and RNA.

There are only three requirements for hybridization to a denatured strand of DNA to occur. (1) There must be complementary single strands in the sample. (2) The ionic strength of the solution of single-stranded DNA must be fairly high so that the bases can approach one another; operationally, this means greater than 0.2M. (3) The DNA concentration must be high enough for intermolecular collisions to occur at a reasonable frequency. The third condition only affects the rate, not whether renaturation/hybridization will occur.

Conditions routinely used by those of skill in the art are set out in readily available procedure texts, e.g., Ausubel. F. et al., Current Protocols in Molecular Biology, Vol. I, Chap. 2.10, John Wiley & Sons, Publishers (1994) or Sambrook et al., Molecular Cloning, Cold Spring Harbor (1989), the entire documents incorporated herein by reference. As would be known by one of skill in the art, the ultimate hybridization stringency reflects both the actual hybridization conditions as well as the washing conditions following the hybridization, and one of skill in the art would know the appropriate manner in which to change these conditions to obtain a desired result.

For example, a prehybridization solution should contain sufficient salt and nonspecific DNA to allow for hybridization to non-specific sites on the solid matrix, at the desired temperature and in the desired prehybridization time. For example, for stringent hybridization, such prehybridization solution could contain 6× sodium chloride/sodium citrate (1×SSC is 0.15 M NaCl, 0.015 M Na citrate; pH 7.0), 5× Denhardt's solution, 0.05% sodium pyrophosphate and 100 µg per ml of herring sperm DNA. An appropriate stringent hybridization mixture might then contain 6×SSC, 1× Denhardt's solution, 100 µg per ml of yeast tRNA and 0.05% sodium pyrophosphate.

Alternative conditions for DNA-DNA analysis could entail the following: 1) prehybridization at room temperature and hybridization at 68° C.; 2) washing with 0.2×SSC/0.1% SDS at room temperature; 3) as desired, additional washes at 0.2× SSC/0.1% SDS at 42° C. (moderate-stringency wash); or 4) as desired, additional washes at 0.1×SSC/0.1% SDS at 68° C. (high stringency).

Known hybridization mixtures, e.g., that of Church and Gilbert, Proc. Natl. Acad. Sci. USA 81:1991 1995 (1984), comprising the following composition may also be used: 1% crystalline grade bovine serum albumin/1 mM EDTA/0.5M $NaHPO_4$, pH 7.2/7% SDS. Additionally, alternative but similar reaction conditions can also be found in Sambrook et al., Molecular Cloning, Cold Spring Harbor (1989). Formamide may also be included in prehybridization/hybridization solutions as desired. The invention may include DNA sequences that stringently hybridize to nucleic acid sequences encoding PTH derivatives.

Transgenic: As used herein, a "transgenic" organism is an organism containing a transgene, wherein the transgene was introduced into the organism or an ancestor of the organism at a prenatal stage, e.g., an embryonic stage. The transgene results in a defined change to its germ line, wherein the change is not ordinarily found in wild-type organisms. This change can be passed on to the organism's progeny and therefore the progeny are also transgenic animals. The change to the organism's germ line can be an insertion, a substitution, or a deletion in the gene of interest. Non-human animals are organisms into which transgenes may be introduced by techniques known in the art, such animals include but are not limited to mice, goats, sheep, pigs, cows and other domestic farm animals. Methods for generating transgenic animals have become convention in the art and are described, for example, in Hogan B. et al., "A Laboratory Manual, Cold Spring Harbor, N.Y. (1986) or U.S. Pat. No. 5,922,927 or 5,917,123. A transgenic animal that carries one transgene can be further bred to another transgenic animal carrying a second transgene to create a "double transgenic" animal carrying two transgenes.

Compounds of the Invention

Frequently in this section, reference is made to the polypeptide of SEQ ID NO:1. This is merely illustrative and should not be meant to imply that this is limiting in any way relative to the other polypeptide sequences of the invention. As protein products, compounds of the invention are amenable to production by the techniques of solution- or solid-phase peptide synthesis or recombinant biology.

The solid phase peptide synthesis technique, in particular, has been successfully applied in the production of human PTH and can be used for the production of compounds of SEQ ID NO: 1, derivatives thereof (for guidance, see Kimura et al., supra, and see Fairwell et al., Biochem. 22:2691 (1983)). Success with producing human PTH on a relatively large scale has been reported by Goud et al., in J. Bone Min. Res. 6:781 (1991), incorporated herein by reference. The synthetic peptide synthesis approach generally entails the use of automated synthesizers and appropriate resin as solid phase, to which is attached the C-terminal amino acid of the desired compounds of SEQ ID NO: 1 or derivatives thereof. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of such as for example, SEQ ID NO: 1 and derivatives thereof which incorporate amino acids that are not genetically encoded, such as cyclohexylalanine (Cha).

In one aspect of the invention, any amino-acid substitutions at positions 17-31 of PTH, particularly those amino acid substitutions at amino acid positions 19, 20, 21, 23, 24, 25, 26, 27, 28, and/or 31, and more particularly those amino acid substitutions at amino acid positions 20, 21, 23, 24, and/or 28, which do not destroy the biological activity of the PTH polypeptide to antagonize or agonize the PTH-1/PTH-2 receptor (as determined by assays known to the skilled artisan and discussed herein), are also included within the scope of the present invention.

The synthetic analog of bovine PTH, PTH(3-34) has been recognized as a potent PTH antagonist in vitro. Variants of PTH lacking N-terminal amino acids 1-2 and 1-7, were shown to be devoid of agonist activity and capable of antagonist activity (Born, W. et al., *Endocrinol.* 23:1848-1853 (1988)). Preferred potential antagonist variants of SEQ ID NO: 1 of this invention are variants truncated at the N-terminus.

In accordance with another aspect of the present invention, substituents may be attached to the free amine of the N-terminal amino acid of compounds such as, for example, SEQ ID NO: 1 or derivatives thereof by standard methods known in the art. For example, alkyl groups, e.g., $C_{1-12}$ alkyl, may be attached using reductive alkylation. Hydroxyalkyl groups, e.g. $C_{1-12}$ hydroxyalkyl, may also be attached using reductive alkylation wherein the free hydroxy group is protected with a t-butyl ester. Acyl groups, e.g., $COE_1$, may be attached by coupling the free acid, e.g., $E_1COOH$, to the free amino of the N-terminal amino acid. Additionally, possible chemical modifications of the C-terminal end of the polypeptide are encompassed within the scope of the invention. These modifications may modify binding affinity to the receptor.

Also contemplated within the scope of this invention are those compounds such as for example, SEQ ID NO:1 and derivatives thereof that alter secondary or tertiary structure, or stability of compounds such as SEQ ID NO: 1 or derivatives thereof which still retain biological activity. Such derivatives might be achieved through lactam cyclization, disulfide bonds, or other means known to a person of ordinary skill in the art.

The peptides of the invention may also be labeled. The labeling molecule may be selected from a group including a chromogen, a catalyst, an enzyme, a fluorescent label, a chemiluminescent label, a bioluminescent label, a paramagnetic ion, a radioisotope including other nuclear tags and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

Routinely used radiolabels include radiolabels $^3H$, $^{125}I$, $^{35}S$, $^{14}C$ and $^{32}P$. Techniques to incorporate radioisotopes are well known in the art. (See, Current Protocols in Protein Science, Coligan et al. eds., John Wiley Sons Inc. 2002)

A large number of enzymes suitable for use as labeling molecules is disclosed in U.S. Pat. Nos. 4,366,241, 4,843,000, and 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorescent labels (or fluorochromes) include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al., International Publication No. WO 93/06121. Reference also may be made to the fluorochromes described in U.S. Pat. No. 5,573,909 (Singer et al), U.S. Pat. No. 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

Vectors, Host Cells, and Recombinant Expressions

The present invention also relates to vectors that comprise a polynucleotide of the present invention, and host cells which are genetically engineered with vectors of the invention and the production of polypeptides of the invention by recombinant techniques. Cell-free translation systems can also be employed to produce such proteins using RNAs derived from the DNA constructs of present invention.

For recombinant production, host cells can be genetically engineered to incorporate expression systems or portions thereof for polynucleotides of the present invention. Introduction of polynucleotides into host cells can be effected by methods described in many standard laboratory manuals, (such as Davis et al., *Basic Methods in Molecular Biology* (1986) and Sambrook et al., *Molecular Cloning: A Laboratory Manual*, 2nd Ed., Cold Spring Harbor Laboratory Press, Cold Spring Harbor, N.Y. (1989)), such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *Streptococci, Staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *Molecular Cloning: A Laboratory Manual* (Supra).

RNA vectors may also be utilized for the expression of the nucleic acids encoding compounds of the invention or derivatives thereof disclosed in this invention. These vectors are based on positive or negative strand RNA viruses that naturally replicate in a wide variety of eukaryotic cells (Bredenbeek, P. J. & Rice, C. M., *Virology* 3: 297-310, 1992). Unlike retroviruses, these viruses lack an intermediate DNA lifecycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., *TIBTECH* 11:18-22, 1993; Frolov, I., et al., *Proc. Natl. Acad. Sci.* (*USA*) 93: 11371-11377, 1996). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

For secretion of the translated protein into the lumen of the endoplasmic reticulum, into the periplasmic space or into the extracellular environment appropriate secretion signals may be incorporated into the desired polypeptide. These signals may be endogenous to the polypeptide or they may be heterologous signals.

The expression of a DNA sequence requires that the DNA sequence be "operably linked" to DNA sequences which contain transcriptional and translational regulatory information. An operable linkage is a linkage in which the control or regulatory DNA sequences and the DNA sequence sought to be expressed are connected in such a way as to permit gene expression. The precise nature of the "control regions" needed for gene expression may vary from organism to organism, but shall in general include a promoter region which, in prokaryotic cells, contains both the promoter (which directs the initiation of RNA transcription) as well as DNA sequences which, when transcribed into RNA, will signal the initiation of protein synthesis. Regulatory regions in eukaryotic cells will in general include a promoter region sufficient to direct the initiation of RNA synthesis.

The joining of various DNA fragments, to produce the expression vectors of this invention is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligates. In the case of a fusion protein, the genetic construct encodes an inducible promoter which is operably linked to the 5' gene sequence of the fusion protein to allow efficient expression of the fusion protein.

To express compounds of the invention or a derivative thereof in a prokaryotic cell (such as, for example, *E. coli, B. subtilis, Pseudomonas, Streptomyces*, etc.), it is necessary to operably link, for example, the SEQ ID NO: 1-encoding DNA sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pBR325, etc. Examples of inducible prokaryotic promoters include the major right and left promoters of bacteriophage λ (PL and PR), the trp, recA, lacZ, lacI, and gal promoters of *E. coli*, the α-amylase (Ulmanen, I. et al., *J. Bacteriol.* 162:176-182 (1985)), and the σ-28-specific promoters of *B. subtilis* (Gilman, M. Z. et al., *Gene* 32: 1-20 (1984)), the promoters of the bacteriophages of *Bacillus* (Gryczan, T. J., In: *The Molecular Biology of the Bacilli*, Academic Press, Inc., NY (1982)), and *Streptomyces* promoters (Ward, J. M. et al., *Mol. Gen. Genet.* 203:468-478 (1986)). Prokaryotic promoters are reviewed by Glick, B. R., *J. Ind. Microbiol.* 1:277-282 (1987); Cenatiempo, Y., *Biochimie* 68:505-516 (1986)); and Gottesman, S., *Ann. Rev. Genet.* 18:415-442 (1984)).

The preferred prokaryotic promoter for this invention is the *E. coli* tip promoter, which is inducible with indole acrylic acid.

If expression is desired in a eukaryotic cell, such as yeast, fungi, mammalian cells, or plant cells, then it is necessary to employ a promoter capable of directing transcription in such a eukaryotic host. Preferred eukaryotic promoters include the promoter of the mouse metallothionein I gene (Hamer, D. et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature* (*London*) 290:304-310 (1981)); and the yeast gal4 gene promoter (Johnston, S. A., et al., *Proc. Natl. Acad. Sci.* (*USA*) 79:6971-6975 (1982); Silver, P. A., et al., *Proc. Natl. Acad. Sci.* (*USA*) 81:5951-5955 (1984)).

Preferably, the introduced gene sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColE1, pSC101, pACYC 184, πVX. Such plasmids are, for example, disclosed by Maniatis, T., et al., In: *Molecular Cloning, A Laboratory Manual*, Cold Spring Harbor Press, Cold Spring Harbor, N.Y. (1982)). Preferred plasmid expression vectors include the pGFP-1 plasmid described in Gardena et al., *J. Biol. Chem.* 265:15854-15859 (1989), or a modified plasmid based upon one of the pET vectors described by Studier and Dunn, *Methods in Enzymology* 185: 60-89 (1990). *Bacillus* plasmids include pC194, pC221, pT127, etc. Such plasmids are disclosed by Gryczan, T. In: *The Molecular Biology of the Bacilli*, Academic Press, NY pp. 307-329 (1982). Suitable *Streptomyces* plasmids include pIJIOI (Kendall, K. J. et al., *J. Bacteriol.* 169:4177-4183 (1987)), and *streptomyces* bacteriophages such as ΦC31 (Chater, K. F. et al., In: *Sixth International Symposium on Actinomycetales Biology*, Akademiai Kaido, Budapest, Hungary, pp. 45-54 (1986)). *Pseudomonas* plasmids are reviewed by John, J. F. et al., *Rev. Infect. Dis.* 8:693-704 (1986)), and Izaki, K., *Jon. J. Bacteriol.* 33:729-742 (1978)).

Preferred eukaryotic expression vectors include, without limitation, BPV, vaccinia, 2-micron circle etc. Such expression vectors are well known in the art (Botstein, D., et al., *Miami Wntr. Symp.* 19:265-274 (1982); Broach, J. R., In: *The Molecular Biology of the Yeast Saccharomyces: Life Cycle and Inheritance*, Cold Spring Harbor Laboratory, Cold Spring Harbor, N.Y. pp. 445-470 (1981); Broach, J. R., *Cell* 28:203-204 (1982); Bollon, D. P., et al., *J. Clin. Hematol. Oncol.* 10:39-48 (1980); Maniatis, T., In: *Cell Biology: A Comprehensive Treatise, Vol. 3*, Gene Expression, Academic Press, NY, pp. 563-608 (1980)).

In addition to microorganisms, cultures of cells derived from multicellular organisms may also be used as hosts. In principle, any such cell culture is workable, whether from vertebrate or invertebrate cellular sources. Interest, however, has been greater with cells from vertebrate sources. Examples of useful vertebrate host cell lines are VERO and HeLa cells, Chinese hamster ovary (CHO) cell lines, WI38, BHK, COS-7, and MDCK cell lines. Expression vectors for such cells ordinarily include (if necessary) an origin of replication, a promoter located in front of or upstream to the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Simian Virus 40 (SV40) and cytomegalovirus. The early and late promoters of SV40 virus are particularly useful because both are obtained easily from the virus as a fragment which also contains the SV40 vial origin of replication (Fiers et al., Nature 273:113 (1978)).

An origin of replication may be provided either by construction of the vector to include an exogenous origin, such as may be derived from SV40 or other viral (e.g. Polyoma, Adeno, VSV, BPV) source or may be provided by the host cell chromosomal replication mechanism. If the vector is integrated into the host cell chromosome, the latter is often sufficient.

If cells without formidable cell membrane barriers are used as host cells, transfection is carried out by the calcium phosphate precipitation method as described by Graham and Van der Erb, Virology 52:546 (1978). However, other methods for introducing DNA into cells, such as by nuclear injection or by protoplast fusion may also be used. In the case of gene therapy, the direct naked plasmid or viral DNA injection method, with or without transfection-facilitating agents such as, without limitation, liposomes, provides an alternative approach to the current methods of in vivo or in vitro transfection of mammalian cells. If prokaryotic cells or cells which contain substantial cell wall constructions are used, the preferred method of transfection is calcium treatment, using calcium chloride as described in Cohen et al., Proc. Natl. Acad. Sci. USA 69:2110 (1972).

Gene Therapy

A patient (human or non-human) suffering from symptoms of a disease such as osteoporosis or other diseases requiring PTH may be treated by gene therapy. By undertaking this approach, there should be an attenuation of the disease symptoms. Gene therapy has proven effective or has been considered to have promise in the treatment of certain forms of human hemophilia (Bontempo, F. A., et al., Blood 69:1721-1724 (1987); Palmer, T. D., et al., Blood 73:438-445 (1989); Axelrod, J. H., et al., Proc. Natl. Acad. Sci. USA 87:5173-5177 (1990); Armentano, D., et al., Proc. Natl. Acad. Sci. USA 87:6141-6145 (1990)), as well as in the treatment of other mammalian diseases such as cystic fibrosis (Drumm, M. L., et al., Cell 62:1227-1233 (1990); Gregory, R. J., et al., Nature 347:358-363 (1990); Rich, D. P., et al., Nature 347:358-363 (1990)), Gaucher disease (Sorge, J., et al., Proc. Natl. Acad. Sci. USA 84:906-909 (1987); Fink, J. K., et al., Proc. Natl. Acad. Sci. USA 87:2334-2338 (1990)), muscular dystrophy (Partridge, T. A., et al., Nature 337:176-179 (1989); Law, P. K., et al., Lancet 336:114-115 (1990); Morgan, J. E., et al., J. Cell Biol. 111:2437-2449 (1990)), and metastatic melanoma (Rosenberg, S. A., et al., Science 233:1318-1321 (1986); Rosenberg, S. A., et al., N. Eng. J. Med. 319:1676-1680 (1988); Rosenberg, S. A., et al., N. Eng. J. Med. 323:570-578 (1990)). More recently, gene therapy has been shown to provide anticancer or antitumor activity in patients with prostate cancer (Herman, J. R. et al., Hum. Gene Ther. 10:1239-1249 (1999) and metastatic melanoma (Nemunaitis, J. et al., Hum. Gene. Ther. 20:1289-1298 (1999)).

Additionally, several patents have issued to methods of gene therapy. For example, U.S. Pat. Nos. 5,836,905, 5,741,486, 5,871,486 and 5,656,465.

In a preferred approach, a polynucleotide having the nucleotide sequence for the PTH polypeptide derivative may be incorporated into a vector suitable for introducing the nucleic acid molecule into cells of the mammal to be treated, to form a transfection vector.

A variety of vectors have been developed for gene delivery and possible gene therapy. Suitable vectors for this purpose include retroviruses, adenoviruses and adeno associated viruses (AAV). Alternatively, the nucleic acid molecules of the invention may be complexed into a molecular conjugate with a virus (e.g., an adenovirus) or with viral components (e.g., viral capsid proteins). The vectors derive from herpes simplex virus type 1 (HSV-1), adenovirus, adeno-associated virus (AAV) and retrovirus constructs (for review see Friedmann, T., Trends Genet 10:210-214 (1994); Jolly, D., Cancer Gene Therapy 1 (1994); Mulligan, R. C., Science 260:926-932 (1993); Smith, F. et al., Rest. Neurol. Neurosci. 8:21-34 (1995)). Vectors based on HSV-1, including both recombinant virus vectors and amplicon vectors, as well as adenovirus vectors can assume an extrachromosomal state in the cell nucleus and mediate limited, long term gene expression in postmitotic cells, but not in mitotic cells. HSV-1 amplicon vectors can be grown to relatively high titers ($10^7$ transducing units/ml) and have the capacity to accommodate large fragments of foreign DNA (at least 15 kb, with 10 concatemeric copies per virion). AAV vectors (rAAV), available in comparable titers to amplicon vectors, can deliver genes (<4.5 kb) to postmitotic, as well as mitotic cells in combination with adenovirus or herpes virus as helper virus. Long term transgene expression is achieved by replication and formation of "episomal" elements and/or through integration into the host cell genome at random or specific sites (for review see Samulski, R. J., Current Opinion in Genetics and Development 3:74-80 (1993); Muzyczka, N., Curr. Top. Microbiol. Immunol. 158:97-129 (1992)). HSV, adenovirus and rAAV vectors are all packaged in stable particles. Retrovirus vectors can accommodate 7-8 kb of foreign DNA and integrate into the host cell genome, but only in mitotic cells, and particles are relatively unstable with low titers. Recent studies have demonstrated that elements from different viruses can be combined to increase the delivery capacity of vectors. For example, incorporation of elements of the HIV virion, including the matrix protein and integrase, into retrovirus vectors allows transgene cassettes to enter the nucleus of non-mitotic, as well as mitotic cells and potentially to integrate into the genome of these cells (Naldini, L. et al., Science 272:263-267 (1996)); and inclusion of the vesicular somatitis virus envelope glycoprotein (VSV-G) increases stability of retrovirus particles (Emi, N. et al., J. Virol. 65:1202-1207 (1991)).

HSV-1 is a double-stranded DNA virus which is replicated and transcribed in the nucleus of the cell. HSV-1 has both a lytic and a latent cycle. HSV-1 has a wide host range, and infects many cell types in mammals and birds (including chicken, rat, mice monkey, and human) Spear et al., DNA Tumor Viruses, J. Tooze, Ed. (Cold Spring Harbor Laboratory, Cold Spring Harbor, N.Y., 1981, pp. 615-746). HSV-1 can lytically infect a wide variety of cells including neurons, fibroblasts and macrophages. In addition, HSV-1 infects postmitotic neurons in adult animals and can be maintained indefinitely in a latent state. Stevens, Current Topics in Microbiology and Immunology 70:31 (1975). Latent HSV-1 is capable of expressing genes.

AAV also has a broad host range and most human cells are thought to be injectable. The host range for integration is believed to be equally broad. AAV is a single stranded DNA parvovirus endogenous to the human population, making it a suitable gene therapy vector candidate. AAV is not associated with any disease, therefore making it safe for gene transfer applications (Cukor et al., *The Parvoviruses*, Ed. K. I. Berns, Plenum, N.Y., (1984) pp. 33-36; Ostrove et al., *Virology* 113: 521 (1981)). AAV integrates into the host genome upon infection so that transgenes can be expressed indefinitely (Kotin et al., *Proc. Natl. Acad. Sci. USA* 87: 221 (1990); Samulski et al., *Embo J.* 10: 3941 (1991)). Integration of AAV into the cellular genome is independent of cell replication which is particularly important since AAV can thus transfer genes into quiescent cells (Lebkowski et al., *Mol. Cell. Biol.* 8:3988 (1988)).

Both HSV and AAV can deliver genes to dividing and non-dividing cells. In general, HSV virions are considered more highly infectious that AAV virions, with a ratio of virus particles: infectious units in the range of 10 for HSV (Browne, H. et al., *J. Virol.* 70:4311-4316 (1996)) and up to thousands for AAV (Snyder, R. O. et al., In *Current Protocols in Human Genetics*, Eds. Dracopoli, N. et al., John Wiley and Sons: New York (1996), pp. 1-24), and both having a broad species range. Still, each virion has specific trophisms which will affect the efficiency of infection of specific cell types. The recent identification of a membrane receptor for HSV-1 which is a member of the tumor necrosis factor alpha family (Montgomery, R. I. et al., 21st Herpes Virus Workshop Abstract #167 (1996)) indicates that the distribution of this receptor will affect the relative infectability of cells, albeit most mammalian cell types appear to be injectable with HSV-1. AAV also has a very wide host and cell type range. The cellular receptor for AAV is not known, but a 150 kDA glycoprotein has been described whose presence in cultured cells correlates with their ability to bind AAV (Mizukami, H. et al., *Virology* 217:124-130 (1996)).

Techniques for the formation of such vectors are well-known in the art; and are generally described in "Working Toward Human Gene Therapy," Chapter 28 in *Recombinant DNA, 2nd Ed.*, Watson, J. D. et al., eds., New York: Scientific American Books, pp. 567-581 (1992). In addition, general methods for construction of gene therapy vectors and the introduction thereof into affected animals for therapeutic purposes may be found in the above-referenced publications, the disclosures of which are specifically incorporated herein by reference in their entirety.

In one general method, vectors comprising polynucleotides encoding PTH derivative gene are directly introduced into the cells or tissues of the affected individual, preferably by injection, inhalation, ingestion or introduction into a mucous membrane via solution; such an approach is generally referred to as "in vivo" gene therapy. Alternatively, cells or tissues, e.g., hematopoietic cells from bone marrow, may be removed from the affected animal and placed into culture according to methods that are well-known to one of ordinary skill in the art; the vectors comprising the polynucleotides may then be introduced into these cells or tissues by any of the methods described generally above for introducing isolated polynucleotides into a cell or tissue, and, after a sufficient amount of time to allow incorporation of the polynucleotides, the cells or tissues may then be re-inserted into the affected animal or a second animal in need of treatment. Since the introduction of the DNA of interest is performed outside of the body of the affected animal, this approach is generally referred to as "ex vivo" gene therapy.

For both in vivo and ex vivo gene therapy, the polynucleotides of the invention may alternatively be operatively linked to a regulatory DNA sequence, which may be a heterologous regulatory DNA sequence, to form a genetic construct as described above. This genetic construct may then be inserted into a vector, which is then directly introduced into the affected animal in an in vivo gene therapy approach, or into the cells or tissues of the affected animal in an ex vivo approach. In another preferred embodiment, the genetic construct may be introduced into the cells or tissues of the animal, either in vivo or ex vivo, in a molecular conjugate with a virus (e.g., an adenovirus) or viral components (e.g., viral capsid proteins).

The above approaches result in (a) homologous recombination between the nucleic acid molecule and the defective gene in the cells of the affected animal; (b) random insertion of the gene into the host cell genome; or (c) incorporation of the gene into the nucleus of the cells where it may exist as an extrachromosomal genetic element. General descriptions of such methods and approaches to gene therapy may be found, for example, in U.S. Pat. No. 5,578,461; WO 94/12650; and WO 93/09222.

Alternatively, transfected host cells, which may be homologous or heterologous, may be encapsulated within a semi-permeable barrier device and implanted into the affected animal, allowing passage of for example the PTH polypeptide derivative into the tissues and circulation of the animal but preventing contact between the animal's immune system and the transfected cells (see WO 93/09222).

Utility and Administration of Compounds of the Invention

Compounds of the invention or derivatives thereof have multiple uses. These include, inter alia, agonists or antagonists of the PTH receptor, prevention and treatment of a variety of mammalian conditions manifested by loss of bone mass, diagnostic probes, antigens to prepare antibodies for use as diagnostic probes and even as molecular weight markers. Being able to specifically substitute one or more amino acids in the PTH polypeptide permits construction of specific molecular weight polypeptides as required.

In particular, the compounds of this invention are indicated for the prophylaxis and therapeutic treatment of osteoporosis and osteopenia in humans. Furthermore, the compounds of this invention are indicated for the prophylaxis and therapeutic treatment of other bone diseases. The compounds of this invention are also indicated for the prophylaxis and therapeutic treatment of hypoparathyroidism. Finally, the compounds of this invention are indicated for use as agonists for fracture repair and as antagonists for hypercalcemia.

In general, compounds of for example, SEQ ID NO: 1 or derivatives thereof, or salts thereof, are administered in amounts between about 0.01 and 1 µg/kg body weight per day, preferably from about 0.07 to about 0.2 µg/kg body weight per day. For a 50 kg human female subject, the daily dose of biologically active compound is from about 0.5 to about 50 µgs, preferably from about 3.5 to about 10 µgs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. For example, this dosage may be delivered in a conventional pharmaceutical composition by nasal insufflation.

The selection of the exact dose and composition and the most appropriate delivery regimen will be influenced by, inter alia, the pharmacological properties of the selected compounds of the invention, the nature and severity of the condition being treated, and the physical condition and mental acuity of the recipient.

Representative preferred delivery regimens include, without limitation, oral, parenteral, subcutaneous, transcutaneous, intramuscular and intravenous, rectal, buccal (including sublingual), transdermal, and intranasal insufflation.

Pharmaceutically acceptable salts retain the desired biological activity of the compounds of the invention without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like. Pharmaceutically acceptable buffers include but are not limited to saline or phosphate buffered saline. Also included in these solutions may be acceptable preservative known to those of skill in the art.

A further aspect of the present invention relates to pharmaceutical compositions comprising as an active ingredient compounds of the invention or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for the most preferred route of administration, nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189, incorporated by reference herein. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987, incorporated by reference herein.

Like PTH, the PTH variants may be administered in combination with other agents useful in treating a given clinical condition. When treating osteoporosis and other bone-related disorders for example, the PTH variants may be administered in conjunction with a dietary calcium supplement or with a vitamin D analog (see U.S. Pat. No. 4,698,328). Alternatively, the PTH variant may be administered, preferably using a cyclic therapeutic regimen, in combination with bisphosphonates, as described for example in U.S. Pat. No. 4,761,406, or in combination with one or more bone therapeutic agents such as, without limitation, calcitonin and estrogen.

Receptor-Signaling Activities of Compounds of the Invention or Derivatives Thereof A crucial step in the expression of hormonal action is the interaction of hormones with receptors on the plasma membrane surface of target cells. The formation of hormone-receptor complexes allows the transduction of extracellular signals into the cell to elicit a variety of biological responses.

Polypeptides of the invention may be screened for their agonistic or antagonistic properties using the cAMP accumulation assay. Cells expressing PTH-1 receptor on the cell surface are incubated with native PTH(1-84) for 5 60 minutes at 37° C., in the presence of 2 mM IBMX (3-isobutyl-1-methyl-xanthine, Sigma, St. Louis, Mo.). Cyclic AMP accumulation is measured by specific radio-immunoassay. A compound of the invention that competes with native PTH(1-84) or PTH(1-34) for binding to the PTH-1 receptor, and that inhibits the effect of native PTH(1-84) or PTH(1-34) on cAMP accumulation, is considered a competitive antagonist. Such a compound would be useful for treating hypercalcemia.

Conversely, a compound of the invention or a derivative thereof that does not compete with native PTH(1-84) or PTH (1-34) for binding to the PTH-1 receptor, but which still prevents native PTH(1-84) or PTH(1-34) activation of cAMP accumulation (presumably by blocking the receptor activation site) is considered a non-competitive antagonist. Such a compound would be useful for treating hypercalcemia.

A compound of the invention or a derivative thereof that competes with native PTH(1-84) or PTH(1-34)) for binding to the PTH-1 receptor, and which stimulates cAMP accumulation in the presence or absence of native PTH(1-84) or PTH(1-34) is a competitive agonist. A compound of the invention or a derivative thereof that does not compete with native PTH(1-84) or PTH(1-34) for binding to the PTH-1 receptor but which is still capable of stimulating cAMP accumulation in the presence or absence of native PTH(1-84) or PTH(1-34), or which stimulates a higher cAMP accumulation than that observed by a compound of the invention or a derivative thereof alone, would be considered a non-competitive agonist.

Likewise, polypeptides of the invention may be screened for their agonistic or antagonistic properties using the inositol phosphate accumulation assay. Cells expressing PTH-1 receptor on the cell surface are incubated with native PTH(1-84), and inositol phosphate accumulation is measured by specific radio-immunoassay. A compound of the invention that competes with native PTH(1-84) or PTH(1-34) for binding to the PTH-1 receptor, and that inhibits the effect of native PTH(1-84) or PTH(1-34) on inositol phosphate accumulation, is considered a competitive antagonist. Such a compound would be useful for treating hypercalcemia.

Conversely, a compound of the invention or a derivative thereof that does not compete with native PTH(1-84) or PTH (1-34) for binding to the PTH-1 receptor, but which still prevents native PTH(1-84) or PTH(1-34) activation of inositol phosphate accumulation (presumably by blocking the receptor activation site) is considered a non-competitive antagonist. Such a compound would be useful for treating hypercalcemia.

A compound of the invention or a derivative thereof that competes with native PTH(1-84) or PTH(1-34)) for binding to the PTH-1 receptor, and which stimulates inositol phosphate accumulation in the presence or absence of native PTH (1-84) or PTH(1-34) is a competitive agonist. A compound of the invention or a derivative thereof that does not compete with native PTH(1-84) or PTH(1-34) for binding to the PTH-1 receptor but which is still capable of stimulating inositol phosphate accumulation in the presence or absence of native PTH(1-84) or PTH(1-34), or which stimulates a higher inositol phosphate accumulation than that observed by a compound of the invention or a derivative thereof alone, would be considered a non-competitive agonist.

Therapeutic Uses of Compounds of the Invention or Derivatives Thereof

Some forms of hypercalcemia and hypocalcemia are related to the interaction between PTH and PTHrP and the PTH-1 and PTH-2 receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypernephroma. Hypocalcemia, a condition in which the serum calcium level is abnormally low, may result from a deficiency of effective PTH, e.g., following thyroid surgery.

Nucleic acids of the invention which encode compounds of the invention or derivatives thereof may also be linked to a selected tissue-specific promoter and/or enhancer and the resultant hybrid gene introduced, by standard methods (e.g., as described by Leder et al., U.S. Pat. No. 4,736,866, herein incorporated by reference), into an animal embryo at an early developmental stage (e.g., the fertilized oocyte stage), to produce a transgenic animal which expresses elevated levels of compounds of the invention or derivatives thereof in selected tissues (e.g., the osteocalcin promoter for bone). Such promoters are used to direct tissue-specific expression of compounds of the invention or derivatives thereof in the transgenic animal.

In addition, any other amino-acid substitutions of a nature, which do not destroy the ability of the PTH derivative to antagonize or agonize the PTH-1/PTH-2 receptor (as determined by assays known to the skilled artisan and discussed below) are included in the scope of the present invention.

By "agonist" is intended a ligand capable of enhancing or potentiating a cellular response mediated by the PTH-1 receptor. By "antagonist" is intended a ligand capable of inhibiting a cellular response mediated by the PTH-1 receptor. Whether any candidate "agonist" or "antagonist" of the present invention can enhance or inhibit such a cellular response can be determined using art-known protein ligand/receptor cellular response or binding assays, including those described elsewhere in this application.

In accordance with yet a further aspect of the invention, there is provided a method for treating a medical disorder that results from altered or excessive action of the PTH-1 receptor, comprising administering to a patient therapeutically effective amount of a compound of the invention or a derivative thereof sufficient to inhibit activation of the PTH-1 receptor of said patient.

In this embodiment, a patient who is suspected of having a disorder resulting from altered action of the PTH-1 receptor may be treated using compounds of the invention or derivatives thereof of the invention which are a selective antagonists of the PTH-1 receptor. Such antagonists include compounds of the invention or derivatives thereof of the invention which have been determined (by the assays described herein) to interfere with PTH-1 receptor-mediated cell activation or other derivatives having similar properties.

To administer the antagonist, the appropriate compound of the invention or a derivative thereof is used in the manufacture of a medicament, generally by being formulated in an appropriate carrier or excipient such as, e.g., physiological saline, and preferably administered intravenously, intramuscularly, subcutaneously, orally, or intranasally, at a dosage that provides adequate inhibition of a compound of the invention or a derivative thereof binding to the PTH-1 receptor. Typical dosage would be 1 ng to 10 mg of the peptide per kg body weight per day.

In accordance with yet a further aspect of the invention, there is provided a method for treating osteoporosis, comprising administering to a patient a therapeutically effective amount of a compound of the invention or a derivative thereof, sufficient to activate the PTH-1 receptor of said patient. Similar dosages and administration as described above for the PTH/PTHrP antagonist, may be used for administration of a PTH/PTHrP agonist, e.g., for treatment of conditions such as osteoporosis, other metabolic bone disorders, and hypoparathyroidism and related disorders.

It will be appreciated to those skilled in the art that the invention can be performed within a wide range of equivalent parameters of composition, concentration, modes of administration, and conditions without departing from the spirit or scope of the invention or any embodiment thereof.

Interactions of Parathyroid Hormone and Parathyroid Hormone Receptors

Understanding the mechanisms by which peptide hormones and G protein-coupled receptors interact is of fundamental biological importance. Parathyroid hormone (PTH), a key regulator of calcium, phosphate and bone metabolism, interacts with a class-2 GPCR, the PTH receptor or PTHR, which is expressed in bone and kidney cells. Each of the 15 or so class-2 GPCRs binds a peptide hormone with a pharmacophoric region that spans about 30 amino acids in peptide chain length. These peptides are generally thought to interact with their receptor via a multi-step mechanism that involves ligand contacts to both the receptor's amino-terminal extracellular (N) domain, and to its juxtamembrane (J) region that contains the extracellular loops and seven transmembrane domain helices. For the PTHR, which also binds the developmental protein, PTH-related protein, understanding the molecular mechanisms that underlie the ligand-interaction process has direct implications for human health, as PTH agonist ligands, such as PTH(1-34) and PTH(1-31) can potently stimulate bone formation and are thus effective therapies for treating osteoporosis (Neer, R., Arnaud, et al. (2001) *N.E.1M* 344, 1434-1441; Whitfield, J. F., et al. (1997) *Calcif Tissue Int* 60, 26-29).

An extensive body of data derived largely from mutational and photoaffinity cross-linking studies suggest that the mechanism by which PTH(1-34), or as used in this study, PTH(1-31), interacts with the PTHR involves two principal, and to some extent, autonomous, components (reviewed in Gensure, R. C., et al. (2005) *Biochem Biophys Res Commun* 328, 666-78). The first component is an interaction between the ligand's principal receptor-binding domain, contained within the carboxyl-terminal portion of the molecule (Rosenblatt, M., et al. (1980) *Endocrinology* 107, 545-550), and the receptor's amino-terminal extracellular domain, a presumed disulfide-stabilized globular structure (Grace, C. R., et al. (2004) *Proc Natl Acad Sci USA* 101:12836-41). The second is an interaction between the principal signaling domain of the ligand, contained within the amino-terminal portion of the molecule, and the receptor's juxtamembrane region of the heptahelical core. By this model, the initial docking of the ligand to the PTHR N domain anchors the ligand to the receptor and thus enables the amino-terminal portion of the ligand to engage the receptor's J domain and induce the conformational changes involved in receptor activation (Hoare, S., *J. Biol. Chem* 276, 7741-7753).

Solution phase NMR studies generally show that the carboxyl-terminal binding domain portion of a PTH ligand forms a stable α-helix, whereas the amino-terminal portion of the ligand is largely disordered (Chen, Z., et al. (2000) *Biochemistry* 39, 12766-12777; Pellegrini, M., et al. (1998) *J. Biol. Chem.* 273, 10420-10427). Functional studies with modified amino-terminal PTH fragment analogs suggest that binding of the N-terminal domain of the ligand to the receptor's J domain is coupled to a folding of that ligand domain into an α-helix. Thus, the cAMP-stimulating potency of the native PTH(1-14) fragment is greatly improved by substitutions, such as Aib at positions 1 and 3, that rigidify the peptide into an α-helix (Shimizu, M., et al. (2001) *Endocrinology* 142, 3068-3074; Tsomaia, N., et al. (2004) *Biochemistry* 43:690-9). Moreover, amino-terminal fragments such as [Aib$^{1,3}$,Gln$^{10}$,Har$^{11}$,Ala$^{12}$,Trp$^{14}$]PTH(1-14)NH$_2$ stimulate full and potent cAMP responses in cells expressing a mutant PTHR construct, PTHR-delNt, that lacks the receptor's N-domain, and on which unmodified PTH(1-34) is only weakly active (Shimizu, N., et al. (2001) *J Biol Chem* 276, 49003-49012; Shimizu, M., et al. (2002) *Biochemistry* 41:13224-13233.), due to the absence of N domain interactions. These findings with modified PTH(1-14) analogs and PTHR-delNt also serve to illustrate the autonomous potential of the J domain component of the PTH-PTHR interaction mechanism.

For the native hormone acting on the intact PTHR, the ligand's carboxyl-terminal binding domain, contained within the (Ser$^{17}$-Val$^{31}$) region, clearly plays a key role in the interaction process. Within this domain, functional studies have identified Arg$^{20}$, Trp$^{23}$, Leu$^{24}$ and Leu$^{28}$ as important PTHR-binding determinants (Gardella, T. J., et al. (1993) *Endocrinology* 132:2024-2030; Oldenburg, K. R., et al. (1996) *Journal Of Biological Chemistry* 271:17582-17591; Barbier, J., et al. (2001) *Biochemistry* 40:8955-8961; Reidhaar-Olson, J., et al. (2000) *Mol Cell Endocrinol* 160:135-147). The α-helix contained within this (17-31) segment has amphiphilic character (Neugebauer, W., (1992) *Biochemistry* 31:2056-2063; Epand, R. E. (1983) *Mol and Cell Biol* 57, 41-47; Barbier, J. R., et al. (2005) *J Biol Chem.* 280:23771-23777), the hydrophobic face of which, formed largely by Trp$^{23}$, Leu$^{24}$ and Leu$^{28}$, appears to contribute most importantly to the PTHR-binding process, according to the above substitution studies. Although the two-domain model of the PTH-PTHR interaction mechanism predicts that these residues interact specifically with the PTHR N domain, this has not been firmly established. Moreover, the recent finding that [Lys$^{27}$(Bp)$_2$] PTH(1-34)NH$_2$, modified with photo-reactive benzophenone groups on the side chain amines of Lys$^{27}$, cross-links to the first extracellular loop of the PTHR (Greenberg, Z., (2000) *Biochemistry* 39:8142-8152) raises the possibility that some interaction between the carboxyl-terminal helix and the PTHR J domain can occur. Consistent with this possibility, recent functional studies have found that methylation of certain backbone nitrogen atoms in the (17-31) domain of PTH (1-31) impairs, albeit modestly, the cAMP-signaling activity of the ligand in cells expressing PTHR-delNt (Barbier, J. R., et al. (2005) *J Biol Chem.* 280:23771-23777). Thus, the mechanisms by which the carboxyl-terminal binding domain of PTH contributes to the PTHR interaction process are presently not well understood.

For the PTHR, the new PTH analogs presented here can be used to probe receptor mutants altered at candidate sites in the N domain, to identify, via epistatic, rescue effects, sites of functionally relevant intermolecular interaction.

Having now fully described the invention, the same will be more readily understood by reference to specific examples which are provided by way of illustration, and are not intended to be limiting of the invention, unless herein specified.

It should be understood that these conditions are not meant to be definitive or limiting and may be adjusted as required by those of ordinary skill in the art to accomplish the desired objective.

EXAMPLES

Introduction to Examples

Studies were designed to further examine the mechanisms of interaction between the parathyroid hormones and hormone receptors. The roles that the amino acid side chains in this domain play in the receptor-binding process, the functional involvement of the putative amphiphilic α-helix, and the potential for interactions to the PTHR J domain were studied. The strategy was to introduce a number of substitutions, conservative and non-conservative, in the (17-31) region of PTH(1-31) analogs and assess their effects on binding to both the intact PTHR and to PTHR-delNt. The analysis of binding to the latter receptor was made possible by using $^{125}$I-[Aib$^{1,3}$,Nle$^{8}$,Gln$^{10}$,Har$^{11}$,Trp$^{14}$,Tyr$^{15}$]PTH(1-15) as a tracer radioligand and expressing the truncated mutant PTHR in cells co-transfected with a negative-dominant Gαs subunit that couples more efficiently to the receptor, and thus improves the overall binding signal (Dean, T., (2006) *Mol Endocrinol* 20:931-942). This general approach enabled, for the first time, the study of effects of modifications in the carboxyl-terminal binding domain of relatively unmodified PTH ligands on interaction with the PTHR J domain, as defined by the PTHR-delNt construct. The overall results help define the roles that specific amino acid side-chains in the carboxyl-terminal domain of PTH play in the PTHR-binding process, and shed new light on the overall topology of the PTH-PTHR complex.

Materials and Methods

Peptide synthesis—Peptides were based on the human PTH(1-31)NH$_2$ sequence (SVSEIQLMHNLGKHLNS-MERVEWLRKKLQDV-NH$_2$ (SEQ ID NO:13)). Alanine substitutions were incorporated into this PTH(1-31)NH$_2$ scaffold. To augment binding to PTHR-delNt, the Ser$^1$→Ala (Shimizu, M., et al. (2000) *J. Biol. Chem.* 275:21836-21843) and Glu$^{19}$→Arg (Shimizu, M., et al (2002) *Biochemistry* 41:13224-13233) substitutions were introduced to yield [Ala$^1$,Arg$^{19}$]PTH(1-31)NH$_2$. This scaffold peptide was used for studies involving the Cha and Glu substitutions. These PTH(1-31)NH$_2$, and [Ala$^1$,Arg$^{19}$]PTH(1-31)NH$_2$ peptides, and their Ala-, Glu- and Cha-substituted derivatives were synthesized by the M.G.H. Biopolymer core facility using a multiple peptide synthesizer (Advanced Chemtech Model 396 MBS) and solid-phase, Fmoc-based, coupling/deprotection chemistry. Peptides were desalted using a C18 Sep-Pak cartridge and acetonitrile-based elution. The Ala-substituted PTH(1-31) analogs, shown by HPLC analysis to be at least 90% homogeneous at this stage, were used without further purification. The Cha- and Glu-substituted peptides were further purified by reversed-phase HPLC. Analogs of PTH(1-31)NH$_2$ with additional substitutions at position 20 were prepared as part of the previous studies by Barbier et al. ((2001) *Biochemistry* 40:8955-8961). Lyophilized peptides were reconstituted as stock solutions in 10 mM acetic acid. All peptides were verified by analytical HPLC, matrix-assisted laser desorption/ionization (MALDI) mass spectrometry and amino acid analysis. Peptide concentrations were established by amino acid analysis. The radioligands $^{125}$I-[Nle$^{8,21}$,Tyr$^{34}$]ratPTH(1-34)NH$_2$ and $^{125}$I-[Aib$^{1,3}$,Nle$^8$,Gln$^{10}$,Har$^{11}$,Ala$^{12}$,Trp$^{14}$,Tyr$^{15}$]ratPTH(1-15)NH$_2$($^{125}$I-PTH(1-34)NH$_2$ and 125I-[Aib$^{1,3}$,M]PTH(1-15)NH$_2$, respectively) were prepared by the oxidative chloramine-T procedure using Na$^{125}$I (specific activity: 2,200 Ci/mmol, Perkin Elmer/NEN Life Science Products, Boston, Mass.) and were purified by reversed-phase HPLC.

Circular Dichroism—CD spectra were obtained on a JASCO J-600 spectropolarimeter at 20° C. Four spectra were averaged and the data smoothed by the JASCO software. The instrument was calibrated with ammonium (+)-10-camphorsulfonate. Peptide concentrations were verified from the absorption at 280 nm, using an extinction coefficient of 5700 M$^{-1}$ for the single tryptophan. Data are expressed as the number of helical residues per peptide chain, as calculated from $-[\theta]_{222} \times 30/28,000$, where $[\theta]_{222}$ is the mean residue elipticity ($[\theta]$) at 222 nm, as was described previously (Barbier, J. R., et al. (2005) *J Biol Chem.* 280:23771-23777).

Cell Culture—Cells were cultured at 37° C. in a humidified atmosphere containing 5% CO$_2$ in Dulbecco's modified Eagle's medium (DMEM), supplemented with 10% fetal bovine serum (HyClone, Logan Utah), 100 units/ml penicillin G, and 100 ug/ml streptomycin penicillin G/streptomycin (Invitrogen Corp. Carlsbad, Calif.). For binding and cAMP studies performed with the intact PTHR, the HKRK-B7 and ROS 17/2.8 cell lines were used. HKRK-B7 cells are derived from the porcine kidney cell line LLC-PK1 and express, via stable DNA transfection, the wild-type human PTHR at an approximate surface density of 950,000 PTH-binding sites per cell. ROS 17/2.8 cells are rat osteosarcoma cells and express the endogenous PTHR at an approximate surface density of 80,000 PTH-binding sites per cell. The cells were plated and assayed in 24-well plates.

PTHR-delNt is a derivative of the human PTHR that is deleted for most (Ala$^{24}$-Arg$^{181}$) of the amino-terminal extracellular domain (Shimizu, M., et al. (2001) *Endocrinology* 142:3068-3074). This PTHR construct was expressed in COS-7 cells via transient DNA transfection. For cAMP assays, the cells were transfected in 24-well plates using 0.2 µg of plasmid DNA and 0.6 µl of Fugene-6 reagent (Roche Diagnostics, Indianapolis Ind.) per well, and assays were performed on the intact cells three to four days after transfection. For binding assays, cell membranes were prepared from transfected COS-7 cells. To increase the maximal binding of $^{125}$I-[Aib$^{1,3}$,M]PTH(1-15)NH$_2$ to PTHR-delNt in these membranes, the cells were cotransfected with a negative dominant mutant Gα$_s$ protein (Gα$_s^{ND}$). This mutant Gα$_s$ subunit is thought to couple to cognate receptors, and thus stabilize high affinity receptor conformations, more efficiently than does wild-type Gα$_s$, without increasing basal cAMP levels (Berlot, C. H. (2002) *J Biol Chem* 277:21080-5). A precursor of this mutant Gα$_s$, Gα$_s$(α3β5), was recently used to increase binding of $^{125}$I-[Aib$^{1,3}$,M]PTH(1-15)NH$_2$ to PTHR-delNt in COS-7 cell membranes (Dean, T., (2006) *Mol Endocrinol* 20:931-942). Gα$_s^{ND}$, which contains the same five amino acid replacement of corresponding Gα$_i$ residues in the α3β5 loop as Gα$_s$(α3β5), plus the point mutations of Gly$^{226}$ to Ala, which increases affinity for Gβ/γ, and Ala$^{366}$ to Ser, which decreases affinity for GDP, yields approximately two-fold higher levels of specific binding of $^{125}$I-[Aib$^{1,3}$,M]PTH(1-15)NH$_2$ than does Gα$_s$(α3β5) (data not shown). For the current membrane preparations, COS-7 cells were co-transfected in six-well plates using 1 µg of each plasmid DNA encoding PTHR-delNt and Gαs$^{ND}$, and 6 µl of Fugene-6 reagent (Roche Diagnostics, Indianapolis Ind.) per well. Cells were harvested three days after transfection, and membranes were prepared as described (Dean, T., et al. (2006) *Mol Endocrinol* 20:931-942).

Receptor binding—Binding to the wild-type human PTHR in intact HKRK-B7 cells and ROS 17/2.8 cells was assessed using $^{125}$I-PTH(1-34) as a tracer radioligand, as described (Shimizu, M., (2001) *Endocrinology* 142:3068-3074). In brief, the cells in 24-well plates (about 500,000 cells per well) were incubated in binding buffer containing radioligand (about 100,000 cpm per well) with or without unlabeled peptide ligand (3×10$^{-9}$ to 1×10$^{-5}$ M) for four hours at 15° C. The binding mixture was then removed by aspiration, the cells were rinsed three times with binding buffer, lysed in 1 M NaOH, and the entire lysate was counted for gamma-irradiation in a gamma counter. Binding to PTHR-delNt in COS-7 cell membranes was assessed in 96-well, vacuum filtration plates (Multiscreen-Durapore HV, 0.65 µM membranes, Millipore Corp., Millford, Mass.) using $^{125}$I-[Aib$^{1,3}$,M]PTH(1-15)NH$_2$ as a tracer radioligand, as described (Dean, T., (2006) *Mol Endocrinol* 20:931-942). In brief, cell membranes (20 µg/well) were incubated in membrane binding buffer containing radioligand (30,000 cpm/well) with or without unlabeled peptide ligand (3×10$^{-9}$ to 1×10$^{-5}$ M) for 90 minutes at 21° C. The plates were then subject to rapid vacuum filtration, the filters were washed once with buffer, detached from the plate and counted for gamma-irradiation in a gamma counter. Non-specific binding was defined as the binding observed in the presence of $1\times10^{-6}$ M PTH(1-31)$NH_2$ for HKRK-B7 and ROS 17/2.8 cells, and $1\times10^{-6}$ M [Aib$^{1,3}$,M]PTH(1-15)$NH_2$ for PTHR-delNt. Specifically bound radioactivity was calculated as a percentage of the radioactivity specifically bound in the absence of competing ligand.

Stimulation of intracellular cAMP and inositol phosphate—The capacities of the ligands to stimulate adenylyl cyclase activity were assessed in intact ROS 17/2.8 cells, as described (Shimizu, M., (2001) *Endocrinology* 142:3068-3074). In brief, cells in 24-well plates were incubated in binding buffer containing the phosphodiesterase inhibitor, IBMX, with or without a peptide ligand ($3\times10^{-9}$ to $1\times10^{-5}$ M) for 30 minutes at room temperature. The medium was removed and the cells were lysed by adding 50 mM HCl and freezing the plate on dry ice. The cAMP in the thawed lysate was then quantified by radioimmuno assay. The stimulation of production of inositol phosphates ($IP_1+IP_2+IP_3$) was assessed in COS-7 cells transfected with the intact human PTHR, as described previously (Shimizu, M., (2001) *Endocrinology* 142:3068-3074). In brief, intact transfected COS-7 cells in 24-well plates were labeled with $^3$H-myo-inositol (specific activity: 25 Ci/mmol, Perkin Elmer/NEN Life Science Products, Boston, Mass.) for 16 hours, treated for 30 minutes with ligand in the presence of $LiCl_2$ (30 mM), treated with ice cold trichloroacetic acid (5%) for two hours; the acid lysates were then ether extracted, separated by ion-exchange chromatography, and eluted $^3$H-inositol phosphates were quantified by liquid scintillation counting.

Data and statistical calculations—Data were processed for curve fitting and derivation of $IC_{50}$ and $EC_{50}$ values using least-squares, nonlinear regression analysis and the four parameter logistic equation: $y=y_{min}+(V_{max}-y_{min})/1+(IC_{50}/x)^n$, where y, $y_{min}$ and $y_{max}$ are the observed, minimum and maximum response values, respectively; x is ligand concentration, and n is the slope factor. In cases where incomplete inhibition of binding occurred: i.e. with certain PTH(1-31) analogs binding to PTHR-delNt, the curve fits and $IC_{50}$ values were derived by extrapolating the data to the maximum inhibition attained by [Aib$^{1,3}$,M]PTH(1-15)$NH_2$. Paired data sets were statistically compared using a two-tailed Student's t-test, assuming unequal variances for the two sets.

Example 1

Alanine-Scan of the PTH(17-31) domain—Each residue in the (17-31) region of PTH(1-31)$NH_2$ was individually replaced with alanine and the effects of the substitutions on binding to the intact human PTHR stably expressed in HKRK-B7 cells was assessed. Competition binding studies were performed using whole cells and $^{125}$I-PTH(1-34) ($^{125}$I-[Nle$^{8,21}$,Tyr$^{34}$]ratPTH(1-34)$NH_2$) as a tracer radioligand. The unsubstituted parental PTH(1-31)$NH_2$ peptide fully inhibited the binding of this tracer with an $IC_{50}$ of 68±10 nM (FIG. 1A; Table 1). The various alanine substitutions had a range of effects on this apparent PTHR-binding affinity. Most dramatically, the Arg$^{20}$ to Ala substitution, abolished detectable binding altogether (FIG. 1A). The alanine substitutions at Trp$^{23}$ and Leu$^{24}$ reduced binding affinity by 19- and 12-fold, respectively (P≦0.05), and those at Val$^{21}$, Arg$^{25}$, Lys$^{27}$, Leu$^{28}$ and Val$^{31}$ reduced affinity by three- to four-fold (FIGS. 1A and B; Table 1). The remaining alanine substitutions altered binding affinity by two-fold or less. The alanine substitutions at Glu$^{19}$, Glu$^{22}$ and Gln$^{29}$ each produced a small (≦two-fold, enhancement in apparent PTHR-binding affinity, as did the Glu$^{19}$ to Arg substitution, consistent with the potency-enhancing effects seen previously for this substitution in PTH(1-34) and PTH(1-20) peptides, when assessed in cAMP stimulation assays (Shimizu, M., et al. (2002) *Biochemistry* 41:13224-13233). Combining the Ala$^{22}$ substitution with either the Ala$^{19}$ or Arg$^{19}$ substitution did not lead to further improvements in PTHR-binding affinity (Table 1).

It was then assessed whether any of the alanine substitutions affected binding interactions to the receptor's J domain using PTHR-delNt. For these experiments, membranes prepared from COS-7 cells transiently transfected with PTHR-delNt were used, and, as a tracer radioligand, $^{125}$I-[Aib$^{1,3}$,M]PTH(1-15) ($^{125}$I-[Aib$^{1,3}$,Nle$^8$,Gln$^{10}$,homoarginine$^{11}$,Ala$^{12}$,Trp$^{14}$,Tyr$^{15}$]PTH(1-15)$NH_2$), which binds exclusively to the J domain (Shimizu, N., et al. (2005) *J Biol Chem* 280:1797-807). To increase the total specific binding of $^{125}$I-[Aib$^{1,3}$,M]PTH(1-15) to these membranes, the cells were co-transfected with a negative-dominant $G\alpha_s$ mutant subunit, $G\alpha_s(\alpha_3\beta_5$, Gly$^{226}$Ala,Ala$^{366}$Ser); this $G\alpha_s^{ND}$ mutant is thought to couple to cognate receptors, and thus stabilize their high-affinity conformations, more efficiently than does wild-type $G\alpha_s$ (Berlot, C. H. (2002) *J Biol Chem* 277:21080-5). The apparent affinity observed for a PTH analog in these assays performed with PTHR-delNt and $^{125}$I-[Aib$^{1,3}$,M]PTH(1-15)$NH_2$ thus reflects the overall strength of the interactions that occur between that ligand and the PTHR J domain.

The unlabeled [Aib$^{1,3}$,M]PTH(1-15)$NH_2$ control peptide bound to these membranes with high apparent affinity, whereas unmodified PTH(1-31)$NH_2$ bound with much weaker affinity ($IC_{50}$s=2.2±0.5 nM and 3,700±400 nM, respectively, P=0.001; FIGS. 1C and D; Table 1). The weak binding that PTH(1-31)$NH_2$ exhibits on PTHR-delNt highlights the importance of the PTHR N domain in determining the overall affinity with which this non-optimized ligand binds to the wild-type PTHR. None of the alanine substitutions in the PTH(1-31)$NH_2$ scaffold strongly affected binding to PTHR-delNt. Most strikingly, the Arg$^{20}$ to Ala substitution, which abolished binding to the PTHR, caused only an approximate five-fold reduction in affinity for PTHR-delNt (FIG. 1A vs. C). Similarly, the Ala substitutions at Trp$^{23}$ and Leu$^{24}$, which reduced affinity for the PTHR by 19- and 12-fold, respectively, reduced affinity for PTHR-delNt by only two-fold. These findings thus suggest that the mechanisms by which the Ala substitutions at Arg$^{20}$, Trp$^{23}$ and Leu$^{24}$ impair binding to the intact PTHR are largely independent of ligand interactions to the PTHR J domain.

None of the substitutions had a major impact on the secondary structure of the peptide, as revealed by circular dichroism (CD) spectroscopy analysis. Thus, the CD spectrum of each analog exhibited clear negative deflections in the region of 209 nm and 222 nm, which are characteristic of a-helical structure (FIG. 2). For PTH(1-31), these negative deflections have been shown by peptide fragment analysis to be derived largely from α-helix in the (17-31) region (Neugebauer, W., et al. (1992) *Biochemistry* 31:2056-2063; Barbier, J. R., et al. (2005) *J Biol Chem.* 280:23771-23777). The number of helical resides per peptide chain, calculated from the CD signal at 222 nm, was between 7 and 10 for each of the peptides studied. (Table 1). The lack of an effect of the substitutions on peptide secondary structure seen in these studies is consistent with the known helix-forming propensity of alanine (Chakrabartty, A., Nature 351:586-8).

helical deflections at 209 and 222 nm were enhanced for the Cha[20] and Cha[27] analogs, resulting in helical content values of 16 and 18 residues, respectively, versus eight residues for

TABLE 1

Helical Contents and PTHR-Binding Properties of PTH(1-31)NH$_2$ Analogs

|  | CD helical residues | PTHR-WT (HKRK-B7 cells) IC$_{50}$ | n | PTHR-delNT (COS-7) IC$_{50}$ | n |
|---|---|---|---|---|---|
| PTH(1-31)NH$_2$ | 8 | 68 ± 10 | 23 | 3,666 ± 431 | 13 |
| Ser[17]→Ala | 10 | 57 ± 12 | 4 | 4,578 ± 386 | 4 |
| Met[18]→Ala | 10 | 92 ± 14 | 3 | 8,799 ± 2,334 | 4 |
| Glu[19]→Ala | 9 | 49 ± 11 | 4 | 2,940 ± 833 | 4 |
| Arg[20]→Ala | 10 | >10,000 | 3 | 19,343 ± 8,100 | 4 |
| Val[21]→Ala | 10 | 200 ± 18 | 3 | 5,686 ± 486 | 4 |
| Glu[22]→Ala | 9 | 36 ± 2 | 4 | 5,857 ± 2,237 | 4 |
| Trp[23]→Ala | 7 | 1,312 ± 139 | 3 | 7,357 ± 1,832 | 4 |
| Leu[24]→Ala | 7 | 807 ± 165 | 3 | 8,764 ± 1,167 | 4 |
| Arg[25]→Ala | 7 | 281 ± 67 | 3 | 7,177 ± 1,083 | 4 |
| Lys[26]→Ala | 7 | 125 ± 8 | 3 | 6,210 ± 948 | 4 |
| Lys[27]→Ala | 9 | 217 ± 7 | 3 | 7,288 ± 615 | 4 |
| Leu[28]→Ala | 8 | 290 ± 63 | 3 | 3,459 ± 482 | 4 |
| Gln[29]→Ala | 9 | 44 ± 11 | 3 | 1,931 ± 303 | 4 |
| Asp[30]→Ala | 10 | 63 ± 7 | 4 | 1,545 ± 215 | 4 |
| Val[31]→Ala | 9 | 176 ± 23 | 4 | 4,911 ± 1,341 | 4 |
| Glu[19,22]→Ala,Ala | 9 | 49 ± 9 | 4 | 619 ± 75 | 4 |
| Glu[19,22]→Arg,Ala | 8 | 54 ± 13 | 4 | 360 ± 19 | 4 |
| Glu[19]→Arg | 8 | 42 ± 6 | 4 | 1,226 ± 332 | 4 |
| Arg[20]→Gln | 7 | >10,000 | 3 | 10,284 ± 121 | 3 |
| Arg[20]→Glu | 7 | >10,000 | 3 | 14,747 ± 324 | 3 |
| Arg[20]→Lys | 8 | >10,000 | 3 | 7,105 ± 1,275 | 3 |
| Arg[20]→Nle | 12 | 15,404 ± 2,334 | 4 | 10,688 ± 1,033 | 3 |
| Arg[20]→Cit | 9 | 11,925 ± 2,151 | 4 | 10,624 ± 1,612 | 3 |
| Arg[20]→Orn | 6 | >10,000 | 4 | 5,530 ± 279 | 3 |
| Arg[20]→Apa | N.D. | >10,000 | 3 | 5,740 ± 775 | 3 |
| Arg[20]→Gph | N.D. | >10,000 | 3 | 2,047 ± 442 | 3 |
| Arg[20]→PipGly | 8 | 14,135 ± 5,345 | 4 | 6,605 ± 2,407 | 5 |
| [Aib[1,3],M]PTH(1-15) | N.D. | N.D. |  | 2.2 ± 0.5 | 8 |

Substitutions were introduced into hPTH(1-31)NH$_2$. The helical residue values were calculated from [θ]$_{222}$, the mean-residue elipticities observed in the CD spectra at 222 nm. Competition binding studies were performed in intact HKRK-B7 cells stably transfected with the hPTHR using $^{125}$I-[Nle[8,21],Tyr[34]]ratPTH(1-34)NH$_2$ tracer radioligand, and in membranes prepared from COS-7 cells transiently transfected with PTHR-delNt and a negative-dominant G$_α$s, using $^{125}$I-[Aib[1,3],Nle[8],Gln[10],Har[11],Ala[12],Trp[14],Tyr[15]]ratPTH(1-15)NH$_2$ tracer radioligand. Binding values (nM) are means (+/−s.e.m.) of data from the number of experiments indicated (n).

Example 2

Substitutions with cyclohexylalanine—The data presented here, and previously (Gardella, T. J., et al. (1993) *Endocrinology* 132:2024-2030; Oldenburg, K. R., et al. (1996) *Journal Of Biological Chemistry* 271:17582-17591; Reidhaar-Olson, J., et al. (2000) *Mol Cell Endocrinol* 160:135-147.) suggest that hydrophobicity in the PTH(17-31) region, as provided principally by the side chains of Trp[23], Leu[24] and Leu[28], is a physicochemical property of the domain that is key for high affinity binding to the receptor. To evaluate further the general importance of hydrophobicity per se in this region of the ligand, each residue in the PTH(17-31) region was substituted with cyclohexylalanine (Cha), a non-encoded amino acid analog that would provide bulk side chain hydrophobicity at the targeted site while altering the chemical and topological features of the side chain, and the effects of the substitutions on binding to the PTHR and to PTHR-delNt were assessed. In these studies, [Ala[1],Arg[19]]PTH(1-31)NH$_2$ was used as a scaffold peptide, in order to augment the capacity to assess binding to PTHR-delNt, since the Glu[19] to Arg and Ser[1] to Ala substitutions were known to improve interaction with the truncated receptor (Shimizu, M., et al. (2002) *Biochemistry* 41:13224-13233; Shimizu, M., et al. (2000) *J. Biol. Chem.* 275:21836-21843).

CD analyses indicated that none of the Cha substitutions disrupted the α-helical content of the peptide, although the parent peptide (FIG. 8; Table 2). The basis for these more intense CD deflections with the Cha[20] and Cha[27] analogs, which were not accompanied by parallel changes in functional activity, is not clear at present.

The effects of the Cha substitutions on binding to the intact PTHR in HKRK-B7 cells were generally milder than those of the alanine substitutions. The Cha substitution at Arg[20] reduced apparent binding affinity by 120-fold (P=0.005), and those at Trp[23] and Leu[24] reduced affinity by 14- and 11-fold, respectively (P<0.002; FIGS. 3A and B; Table 2). Although mild, the effects of the Cha substitutions at Trp[23] and Leu[24] suggest that hydrophobicity per se is not the main structural feature of these two side chains that determines their contribution to PTHR binding affinity. The Cha substitutions at the remaining positions altered PTHR-binding affinity by only six-fold or less.

On PTHR-delNt, the Cha substitutions at Arg[25] and Lys[26] reduced binding affinity by approximately five- to seven-fold; the remaining Cha substitutions, including those at Arg[20], Trp[23] and Leu[24], altered affinity for PTHR-delNt by three-fold or less (FIGS. 3C and D; Table 2). These results with Cha substitutions are in close agreement with those obtained with the corresponding Ala substitutions, and suggest that the detrimental effects that the Cha substitutions at positions 20, 23 and 24 have on PTHR-binding affinity are not due to altered interactions with the PTHR J domain.

TABLE 2

Helical Contents and PTHR-Binding Properties of [Ala$^1$,Arg$^{19}$]hPTH(1-31)NH$_2$ Analogs.

| | CD helical residues | PTHR-WT (HKRK-B7 cells) IC$_{50}$ | n | PTHR-delNT (COS-7) IC$_{50}$ | n |
|---|---|---|---|---|---|
| [Ala$^1$,Arg$^{19}$]PTH(1-31)NH$_2$ | 8 | 38 ± 8 | 7 | 397 ± 40 | 4 |
| Ser$^{17}$→Cha | 9 | 112 ± 13 | 3 | 179 ± 41 | 4 |
| Met$^{18}$→Cha | 8 | 87 ± 13 | 3 | 408 ± 32 | 4 |
| Arg$^{19}$→Cha | 10 | 233 ± 57 | 3 | 780 ± 83 | 4 |
| Arg$^{20}$→Cha | 16 | 4,738 ± 333 | 3 | 632 ± 79 | 4 |
| Val$^{21}$→Cha | 9 | 74 ± 15 | 3 | 564 ± 172 | 4 |
| Glu$^{22}$→Cha | 8 | 75 ± 9 | 3 | 126 ± 45 | 4 |
| Trp$^{23}$→Cha | 8 | 546 ± 70 | 3 | 867 ± 402 | 4 |
| Leu$^{24}$→Cha | 9 | 436 ± 10 | 3 | 283 ± 68 | 4 |
| Arg$^{25}$→Cha | 9 | 103 ± 27 | 3 | 2711 ± 1306 | 4 |
| Lys$^{26}$→Cha | 6 | 172 ± 27 | 3 | 1872 ± 281 | 4 |
| Lys$^{27}$→Cha | 18 | 91 ± 17 | 3 | 629 ± 72 | 4 |
| Leu$^{28}$→Cha | 8 | 65 ± 10 | 3 | 226 ± 39 | 4 |
| Gln$^{29}$→Cha | 8 | 61 ± 14 | 3 | 319 ± 57 | 4 |
| Asp$^{30}$→Cha | 8 | 54 ± 7 | 3 | 305 ± 126 | 4 |
| Val$^{31}$→Cha | 9 | 66 ± 20 | 3 | 466 ± 298 | 4 |
| Arg$^{19}$→Glu | 9 | 125 ± 29 | 4 | 18,856 ± 9649 | 5 |
| Arg$^{20}$→Glu | 8 | >10,000 | 3 | 776 ± 380 | 5 |
| Val$^{21}$→Glu | 7 | 447 ± 172 | 4 | 1,615 ± 516 | 5 |
| Trp$^{23}$→Glu | 7 | 6,044 ± 2,636 | 3 | 434 ± 84 | 5 |
| Leu$^{24}$→Glu | 6 | >10,000 | 3 | 1,041 ± 197 | 5 |
| Arg$^{25}$→Glu | 5 | 189 ± 53 | 4 | 1,629 ± 274 | 5 |
| Lys$^{26}$→Glu | 6 | 60 ± 19 | 3 | 832 ± 215 | 5 |
| Lys$^{27}$→Glu | 5 | 156 ± 50 | 3 | 1,266 ± 293 | 5 |
| Leu$^{28}$→Glu | 5 | 10,360 ± 3,983 | 3 | 974 ± 252 | 5 |

Cyclohexylalanine and glutamate substitutions were introduced into [Ala$^1$,Arg$^{19}$]hPTH(1-31)NH$_2$. The helical residue values were calculated from [θ]$_{222}$, the mean-residue elipticities observed in the CD spectra at 222 nm. Competition binding studies were performed in intact HKRK-B7 cells stably transfected with the hPTHR using $^{125}$I-[Nle$^{8,21}$,Tyr$^{34}$]rPTH(1-34)NH$_2$ tracer radioligand, and in membranes prepared from COS-7 cells transiently transfected with hPTHR-delNt and a negative-dominant Gαs using $^{125}$I-[Aib$^{1,3}$,Nle$^8$,Gln$^{10}$,Har$^{11}$,Ala$^{12}$,Trp$^{14}$,Tyr$^{15}$]rPTH(1-15)NH$_2$ tracer radioligand. Binding values (nM) are means (+/−s.e.m.) of data from the number of experiments indicated (n).

Example 3

Non-conservative Glu substitutions—Substitutions were introduced that would more strongly disrupt binding to the intact PTHR, but only marginally impact binding to PTHR-delNt. To do this, glutamic acid was introduced, as non-conservative single substitutions, at each position in the carboxyl-terminal segment of [Ala$^1$,Arg$^{19}$]PTH(1-31)NH$_2$ that was otherwise occupied by a hydrophobic or positively charged amino acid. The analogs were again assessed for binding to the intact PTHR and to PTHR-delNt. Several of the Glu substitutions caused severe losses of binding affinity for the intact PTHR. Thus, Glu substitution at Arg$^{20}$ and Leu$^{24}$ abolished detectable binding and those at Leu$^{28}$, Trp$^{23}$ and Val$^{21}$ reduced apparent affinity by 270-160- and 12-fold, respectively (FIGS. 4A and B; Table 2). Modest, two- to five-fold reductions in PTHR-binding affinity occurred with the Glu substitutions at Arg$^{19}$, Arg$^{25}$, Lys$^{26}$ and Lys$^{27}$. None of the Glu substitutions substantially altered the CD profile of the peptide (Table 2).

Each of the Glu substitutions had only a mild impact on binding to PTHR-delNt. Thus, Glu substitutions at Arg$^{20}$, Trp$^{23}$, Leu$^{24}$ and Leu$^{28}$, which reduced apparent affinity for the PTHR by 150-fold or more, reduced affinity for the truncated PTHR by less than three-fold (FIGS. 4C and D; Table 2). The Glu substitutions at Val$^{21}$ and Arg$^{25}$ each reduced affinity for PTHR-delNt by about four-fold (P<0.01); which were similar to the effects that the same substitutions had on binding to the intact PTHR. The Arg$^{19}$ to Glu substitution reduced affinity on PTHR-delNt by 50-fold (IC$_{50}$=19.00±10.00 nM, versus 400±40 nM). This deleterious effect is fully consistent with the enhancements in cAMP-stimulating potency seen for the reciprocal Glu$^{19}$ to Arg substitution in PTH(1-20) and PTH(1-34) analogs in COS-7 cells expressing PTHR-delNt (Shimizu, M., et al. (2002) Biochemistry 41:13224-13233).

Example 4

Analysis of arginine-20—Arginine-20, one of the most conserved residues in PTH and PTHrP ligands, has been shown by a number of studies to be critical determinant of the PTHR-interaction mechanism (Oldenburg, K. et al. (1996) Journal Of Biological Chemistry 271:17582-17591; Barbier, J.; et al. (2001) Biochemistry 40:8955-8961; Reidhaar-Olson, J., et al. (2000) Mol Cell Endocrinol 160:135-147), but a mechanistic role for this residue has yet to be described. Barbier et al. analyzed the effects of 11 different amino acid analog substitutions at this position in PTH(1-31)NH$_2$ on the cAMP-stimulating potency of the peptide in ROS 17/2.8 cells, and found that none of the substitutions preserved potency. Thus even the close arginine homologs: citrulline, 4-piperidyl-(N-amidino)glycine (PipGly) and 4-piperidyl-(N-amidino)alanine (PipAla), reduced potency 8-, 5- and >21-fold, respectively, and lysine abolished activity altogether (Barbier, J., et al. (2001) Biochemistry 40:8955-8961). To further dissect the functional role of Arg$^{20}$, the same position-20 modified PTH(1-31)NH$_2$ analogs were examined for their capacities to bind to the intact PTHR and to PTHR-delNt.

Figure 5A:
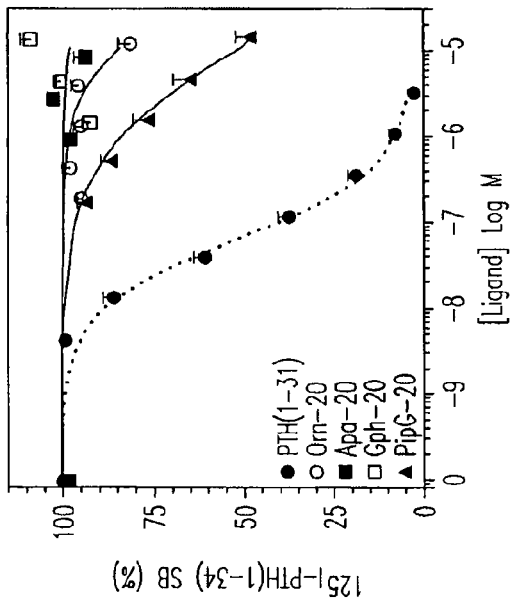
Figure 5C:
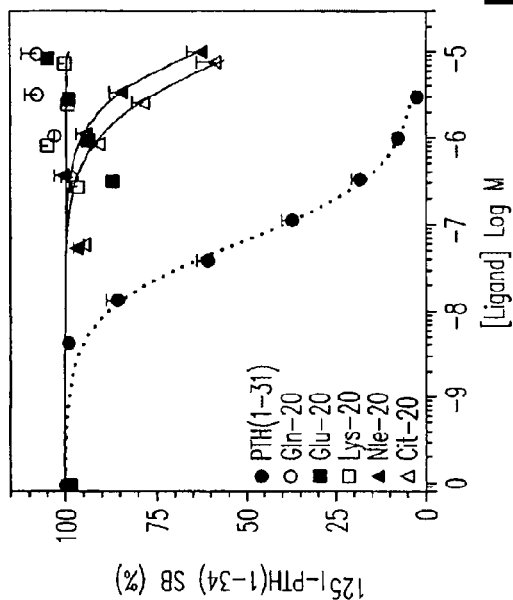
Figure 5B:
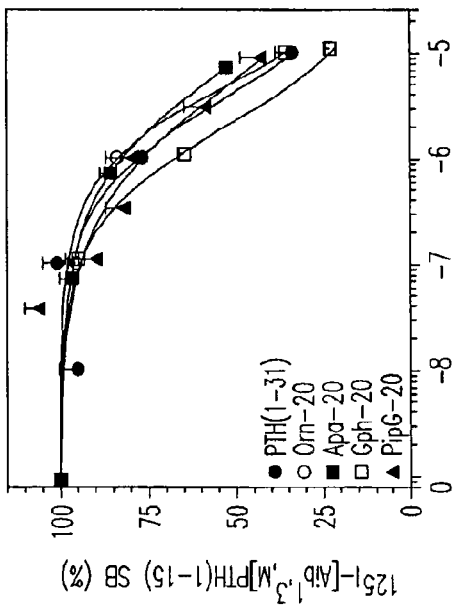
Figure 5D:
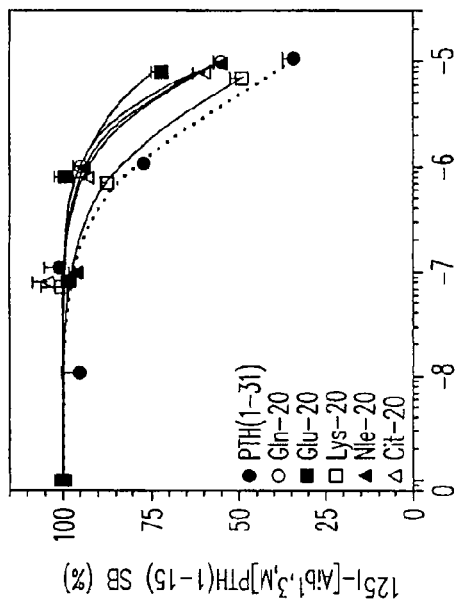

The replacement of Arg$^{20}$ by either Gln, Glu, Lys, (S)-2-amino-4[(2-amino)pyrimidinyl]methylalanine (Apa) or L-4-guanidinoPhenylalanine (Gph), resulted in a complete loss of detectable binding affinity for the intact PTHR (FIGS. 5A and B; Table 1). The substitutions of PipGly, norleucine and citrulline reduced apparent PTHR-binding affinity by about 200-fold, relative to that of the parent peptide. Each of the position 20 substitutions had relatively mild effects on binding to PTHR-delNt, as the $IC_{50}$ of each of analog was within about four-fold of that of the parent PTH(1-31)$NH_2$ peptide (FIGS. 5C and D; Table 1). These effects are consistent with those observed for the Ala-, Cha- and Glu substitutions at position 20, as they indicate that the effects of the substitutions on binding are largely independent of interactions to the PTHR J domain. The $Arg^{20}$ to Glu substitution in PTH(1-31)$NH_2$ resulted in a small, approximately four-fold reduction in apparent binding affinity for PTHR-delNt, suggesting that changes at this position can have an influence, direct or indirect, on ligand interactions that occur to the PTHR J domain.

Example 5

Effects on cAMP and IP signaling—Selected analogs of [$Ala^1,Arg^{19}$]hPTH(1-31)$NH_2$ with substitutions that markedly impaired binding to HKRK-B7 cells were assessed for their capacity to bind to the PTHR in ROS 17/2.8 cells and to stimulate cAMP-signaling responses in these cells. These bone-derived cells endogenously express the rat PTHR at a more physiological level than is found in HKRK-B7 cells (approximately 80,000 PTHRs per cell vs. 950,000 PTHRs per cell) and, have generally been found (data not shown) to yield closer correlations between PTH analog binding affinity and cAMP-signaling potency than do HKRK-B7 cells, presumably due to their lower PTHR expression level. Competition binding assays performed in these cells utilizing $^{125}$I-PTH(1-34) tracer radioligand revealed effects of the substitutions on PTHR-binding affinity that paralleled the corresponding effects seen in HKRK-137 cells. Thus, in ROS 17/2.8 cells, the Glu substitutions at $Arg^{20}$, $Trp^{23}$, $Leu^{24}$ and $Leu^{28}$ reduced affinity by 20,000- to 150-fold, and the Cha substitutions at $Arg^{20}$, $Trp^{23}$ and $Leu^{24}$ reduced affinity by 10- to 120-fold (FIG. 6A; Table 3). These effects on binding affinity in ROS 17/2.8 cell were accompanied by parallel reductions in cAMP-stimulating potency, although the effects on cAMP signaling potency were generally not as severe as the corresponding effects on binding affinity (FIG. 6B; Table 3). Each substituted analog also produced the same maximum cAMP response as did the parental peptide. Each of the alanine-substituted PTH(1-31)$NH_2$ analogs was also tested at a concentration of $1\times10^{-6}$ M, for the capacity to stimulate inositol phosphate (IP) production in COS-7 cells transfected with the PTHR (PTH-induced IP responses in HKRKB7 and ROS 17/2.8 cells are generally too low to detect, data not shown). Each analog stimulated the same four-fold increase in total IP levels as did the parent peptide. Thus, the data combined indicate that the substitutions that caused strong effects on PTHR-binding affinity did not cause severe disruptions in either the cAMP or inositol phosphate signaling capacity of the ligand. This finding is consistent with the notion that the principal ligand determinants of receptor activation, in terms of $G\alpha_s$-mediated cAMP and $G\alpha_q$-mediated $IP_3$ signaling, reside in the amino-terminal domain of the ligand (Shimizu, M., et al. (2000) *J. Biol. Chem.* 275:21836-21843; Takasu, H., et al. (1999) *J Bone Miner Res.* 14:11-20) and are not perturbed by the carboxyl-terminal substitutions of the PTH(1-31) analogs.

TABLE 3

Activities in ROS 17/2.8 Cells

| | Binding $IC_{50}$ | cAMP $EC_{50}$ |
|---|---|---|
| [$Ala^1,Arg^{19}$]PTH(1-31) | 1.6 ± 0.2 | 0.78 ± 0.24 |
| $Arg^{20}$→Cha | 290 ± 130 | 7.5 ± 3.0 |
| $Trp^{23}$→Cha | 19 ± 7 | 0.82 ± 0.11 |
| $Leu^{24}$→Cha | 7.3 ± 0.8 | 0.83 ± 0.17 |
| $Arg^{20}$→Glu | 5,800 ± 1,200 | 59 ± 31 |
| $Trp^{23}$→Glu | 220 ± 60 | 4.0 ± 2.0 |
| $Leu^{24}$→Glu | 29,000 ± 5,000 | 250 ± 70 |
| $Leu^{28}$→glu | 3,100 ± 2,100 | 11 ± 2 |

Peptide are analogs of [$Ala^1,Arg^{19}$]hPTH(1-31)$NH_2$. Competition binding was assessed in cells using $^{125}$I-[$Nle^{8,21},Tyr^{34}$]rPTH(1-34)$NH_2$ tracer radioligand. Values (nM) are means (+/−s.e.m.) of data from three experiments, each performed in duplicate.

CONCLUSIONS

There is currently little information available that speaks to the specific functional roles that amino acid side chains in the (17-31) domain of PTH, the principal-receptor binding domain, play in the receptor-interaction process. The current studies were designed to explore these roles using a number of new PTH(1-31) analogs modified in the (17-31) domain, together with a new PTH-receptor binding assay that utilizes PTHR-delNt as a means to resolve whether a ligand substitution alters interaction to the receptor's amino-terminal extracellular (N) domain, or to its juxtamembrane (J) domain containing the extracellular loops and transmembrane helices. The overall data from these studies are largely consistent with the two-domain model that has been proposed for the PTH-PTHR interaction mechanism, as well as for the class 2 GPCRs in general, in that they suggest that the major binding interactions occur between residues in the carboxyl-terminal portion of the ligand and the N domain of the receptor.

In the studies on a large number of PTH(1-31)$NH_2$ or [$Ala^1,Arg^{19}$]PTH(1-31)$NH_2$ analogs altered in the (17-31) region, it was found that the strongest effects on binding to the intact PTHR occurred with non-conservative Glu substitutions at $Arg^{20}$, $Trp^{23}$, $Leu^{24}$ and $Leu^{28}$—each of which reduced PTHR-binding affinity by at least 150-fold. These data are thus in agreement with previous PTH-substitution studies which highlighted the importance of these same residues in binding to the intact PTHR (Gardella, T. J., et al. (1993) *Endocrinology* 132:2024-2030; Oldenburg, K. R., et al. (1996) *Journal Of Biological Chemistry* 271:17582-17591; Reidhaar-Olson, J., et al. (2000) *Mol Cell Endocrinol* 160:135-147; Neugebauer, W., at al. (1992) *Biochemistry* 31:2056-2063). As is now shown that the same Glu substitutions have little or no effect on binding to PTHR-delNt, and do not cause major perturbations of the ligand's helical structure, it can be concluded that the side chains of $Arg^{20}$, $Trp^{23}$, $Leu^{24}$ and $Leu^{28}$ indeed contribute to the PTHR-binding process by mechanisms that largely, if not completely, involve interactions to the receptor's N-terminal domain.

The side chains of $Trp^{23}$, $Leu^{24}$ and $Leu^{28}$ form the hydrophobic face of the amphiphilic α-helix predicted for the (17-31) region of PTH (Neugebauer, W., et al. (1992) *Biochemistry* 31:2056-2063; Epand, R. E. (1983) *Mol and Cell Biol* 57:41-47). It has been suggested for peptide ligands in general (Sargent, D., and Schwyzer, R. (1986) *Proc Natl Acad Sci USA* 83:5774-5778), including for PTH (Pellegrini, M., et al. (1998) *Biochemistry* 37:12737-12743), that such an amphiphilic α-helix can contribute to the receptor-binding process by enabling nonspecific hydrophobic interactions with the lipid component of the cell membrane, to thus facilitate a two-dimensional diffusion to the receptor. That the Glu substitutions at Trp$^{23}$, Leu$^{24}$ and Leu$^{28}$ only mildly impaired binding to PTHR-delNt strongly suggest, however, that the effects of these substitutions are not based on a disruption of nonspecific interactions with the cell membrane, as such effects would have been equally apparent on the intact PTHR and on PTHR-delNt. This conclusion is further supported by findings that the replacement of Trp$^{23}$ and Leu$^{24}$ by cyclohexylalanine (Cha), which preserves hydrophobicity and thus the capacity for non-specific interactions with the lipid membrane, reduced binding on the intact PTHR by approximately 12-fold, and again had little or no effect on binding to PTHR-delNt (Table 2). It thus appears that more specific physicochemical features of the tryptophan-23 and leucine-24 side chains, other than hydrophobicity per se, are required for high affinity interactions with the receptor.

It is clear from the current data, and that presented elsewhere (Oldenburg, K. R., et al. (1996) *Journal Of Biological Chemistry* 271:17582-17591; Barbier, J., at al. (2001) *Biochemistry* 40:8955-8961; Reidhaar-Olson, J., et al. (2000) *Mol Cell Endocrinol* 160:135-147), that the highly conserved arginine at position 20 of PTH plays a key role in the PTHR-binding process. Of ten substitutions tested at this position in the PTH(1-31)NH$_2$ scaffold peptide, citrulline, PipGly and norleucine reduced affinity for the PTHR by –200-fold and the remaining substitutions abolished binding altogether. As each of these substitutions had only a minor effect on binding to PTHR-delNt, the side chain of Arg$^{20}$, like those of Trp$^{23}$, Leu$^{24}$ and Leu$^{28}$, must contribute to the PTHR-binding process via a mechanism that primarily involves interactions to the PTHR N domain. The overall data, however, based on a considerable number of structurally varied amino acids, are consistent with the notion that multiple components of the arginine side chain, including the cationic and H-bonding nitrogen atoms of the guanidino group and the aliphatic side chain linker, participate in the interaction and must align precisely with cognate functional groups in the receptor (Barbier, J., et al. (2001) *Biochemistry* 40:8955-8961). In any event, it now seems clear that these cognate functional groups are located predominantly, if not exclusively, in the receptor's N domain region.

In contrast to arginine 20, residue 19 of PTH appears to interact predominantly with the PTHR J domain. This can be seen in the current data by the 90-fold reduction in binding affinity on PTHR-delNt caused by the Arg$^{19}$ to Glu substitution in [Ala$^1$,Arg$^{19}$]PTH(1-31)NH$_2$—the strongest effect on binding to PTHR-delNt of any substitution tested. This reduction in binding affinity mirrors the enhancing effect that the Glu$^{19}$ to Arg substitution in PTH(1-34) and PTH(1-20) analogs has on the cAMP-stimulating potencies of the analogs in COS-7 cells expressing PTHR-delNt (Shimizu, M., et al (2002) *Biochemistry* 41:13224-13233). That the side chain of residue 19 comes within proximity of the PTHR J domain is further shown by the cross-linking of [Bpa$^{19}$]PTHrP(1-36) and [Bpa$^{19}$]PTH(1-20) analogs to the extracellular end of transmembrane helix 2 of the PTHR (Gensure, R. C., et al (2003) *Mol Endocrinol* 17:2647-58). These data for residue 19, considered together with those described above for Arg$^{20}$, intriguingly suggest that the 19/20 position in the ligand may comprise a boundary between segments of PTH that interact with the N and J domain regions of the receptor—PTH segments (20-31) and (1-19), respectively.

Finally, the studies provide insights into the topology of the PTH ligand, as it is bound to the receptor, and of the spatial relationship of the N and J domains of the ligand-occupied PTHR. Subtle but consistent effects of substitutions at positions 21, 25, 26 and 27 on interaction of the ligand with PTHR-delNt were found, and these effects were accompanied by approximately proportional effects on interaction with the intact PTHR. Such findings point to the possibility that the side chains of these residues, while not contributing in a major way to overall binding energy, can influence the ligand-binding interactions that occur to the PTHR J domain. The cationic side chains of Arg$^{25}$, Lys$^{26}$ and Lys$^{27}$ would form the hydrophilic face of the ligand's amphiphilic α-helix, and Val$^{21}$ would lie at the edge of this face (Barbier, J. R., et al. (2005) *J Biol Chem.* 280:23771-23777). It is possible that these side chains modulate binding affinity indirectly, for example, by interacting with the phospholipid head groups of the cell membrane bilayer, to facilitate diffusion to the receptor, as discussed above. However, more direct interactions with presumably anionic and/or hydrophobic groups in the extracellular loops and/or transmembrane domain regions of the receptor are also possible. Indeed, the cross-linking of [Lys$^{27}$(Bp$_z$)]PTH(1-34) to the first extracellular loop of the PTHR (Greenberg, Z., et al. (2000) *Biochemistry* 39:8142-8152) supports this latter possibility, as do the recent findings that backbone methylations at Ser$^{17}$, Trp$^{23}$ and Lys$^{26}$ in PTH (1-31)NH$_2$ impair, albeit modestly, the capacity of the ligand to stimulate cAMP signaling via PTHR-delNt (Barbier, J. R., et al. (2005) *J Biol Chem.* 280:23771-23777).

If the ligand's carboxyl-terminal a-helical domain, in addition to its amino-terminal PTH(1-19) domain (see above) interact with the PTHR J domain, then a fold or bend between the amino- and carboxyl-terminal domains of the bound ligand would seem to be required in order to accommodate both sets of interactions. Most solution-phase NMR studies of PTH and PTHrP ligands indeed show a hinge or flexible region between the amino-terminal and carboxyl-terminal domains (Chen, Z., et al. (2000) *Biochemistry* 39:12766-12777; Pellegrini, M., et al. (1998) *J. Biol. Chem.* 273:10420-10427; Barden, J. A., and Kemp, B. E. (1994) *Biochim Biophys Acta* 1208:256-262; Peggion, E., et al. (2002) *Biochemistry* 41:8162-8175), that could facilitate such a bend. That the receptor-bound ligand adopts a mid-region fold is further suggested by the finding that [Bpa$^{11}$]PTH(1-34) and [Bpa$^{21}$]PTH(1-34) analogs each cross-link to the same segment (Ala$^{165}$-Asn$^{176}$) of the PTHR N domain, as the two contacts are not easily reconciled with a linear ligand structure (Wittelsberger, A., et al. (2006) *Biochemistry* 45:2027-34). The notion that PTH adopts a mid-region bend in the receptor bound state differs from a recent model of the pituitary adenylyl cyclase-activating peptide bound to its related class 2 GPCR, since in this model the ligand is portrayed as a linear extended helix making extensive contacts to the receptor's N domain (Tan, Y. V., et al. (2006) *J Biol Chem* 281:12792-8).

If the carboxyl-terminal helical domain of PTH indeed interacts with J domain, as well as the N domain regions of the receptor, via its hydrophobic and hydrophilic faces, respectively, and these interactions were to occur simultaneously, then the N and J domains of the occupied receptor would have to be near each other in order to accommodate both sets of interactions. This possibility is supported by the cross-linking of [Bpa$^{27}$]PTH(1-34), having Lys$^{27}$ replaced by benzoylphenylalanine, to the receptor's N domain (Gensure, R., et al. (2001) *J Biol Chem* 276:28650-28658), and that of [Lys$^{27}$(Bp$_z$)]PTH(1-34) to the receptor's first extracellular loop (Greenberg, Z., et al. (2000) *Biochemistry* 39:8142-8152).

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All publications, patents and patent applications cited herein are incorporated by reference in their entirety into the disclosure.

What is claimed is:

1. An isolated peptide consisting of the formula:
   (a) $X_{01}$ValSerGluIleGlnLeuMetHisAsnLeuGlyLys HisLeuAsnSerMet$X_{02}X_{03}X_{04}$Glu$X_{05}X_{06}$ArgLysLys $X_{07}$GlnAspVal (SEQ ID NO:1);
   (b) a fragment thereof, containing amino acids 1-20, 1-21, 1-22, 1-23, 1-24, 1-25, 1-26, 1-27, 1-28, 1-29, or 1-30;
   (c) a pharmaceutically acceptable salt thereof; or
   (d) an N-terminal or C-terminal derivative thereof having a modification at the free N-terminal end or free C-terminal end;

wherein:
   $X_{01}$ is Ser or Ala;
   $X_{02}$ is Glu or Arg;
   $X_{03}$ is Ala, Arg, Glu, Gln, or cyclohexylalanine (Cha);
   $X_{04}$ is Val or Glu;
   $X_{05}$ is Trp, Ala, Glu, or Cha;
   $X_{06}$ is Leu, Ala, Glu, or Cha; and
   $X_{07}$ is Leu or Glu;

provided that said peptide, said fragment thereof, said pharmaceutically acceptable salt thereof, or said N-terminal or C-terminal derivative thereof is not hPTH(1-31)NH$_2$ (SEQ ID NO:13), [Ala$^{20}$]hPTH(1-31)NH$_2$ (SEQ ID NO:2), [Glu$^{20}$]hPTH(1-31)NH$_2$ (SEQ ID NO:5), or [Gln$^{20}$]hPTH(1-31)NH$_2$ (SEQ ID NO:14).

2. The peptide of claim 1, wherein $X_{03}$ is Cha.

3. The peptide of claim 1, consisting of the formula:
   (a) SerValSerGluIleGlnLeuMetHisAsnLeuGlyLys HisLeuAsnSerMetGluArgValGlu-AlaLeuArgLysLysLeuGlnAspVal (SEQ ID NO:3);
   (b) a fragment thereof, containing amino acids 1-20, 1-21, 1-22, 1-23, 1-24, 1-25, 1-26, 1-27, 1-28, 1-29, or 1-30;
   (c) a pharmaceutically acceptable salt thereof; or
   (d) an N-terminal or C-terminal derivative thereof having a modification at the free N-terminal end or free C-terminal end.

4. The peptide of claim 1, consisting of the formula:
   (a) SerValSerGluIleGlnLeuMetHisAsnLeuGly LysHisLeuAsnSerMetGluArgVal-GluTrpAlaArgLysLysLeuGlnAspVal (SEQ ID NO:4);
   (b) a fragment thereof, containing amino acids 1-20, 1-21, 1-22, 1-23, 1-24, 1-25, 1-26, 1-27, 1-28, 1-29, or 1-30;
   (c) a pharmaceutically acceptable salt thereof; or
   (d) an N-terminal or C-terminal derivative thereof having a modification at the free N-terminal end or free C-terminal end.

5. The peptide of claim 1, consisting of the formula:
   (a) AlaValSerGluIleGlnLeuMetHis-AsnLeuGlyLysHisLeuAsnSer-MetArgArgValGluGluLeuArgLysLysLeuGlnAspVal (SEQ ID NO:6);
   (b) a fragment thereof, containing amino acids 1-20, 1-21, 1-22, 1-23, 1-24, 1-25, 1-26, 1-27, 1-28, 1-29, or 1-30;
   (c) a pharmaceutically acceptable salt thereof; or
   (d) an N-terminal or C-terminal derivative thereof having a modification at the free N-terminal end or free C-terminal end.

6. The peptide of claim 1, consisting of the formula:
   (a) AlaValSerGluIleGlnLeuMetHisAsnLeuGlyLysHis LeuAsnSerMetArgArgValGluTrp-GluArgLysLysLeuGlnAspVal (SEQ ID NO:7);
   (b) a fragment thereof, containing amino acids 1-20, 1-21, 1-22, 1-23, 1-24, 1-25, 1-26, 1-27, 1-28, 1-29, or 1-30;
   (c) a pharmaceutically acceptable salt thereof; or
   (d) an N-terminal or C-terminal derivative thereof having a modification at the free N-terminal end or free C-terminal end.

7. The peptide of claim 1, consisting of the formula:
   (a) AlaValSerGluIleGlnLeuMetHis-AsnLeuGlyLysHisLeuAsnSer-MetArgArgValGluTrpLeuArgLysLysGluGlnAspVal (SEQ ID NO:8);
   (b) a fragment thereof, containing amino acids 1-20, 1-21, 1-22, 1-23, 1-24, 1-25, 1-26, 1-27, 1-28, 1-29, or 1-30;
   (c) a pharmaceutically acceptable salt thereof; or
   (d) an N-terminal or C-terminal derivative thereof having a modification at the free N-terminal end or free C-terminal end.

8. The peptide of claim 1, consisting of the formula:
   (a) AlaValSerGluIleGlnLeuMetHis-AsnLeuGlyLysHisLeuAsnSer-MetArgArgGluGluTrpLeuArgLysLysLeuGlnAspVal (SEQ ID NO:9);
   (b) a fragment thereof, containing amino acids 1-20, 1-21, 1-22, 1-23, 1-24, 1-25, 1-26, 1-27, 1-28, 1-29, or 1-30;
   (c) a pharmaceutically acceptable salt thereof; or
   (d) an N-terminal or C-terminal derivative thereof having a modification at the free N-terminal end or free C-terminal end.

9. The peptide of claim 1, consisting of the formula:
   (a) AlaValSerGluIleGlnLeuMetHis-AsnLeuGlyLysHisLeuAsnSer-MetArgChaValGluTrpLeuArgLysLysLeuGlnAspVal (SEQ ID NO:10);
   (b) a fragment thereof, containing amino acids 1-20, 1-21, 1-22, 1-23, 1-24, 1-25, 1-26, 1-27, 1-28, 1-29, or 1-30;
   (c) a pharmaceutically acceptable salt thereof; or
   (d) an N-terminal or C-terminal derivative thereof having a modification at the free N-terminal end or free C-terminal end.

10. The peptide of claim 1, consisting of the formula:
    (a) AlaValSerGluIleGlnLeuMetHis-AsnLeuGlyLysHisLeuAsnSer-MetArgArgValGluChaLeuArgLysLysLeuGlnAspVal (SEQ ID NO:11);
    (b) a fragment thereof, containing amino acids 1-20, 1-21, 1-22, 1-23, 1-24, 1-25, 1-26, 1-27, 1-28, 1-29, or 1-30;
    (c) a pharmaceutically acceptable salt thereof; or
    (d) an N-terminal or C-terminal derivative thereof having a modification at the free N-terminal end or free C-terminal end.

11. The peptide of claim 1, consisting of the formula:
    (a) AlaValSerGluIleGlnLeuMetHis-AsnLeuGlyLysHisLeuAsnSer-MetArgArgValGluTrpChaArgLysLysLeuGlnAspVal (SEQ ID NO:12);

(b) a fragment thereof, containing amino acids 1-20, 1-21, 1-22, 1-23, 1-24, 1-25, 1-26, 1-27, 1-28, 1-29, or 1-30;
(c) a pharmaceutically acceptable salt thereof; or
(d) an N-terminal or C-terminal derivative thereof having a modification at the free N-terminal end or free C-terminal end.

12. The peptide of claim 1, wherein said peptide is labeled with a label selected from the group consisting of a radiolabel, a fluorescent label, a bioluminescent label, and a chemiluminescent label.

13. A pharmaceutical composition comprising the peptide of claim 1 and a pharmaceutically acceptable carrier.

14. The peptide of claim 1, consisting of the formula SerValSerGluIleGlnLeuMetHis-AsnLeuGlyLysHisLeuAsnSerMet-GluArgValGluAlaLeuArgLysLysLeuGlnAspVal (SEQ ID NO:3), or a pharmaceutically acceptable salt thereof.

15. The peptide of claim 1, consisting of the formula SerValSerGluIleGlnLeuMetHis-AsnLeuGlyLysHisLeuAsnSerMet-GluArgValGluTrpAlaArgLysLysLeuGlnAspVal (SEQ ID NO:4), or a pharmaceutically acceptable salt thereof.

16. The peptide of claim 1, consisting of the formula AlaValSerGluIleGlnLeuMetHis-AsnLeuGlyLysHisLeuAsnSer-MetArgArgValGluGluLeuArgLysLysLeuGlnAspVal (SEQ ID NO:6), or a pharmaceutically acceptable salt thereof.

17. The peptide of claim 1, consisting of the formula AlaValSerGluIleGlnLeuMetHis-AsnLeuGlyLysHisLeuAsnSer-MetArgArgValGluTrpGluArgLysLysLeuGlnAspVal (SEQ ID NO:7), or a pharmaceutically acceptable salt thereof.

18. The peptide of claim 1, consisting of the formula AlaValSerGluIleGlnLeuMetHisAsnLeuGlyLys HisLeuAsnSerMetArgArgValGluTrpLeu ArgLysLys-GluGlnAspVal (SEQ ID NO:8), or a pharmaceutically acceptable salt thereof.

19. The peptide of claim 1, consisting of the formula AlaValSerGluIleGlnLeuMetHis-AsnLeuGlyLysHisLeuAsnSer-MetArgArgGluGluTrpLeuArgLysLysLeuGlnAspVal (SEQ ID NO:9), or a pharmaceutically acceptable salt thereof.

20. The peptide of claim 1, consisting of the formula AlaValSerGluIleGlnLeuMetHis-AsnLeuGlyLysHisLeuAsnSer-MetArgChaValGluTrpLeuArgLysLysLeuGlnAspVal (SEQ ID NO:10), or a pharmaceutically acceptable salt thereof.

21. The peptide of claim 1, consisting of the formula AlaValSerGluIleGlnLeuMetHis-AsnLeuGlyLysHisLeuAsnSer-MetArgArgValGluChaLeuArgLysLysLeuGlnAspVal (SEQ ID NO:11), or a pharmaceutically acceptable salt thereof.

22. The peptide of claim 1, consisting of the formula AlaValSerGluIleGlnLeuMetHis-AsnLeuGlyLysHisLeuAsnSer-MetArgArgValGluTrpChaArgLysLysLeuGlnAspVal (SEQ ID NO:12), or a pharmaceutically acceptable salt thereof.

* * * * *

```
                              SEQUENCE LISTING

<160> NUMBER OF SEQ ID NOS: 14

<210> SEQ ID NO 1
<211> LENGTH: 31
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Ser or Ala
<220> FEATURE:
<221> NAME/KEY: MISC_FEATURE
<222> LOCATION: (19)..(19)
<223> OTHER INFORMATION: Xaa is Glu or Arg
<220> FEATURE:
<221> NAME/KEY: MISC_FEATURE
<222> LOCATION: (20)..(20)
<223> OTHER INFORMATION: Xaa is Ala, Glu, Gln, or Cyclohexylalanine
<220> FEATURE:
<221> NAME/KEY: MISC_FEATURE
<222> LOCATION: (21)..(21)
<223> OTHER INFORMATION: Xaa is Val or Glu
<220> FEATURE:
<221> NAME/KEY: MISC_FEATURE
<222> LOCATION: (23)..(23)
<223> OTHER INFORMATION: Xaa is Trp, Ala, Glu, or Cyclohexylalanine
<220> FEATURE:
<221> NAME/KEY: MISC_FEATURE
<222> LOCATION: (24)..(24)
<223> OTHER INFORMATION: Xaa is Leu, Ala, Glu, or Cyclohexylalanine
<220> FEATURE:
<221> NAME/KEY: MISC_FEATURE
<222> LOCATION: (28)..(28)
<223> OTHER INFORMATION: Xaa is Leu or Glu

<400> SEQUENCE: 1

Xaa Val Ser Glu Ile Gln Leu Met His Asn Leu Gly Lys His Leu Asn
1               5                   10                  15

Ser Met Xaa Xaa Xaa Glu Xaa Xaa Arg Lys Lys Xaa Gln Asp Val
            20                  25                  30

<210> SEQ ID NO 2
<211> LENGTH: 31
<212> TYPE: PRT
<213> ORGANISM: Homo sapiens

<400> SEQUENCE: 2

Ser Val Ser Glu Ile Gln Leu Met His Asn Leu Gly Lys His Leu Asn
1               5                   10                  15

Ser Met Glu Ala Val Glu Trp Leu Arg Lys Lys Leu Gln Asp Val
            20                  25                  30

<210> SEQ ID NO 3
<211> LENGTH: 31
<212> TYPE: PRT
<213> ORGANISM: Homo sapiens

<400> SEQUENCE: 3

Ser Val Ser Glu Ile Gln Leu Met His Asn Leu Gly Lys His Leu Asn
1               5                   10                  15

Ser Met Glu Arg Val Glu Ala Leu Arg Lys Lys Leu Gln Asp Val
            20                  25                  30
```

<210> SEQ ID NO 4
<211> LENGTH: 31
<212> TYPE: PRT
<213> ORGANISM: Homo sapiens

<400> SEQUENCE: 4

Ser Val Ser Glu Ile Gln Leu Met His Asn Leu Gly Lys His Leu Asn
1               5                   10                  15

Ser Met Glu Arg Val Glu Trp Ala Arg Lys Lys Leu Gln Asp Val
            20                  25                  30

<210> SEQ ID NO 5
<211> LENGTH: 31
<212> TYPE: PRT
<213> ORGANISM: Homo sapiens

<400> SEQUENCE: 5

Ser Val Ser Glu Ile Gln Leu Met His Asn Leu Gly Lys His Leu Asn
1               5                   10                  15

Ser Met Glu Glu Val Glu Trp Leu Arg Lys Lys Leu Gln Asp Val
            20                  25                  30

<210> SEQ ID NO 6
<211> LENGTH: 31
<212> TYPE: PRT
<213> ORGANISM: Homo sapiens

<400> SEQUENCE: 6

Ala Val Ser Glu Ile Gln Leu Met His Asn Leu Gly Lys His Leu Asn
1               5                   10                  15

Ser Met Arg Arg Val Glu Glu Leu Arg Lys Lys Leu Gln Asp Val
            20                  25                  30

<210> SEQ ID NO 7
<211> LENGTH: 31
<212> TYPE: PRT
<213> ORGANISM: Homo sapiens

<400> SEQUENCE: 7

Ala Val Ser Glu Ile Gln Leu Met His Asn Leu Gly Lys His Leu Asn
1               5                   10                  15

Ser Met Arg Arg Val Glu Trp Glu Arg Lys Lys Leu Gln Asp Val
            20                  25                  30

<210> SEQ ID NO 8
<211> LENGTH: 31
<212> TYPE: PRT
<213> ORGANISM: Homo sapiens

<400> SEQUENCE: 8

Ala Val Ser Glu Ile Gln Leu Met His Asn Leu Gly Lys His Leu Asn
1               5                   10                  15

Ser Met Arg Arg Val Glu Trp Leu Arg Lys Lys Glu Gln Asp Val
            20                  25                  30

<210> SEQ ID NO 9
<211> LENGTH: 31
<212> TYPE: PRT
<213> ORGANISM: Homo sapiens

<400> SEQUENCE: 9

Ala Val Ser Glu Ile Gln Leu Met His Asn Leu Gly Lys His Leu Asn
1               5                   10                  15

Ser Met Arg Arg Glu Glu Trp Leu Arg Lys Lys Leu Gln Asp Val
            20                  25                  30

<210> SEQ ID NO 10
<211> LENGTH: 31
<212> TYPE: PRT
<213> ORGANISM: Homo sapiens
<220> FEATURE:
<221> NAME/KEY: MISC_FEATURE
<222> LOCATION: (20)..(20)
<223> OTHER INFORMATION: Xaa is Cyclohexylalanine

<400> SEQUENCE: 10

Ala Val Ser Glu Ile Gln Leu Met His Asn Leu Gly Lys His Leu Asn
1               5                   10                  15

Ser Met Arg Xaa Val Glu Trp Leu Arg Lys Lys Leu Gln Asp Val
            20                  25                  30

<210> SEQ ID NO 11
<211> LENGTH: 31
<212> TYPE: PRT
<213> ORGANISM: Homo sapiens
<220> FEATURE:
<221> NAME/KEY: MISC_FEATURE
<222> LOCATION: (23)..(23)
<223> OTHER INFORMATION: Xaa is Cyclohexylalanine

<400> SEQUENCE: 11

Ala Val Ser Glu Ile Gln Leu Met His Asn Leu Gly Lys His Leu Asn
1               5                   10                  15

Ser Met Arg Arg Val Glu Xaa Leu Arg Lys Lys Leu Gln Asp Val
            20                  25                  30

<210> SEQ ID NO 12
<211> LENGTH: 31
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Cyclohexylalanine

<400> SEQUENCE: 12

Ala Val Ser Glu Ile Gln Leu Met His Asn Leu Gly Lys His Leu Asn
1               5                   10                  15

Ser Met Arg Arg Val Glu Trp Xaa Arg Lys Lys Leu Gln Asp Val
            20                  25                  30

<210> SEQ ID NO 13
<211> LENGTH: 31
<212> TYPE: PRT
<213> ORGANISM: Homo sapiens

<400> SEQUENCE: 13

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30

<210> SEQ ID NO 14
<211> LENGTH: 31
<212> TYPE: PRT
<213> ORGANISM: Homo sapiens

<400> SEQUENCE: 14

```
Ser Val Ser Glu Ile Gln Leu Met His Asn Leu Gly Lys His Leu Asn
1               5                   10                  15

Ser Met Glu Gln Val Glu Trp Leu Arg Lys Lys Leu Gln Asp Val
            20              25              30
```